United States Patent
Santamaría et al.

(10) Patent No.: US 6,800,473 B1
(45) Date of Patent: Oct. 5, 2004

(54) HUMAN CATHEPSIN L2 PROTEIN, GENE ENCODING SAID PROTEIN AND USE THEREOF

(75) Inventors: Inigo Santamaría, Oviedo (ES); Gloria Velasco, Salinas (ES); Maite Cazorla, Barcelona (ES); Antonio Fueyo, Oviedo (ES); Elías Campo, Barcelona (ES); Carlos López-Otín, Salinas (ES)

(73) Assignees: Daiichi Fine Chemical Co., Ltd., Toyama (JP); Universidad de Oviedo, Asturias (ES)

( * ) Notice: Subject to any disclaimer, the term of this patent is extended or adjusted under 35 U.S.C. 154(b) by 596 days.

(21) Appl. No.: 09/290,586

(22) Filed: Apr. 13, 1999

(30) Foreign Application Priority Data

Jun. 5, 1998 (JP) .......................................... 10-172147

(51) Int. Cl.[7] .............................. C12N 9/50; C12Q 1/37; C07K 17/00; C12P 21/06; A61K 38/46
(52) U.S. Cl. ........................ 435/226; 435/23; 435/691; 435/471; 435/212; 435/325; 435/252.3; 435/320.1; 435/219; 424/94.65; 530/350; 536/23.2
(58) Field of Search ....................... 424/94.65; 435/212, 435/23, 69.1, 471, 219, 325, 252.3, 320.1, 226; 530/350; 536/23.2

(56) References Cited

U.S. PATENT DOCUMENTS 6,033,893 A * 3/2000 Bandman et al. ........... 435/212

OTHER PUBLICATIONS

Okamura, N. et al., Bioch. Biophys. Acta, vol. 1245, pp. 221–226, 1995.*
Bromme, D. et al., GeneBank Database, Accession No. AAC23598, Jun. 17, 1998.*
Mathews, C. et al., Biochemistry, Benjamin/Cummings Publ. Co., Inc., CA, p. 142, 1990.*
Ingio Santamaría et al., "Cathepsin L2, a Novel Human Cysteine Proteinase Produced by Breast and Colorectal Carcinomas[1]", Cancer Research, vol. 58, pp. 1624–1630, Apr. 15, 1998.
Susannah Gal, et al., "Isolation and sequence of a cDNA for human pro–(cathepsin L)", Biochem. J. (1988), vol. 253, pp. 303–306.
S. D. Bryce, et al., "A Novel Family of Cathepsin L–like (CTSLL) Sequences on Human Chromosome 10q and Related Transcripts", Genomics 24, pp. 568–576 (1994).

* cited by examiner

*Primary Examiner*—Rebecca E. Prouty
(74) *Attorney, Agent, or Firm*—Wenderoth, Lind & Ponack, L.L.P.

(57) ABSTRACT

Novel proteins which belong to the papain family and are cysteine proteinase enzymes (the cysteine proteinase enzymes are expected to be involved in the turnover of intracellular proteins, antigen presentation, prohormone activation, bone remodeling, etc. and to play important roles in a variety of pathological conditions such as Alzheimer's disease, pulmonary emphysema, rheumatoid arthritis, muscular dystrophy, osteoporosis, neurodegenerative disease, and cancer invasion and metastasis), together with genes encoding the proteins and antibodies against the proteins, can be conveniently used in elucidating the function of a cysteine proteinase involved in various diseases and disorders, especially cancers, thereby not only disclosing critical mechanism leading to such diseases and disorders but also researching and developing therapy and therapeutic drugs thereagainst. The novel cathepsin (especially, human cathepsin L2) is cloned from human cDNA library, thereby leading to, DNA containing a nucleotide sequence coding for the protein, host cells transformed with the DNA, processes for producing the human cathepsin L2 protein which comprise using the host cell, monoclonal antibodies which bind with the cathepsin L2 protein and use of the protein, antibodies and nucleic acids.

5 Claims, 8 Drawing Sheets

FIG. 1(A)

SEQ ID NO: 15

```
  1  CGGCTGTAATCTCAGAGGCTTGTTTGCTGAGGGTGCCTGCGCACGTGCGACGGCTGCTGG   60

61  TTTTGAAACATGAATCTTTCGCTCGTCCTGGCTGCCTTTTGCTTGGGAATAGCCTCCGCT  120
              M  N  L  S  L  V  L  A  A  F  C  L  G  I  A  S  A

121  GTTCCAAAATTTGACCAAAATTTGGATACAAAGTGGTACCAGTGGAAGGCAACACACAGA  180
     V  P  K  F  D  Q  N  L  D  T  K  W  Y  Q  W  K  A  T  H  R
     ↳

181  AGATTATATGGCGCGAATGAAGAAGGATGGAGGAGAGCAGTGTGGGAAAAGAATATGAAA  240
      R  L  Y  G  A  N  E  E  G  W  R  R  A  V  W  E  K  N  M  K

241  ATGATTGAACTGCACAATGGGGAATACAGCCAAGGGAAACATGGCTTCACAATGGCCATG  300
      M  I  E  L  H  N  G  E  Y  S  Q  G  K  H  G  F  T  M  A  M

301  AATGCTTTTGGTGACATGACCAATGAAGAATTCAGGCAGATGATGGGTTGCTTTCGAAAC  360
      N  A  F  G  D  M  T  N  E  E  F  R  Q  M  M  G  C  F  R  N

361  CAGAAATTCAGGAAGGGGAAAGTGTTCCGTGAGCCTCTGTTTCTTGATCTTCCCAAATCT  420
      Q  K  F  R  K  G  K  V  F  R  E  P  L  F  L  D  L  P  K  S
                                                        ↳

421  GTGGATTGGAGAAAGAAAGGCTACGTGACGCCAGTGAAGAATCAGAAACAGTGTGGTTCT  480
      V  D  W  R  K  K  G  Y  V  T  P  V  K  N  Q  K  Q  C  G  S

481  TGTTGGGCTTTTAGTGCGACTGGTGCTCTTGAAGGACAGATGTTCCGGAAAACTGGGAAA  540
      C  W  A  F  S  A  T  G  A  L  E  G  Q  M  F  R  K  T  G  K

541  CTTGTCTCACTGAGCGAGCAGAATCTGGTGGACTGTTCGCGTCCTCAAGGCAATCAGGGC  600
      L  V  S  L  S  E  Q  N  L  V  D  C  S  R  P  Q  G  N  Q  G

601  TGCAATGGTGGCTTCATGGCTAGGGCCTTCCAGTATGTCAAGGAGAACGGAGGCCTGGAC  660
      C  N  G  G  F  M  A  R  A  F  Q  Y  V  K  E  N  G  G  L  D
```

FIG. 1(B)

```
 661  TCTGAGGAATCCTATCCATATGTAGCAGTGGATGAAATCTGTAAGTACAGACCTGAGAAT   720
       S  E  E  S  Y  P  Y  V  A  V  D  E  I  C  K  Y  R  P  E  N

721  TCTGTTGCTAATGACACTGGCTTCACAGTGGTCGCACCTGGAAAGGAGAAGGCCCTGATG   780
       S  V  A  N  D  T  G  F  T  V  V  A  P  G  K  E  K  A  L  M

781  AAAGCAGTCGCAACTGTGGGGCCCATCTCCGTTGCTATGGATGCAGGCCATTCGTCCTTC   840
       K  A  V  A  T  V  G  P  I  S  V  A  M  D  A  G  H  S  S  F

841  CAGTTCTACAAATCAGGCATTTATTTTGAACCAGACTGCAGCAGCAAAAACCTGGATCAT   900
       Q  F  Y  K  S  G  I  Y  F  E  P  D  C  S  S  K  N  L  D  H

901  GGTGTTCTGGTGGTTGGCTACGGCTTTGAAGGAGCAAATTCGAATAACAGCAAGTATTGG   960
       G  V  L  V  V  G  Y  G  F  E  G  A  N  S  N  N  S  K  Y  W

961  CTCGTCAAAAACAGCTGGGGTCCAGAATGGGGCTCGAATGGCTATGTAAAAATAGCCAAA   1020
       L  V  K  N  S  W  G  P  E  W  G  S  N  G  Y  V  K  I  A  K

1021  GACAAGAACAACCACTGTGGAATCGCCACAGCAGCCAGCTACCCCAATGTGTGAGCTGAT   1080
       D  K  N  N  H  C  G  I  A  T  A  A  S  Y  P  N  V  *

1081  GGATGGTGAGGAGGAAGGACTTAAGGACAGCATGTCTGGGGAAATTTTATCTTGAAACTG   1140

1141  ACCAAACGCTTATTGTGTAAGATAAACCAGTTGAATCATTGAGGATCCAAGTTGAGATTT   1200

1201  TAATTCTGTGACATTTTTACAAGGGTAAAATGTTACCACTACTTTAATTATTGTTATACA   1260

1261  CAGCTTTATGATATCAAAGACTCATTGCTTAATTCTAAGACTTTTGAATTTTCATTTTTT   1320

1321  AAAAAGATGTACAAAACAGTTT   1342
```

FIG. 2(A)

```
                    1                                                                                               84
SEQ ID NO:17  CathL2 .....  MNSIVTAAF CLGIASAVPK EQNLDT.K. .........  NYQHKAT HRRLY.GANE EGHRRAVHEK NMKIELHNG EYSQGKHGFT MANNAFGDMT
SEQ ID NO:18  CathL  .....  MNPTLILAAF CLGIASASLT EQHSLEA.Q. .........  TTKKAH INRLY.GANE EGHRRAVHEK NMKIELHNQ EYREGKHSFT MANNAFGDMT
SEQ ID NO:19  CathK  .....  .MWGLKVLL LPVVSFA.LY PEELDQT.H. .........  NELHKQT HEKQYNNKVD EISRRLIWEK NLKYISIHL EASLGVTYE LAMNALGDMT
SEQ ID NO:20  CathS  .....  .MKRLVCVLL TCSSAVAQLH KQPTLDH.H. .........  NHLHKQT YGKQYKERGE EAVRRLIWEK NLKFVALHRL EHSWGASYD LGANHLGDMT
SEQ ID NO:21  CathH  MRATL PLLCAGAWLL GVPVCGAAEL SVNSLEKEH. .........  FKSFMSK HRKTY.SIEY YHHRLQTFAS NMRKINAEN. ....NGNHTEK MALNQFSDMS
SEQ ID NO:22  CathO  .MDVR ALPWLPWLLH LLCRGGGDAD SRAPTPTWP RSREREAAAF RESLN..RHR YLNSLFPSEN .........               STAF YGINQFSYLF
SEQ ID NO:23  CathW  ....M ALTAHPSCLL ALLVAGLAQG IRGPL...RA QDLGPQDLEL KEAFKLFQIQ FNRSYLSPEE HAHRLDIFAH NLAQAQRLQE E...DLGTAE FGVTPFSDLT
SEQ ID NO:24  CathB  ..... .....MWQLWA SICCLLV... .........  LANARSR PS..FHPLSD ELVNYYNKRN TTWQAGH..N FTNVDMSY L
SEQ ID NO:25  CathC  DYKWF AFFKYKEEGS KVTYTCNETM TGWVHDVLGR NWACFTGKKV GTASENVYVN TAHLKNSQEK YSNRLYKDH NFVKAINAIQ KSWTAITYME YETLTLGDW 85                                    *                           *  *   *            * 173
              CathL2 NEEEROMGC ER...NQKTB KGKVTREPLF .LDLPKSVDH RKK...G.YY TPVRNQKGCG SCHAFSAIGA LEGQMFRKTG KL...VSLSE QNLVDCSRPQ
              CathL  SEEEROVSNG FQ...NRKPR KGKVFQERLF .YEAPRSVDH RBK...G.YY TPVKRNQGCG SCHAESVVGA LEGOMFRKTG RL...ISLSE QNLVDCSGPQ
              CathK  SEEVVQNTG LKVPLSHSRS NDTLYIPEWE .GRAPDSVDY RKK...G.YV TPVKNQGQCG SCHAESSVGA LEGQLKKKTG KL...LNLSP QNLVDCVSE.
              CathS  SEVVMSLNSS LRVP.SQWQR NIT.YKSNPN .RLLPDSVDH RKK...G.CV TEVKYGGSCG ACWAESAVGA LEAQLKLKTG KL...VSLSA QNLMDCSTEK
              CathH  FAEIKHKYL. WSEPQNCSAT KSNYLRGT.. .GPYPPSVDH RKK...GNFY SPVNNGGACG SCHTSTGA LESAIAIAIG KM...LSIAE QQLMDCA..QD
              CathO  PEEFKAIY.L RSKPSKFPRY SAEYMSIPN VSLPLRFDH RD.....KQVY TQVNSQQMCG GCHAEVVGA VESAYALGGK PL...EDLSV QQVLDCS...
              CathW  EEERGQLYGY RBAAGGVPSM GREIRSEEPE .ESVPFSCDM RKV...AGAI SPIDQKNCN CCMBWASAGN IKTLWRLSFM DF...YDVSV QELLLQCG...
              CathB  K...BLC.GT ELGGPKPQR VMFTED..... .LKLPASFDA REQMPQCPTI KEIRDQGSCG SCWAFGAVEA ISDRICHI. NAHVSYEVSA EDLLTCGSM
              CathC  I...BBS.GG HSRKIPRPKP APLTAEIQQK IJHLPTSWDM BNVH.GINFY SPVRNQASCG SCYSPASMGH LEARIRILL. NNSQTPLLSP QEVYSC..SQ
```

```
         320*        334
CathL2   NNHCGIATAA  SYPNY..... ..........
CathL    RNHCGIASAA  SYPTY..... ..........
CathK    NNACGIANLA  SFPKM..... ..........
CathS    GNHCGIASFP  SYPEI..... ..........
CathH    .NMCGLAACA  SYPIPLV... ..........
CathO    SNVCGIADSV  SSIFY..... ..........
CathW    SNTCGITKFP  LTARVQKPDM KPRVSCPP..
CathB    QDHCGIESEV  VAGIPRTDQY WEKI......
CathC    TDECAIESIA  VAATPIPKL. ..........
```

HUMAN CATHEPSIN L2 PROTEIN, GENE ENCODING SAID PROTEIN AND USE THEREOF

BACKGROUND OF THE INVENTION

1. Technical Field of the Invention

The present invention relates to novel identified polynucleotides (or nucleic acids) and polypeptides (or proteins) or salts thereof, as well as peptide fragments thereof; mutants and derivatives of said polynucleotides (or nucleic acids) or said polypeptides (or proteins); to methods for producing such polynucleotides (or nucleic acids) and polypeptides (or proteins) as well as such mutants and derivatives; to agonists and antagonists of said polypeptides (or proteins); to antibodies against said polypeptides (or proteins), especially monoclonal antibodies thereagainst; and to use of said polynucleotides (or nucleic acids), polypeptides (or proteins), mutants, derivatives, agonists and antagonists.

The present invention relates to novel proteins which belong to the papain family and are cysteine proteinase enzymes (the cysteine proteinase enzymes are expected to be involved in various normal cellular processes, including the turnover of intracellular proteins, prohormone activation, and bone remodeling and to play important roles in a variety of pathological conditions such as Alzheimer's disease, pulmonary emphysema, rheumatoid arthritis, muscular dystrophy, osteoporosis, neurodegenerative disease, and cancer invasion and metastasis), useful for such studies, particularly to novel human cathepsin proteins (or fragments thereof) or salts thereof and to genes encoding the proteins or fragments. More specifically, the present invention relates to novel human cysteine proteinase-type proteins having a papain-like structure at the active site, said cysteine proteinase protein being cloned from human brain cDNA libraries (the instant novel human cysteine proteinase protein is named "Cathepsin L2"); to DNA comprising a nucleotide sequence coding for said cysteine proteinase protein; to host cells transformed with said DNA; to processes for producing said human cysteine proteinase protein by said transformed cells and to applications of such proteins and nucleic acid fragments.

2. Description of the Related Art

The cysteine proteinases are a family of enzymes involved in many normal cellular processes, including the turnover of intracellular proteins, prohormone activation, and bone remodeling (Berti, P. J., et al., J. Mol. Biol., 246: 273 to 283, 1995). In addition, it has been suggested that these proteolytic enzymes play important roles in a number of pathological conditions such as Alzheimer's disease, pulmonary emphysema, rheumatoid arthritis, muscular dystrophy, osteoporosis, and cancer invasion and metastasis (Berti, P. J., et al., J. Mol. Biol., 246: 273 to 283, 1995; Berquin, I. M., et al., Perspect. Drug Discov. Des., 2: 371 to 388, 1994).

At present, eight human cysteine proteinases of the papain family have been isolated and characterized at the amino acid sequence level: cathepsin B (Chan, S. J., et al., Proc. Natl. Acad. Sci. U.S.A., 83: 7721–7725, 1986), cathepsin L (Gal, S., et al., Biochem. J., 253: 303–306, 1988), cathepsin H (Ritonja, A., et al., FEBS Lett., 228: 341–345, 1988), cathepsin S (Shi, G. P., et al., J. Biol. Chem., 267: 7258–7262, 1992), cathepsin C (Paris, A., et al., FEBS Lett., 369: 326–330, 1995), cathepsin O (Velasco, G., et al., J. Biol. Chem., 269: 27136–27142, 1994), cathepsin K (Inaoka, T., et al., Biochem. Biophys. Res. Commun., 206: 89–96, 1995) and cathepsin W (Linnevers, C., et al., FEBS Lett., 405: 253–259, 1997).

Furthermore, several groups have described the existence of additional cysteine proteinases including cathepsins S, M, N, P, and T, which were originally identified because of their degrading activity on specific substrates such as aldolase, collagen, proinsulin, or tyrosine aminotransferase, but whose characterization at the molecular level has not yet been reported (Pontremoli, S., et al., Arch. Biochem. Biophys., 214: 376–385, 1982; Maciewicz, R., et al., Biochem. J., 25: 433–440, 1988; Docherty, K., et al., Proc. Natl. Acad. Sci. U.S.A., 79: 4613–4617, 1982; Gohda, E., et al., J. Biol. Chem., 256: 2567–2572, 1981).

Structural comparisons between the different members of the cysteine proteinase family have shown that they are synthesized as preproenzymes, which are processed to the corresponding proenzymes and targeted to the lysosomes by the mannose 6-phosphate signal attached to them. However, in some cases, the precursors of these lysosomal enzymes escape from this processing pathway and continue along the secretory route, entering storage granules and finally being released into the extracellular space (Sloane, B. F., et al., Science, 212: 1151–1153, 1981). Amino acid sequence comparisons between all members of the family have revealed that they are not closely related; the percentage of identity between them is less than 50%. Nevertheless, in their amino acid sequences, all of them contain a series of amino acids that are absolutely conserved and essential for their catalytic activity (Berti, P. J., et al., J. Mol. Biol., 246: 273–283, 1995).

Because it seems clear that cysteine proteinases play essential roles in both normal and pathological conditions, including tumor processes, over the last few years, the possibility that additional, uncharacterized members of this family of proteolytic enzymes could be produced by human tumors has been examined. This search for new human cysteine proteinases led us to identify cathepsin O, which was originally cloned from a breast carcinoma but is widely distributed in human tissues (Velasco, G., et al., J. Biol. Chem., 269: 27136–27142, 1994). Furthermore, the cloning and characterization of human bleomycin hydrolase, a cytosolic cysteine proteinase that is distantly related to other members of the papain family and is involved in chemotherapy resistance, has recently been reported (Ferrando, A. A., et al., Cancer Res., 56: 1746–1750, 1996.).

SUMMARY OF THE INVENTION

It would be expected that the cysteine proteinases are not only involved in many normal cellular processes, including the turnover of intracellular proteins, prohormone activation, and bone remodeling but also play important roles in a number of diseases, disorders and pathological conditions such as Alzheimer's disease, pulmonary emphysema, rheumatoid arthritis, muscular dystrophy, osteoporosis, neuronal degenerative disease and cancer invasion and metastasis. Accordingly, it would be important to identify and isolate a novel cysteine proteinase, followed by elucidating the function of said cysteine proteinase involved in various diseases and disorders, especially cancers in view of not only elucidation of critical mechanism leading to such diseases and disorders but also researches and developments of therapy and therapeutic drugs thereagainst.

The present inventors have taken a view that, in the cysteine proteinase family, there will be novel members which have not been reported yet. The present inventors have carried out various studies by means of genetic engineering techniques. As a result, they have succeeded in cloning a human gene coding for a novel cysteine proteinase member and have disclosed all of its gene nucleotide sequence and amino acid sequence whereupon the present invention has been accomplished. When the putative amino acid sequence of the isolated novel cysteine proteinase was compared with the sequences of the already-reported cathepsins, it was noted that it has 78% homology to cathepsin L and not more than 40% homology to other cathepsins, respectively. From this characteristic feature in the amino acid sequence, said novel member was named "cathepsin L2".

Accordingly, the present invention provides novel proteins having cathepsin L2 activity, of which origin is human, in particular, polypeptides (or proteins) called "cathepsin L2" herein, processes for producing the same and use thereof, genes (or polynucleotides or nucleic acids) coding for said proteins, applications thereof, etc.

The present invention provides probes for hybridization, specific to cathepsin L2 genes. Further, the present invention provides antibodies specifically reactive to cathepsin L2, methods for immunologically assaying cathepsin L2 which comprises using said antibody, and assay kits therefor.

The present invention relates to novel human cathepsin L2 genes, to cathepsin L2 proteins which originated from human, and to analogues thereof. The present invention also relates to novel DNA sequences coding for all or part of said human cathepsin L2, to vectors comprising such DNA sequences, and to host cells transformed or transfected with such vectors. Further, the present invention encompasses processes for producing recombinant human cathepsin L2 and uses thereof. The present invention also relates to nucleic acids, such as DNA and RNA probes, hybridizable to human cathepsin L2 genes. The present invention further relates to antibodies, particularly monoclonal antibodies, which bind to human cathepsin L2, and to hybridomas which produce said antibodies. The present invention provides reagents for detecting and/or assaying human cathepsin L2, which comprise said products, and methods for detecting and/or assaying human cathepsin L2, which comprise using said reagents.

The present invention provides human cathepsin L2 agonists. Among them, more desired agonists are cathepsin L2 pseudomolecules which bind with cathepsin L2 binding molecules or cathepsin L2 receptor molecules and/or either produce or enhance cathepsin L2 inductive actions, and the like. Preferred agonists are also molecules which interact with cathepsin L2, cathepsin L2 polypeptides, or other regulating substances for cathepsin L2 activity to either enable or strengthen cathepsin L2 actions and effects or more.

The present invention provides human cathepsin L2 antagonists. Among them, more desired antagonists are cathepsin L2 pseudomolecules which bind with cathepsin L2 binding molecules or cathepsin L2 receptor molecules but do not produce one or more cathepsin L2 inductive actions, or which inhibit such actions, and the like. Preferred antagonists are also molecules which interact with cathepsin L2, cathepsin L2 polypeptides, or other regulating substances for cathepsin L2 activity to either inhibit or suppress one or more cathepsin L2 actions and effects.

The present invention further provides methods for detecting not only substances which inhibit a cysteine proteinase activity associated with human cathepsin L2 but also substances which inhibit a proteolytic activity associated therewith. The present invention thus relates to drugs comprising such substances or derivatives thereof as effective components, for example, neutralizing antibodies which inhibit its cysteine proteinase activity or proteolytic activity, and specifically to monoclonal antibodies which bind with human cathepsin L2. Further, the present invention relates to peptide fragments of human cathepsin L2 and derivatives thereof or a salt thereof, which bind with anti-human cathepsin L2 antibodies but have no human cathepsin L2 activity. The present invention relates to antisense nucleotide and derivatives thereof which inhibits human cathepsin L2 expression, and to agents which comprise the same as an active component.

The present invention provides:
(1) a novel protein or a salt thereof, which
    (A) belongs to a member of cathepsins derived from human; and
    (B) is (i) human cathepsin L2 protein or (ii) any of those having at least 80% homology to an amino acid sequence of said human cathepsin L2 protein and possessing (a) a cysteine proteinase activity or (b) an antigenicity substantially equivalent to said human cathepsin L2 protein;
(2) a protein or a salt thereof, which has an amino acid sequence selected from the group consisting of
    (a) amino acid residues 114 to 334,
    (b) amino acid residues 18 to 334, and
    (c) amino acid residues 1 to 334, of SEQ ID NO: 1 in the Sequence Listing, and
    (d) substantially equivalent amino acid sequences thereto;
(3) a peptide fragment of the protein according to above (1) or (2), or a salt thereof;
(4) a nucleic acid comprising a nucleotide sequence coding for the protein according to above (1) or (2);
(5) the nucleic acid according to above (4), having (i) an open reading frame region of the nucleotide sequence of SEQ ID NO: 2 in the Sequence Listing or (ii) a substantially equivalent thereto;
(6) a vector comprising the nucleic acid according to above (4) or (5);
(7) a transformant or transfectant harboring (i) the nucleic acid according to above (4) or (5) or (ii) the vector according to above (6);
(8) the transformant or transfectant according to above (7), wherein a host cell for the nucleic acid or vector is selected from the group consisting of *Escherichia coli*, yeast, CHO cell, and COS cell;
(9) the protein according to above (1) or (2), which is a product obtained from the transformant or transfectant according to above (8);
(10) a probe for hybridization to human cathepsin L2 gene, comprising all or part of the nucleotide sequence of SEQ ID NO: 2;
(11) the probe according to above (10), comprising a untranslation region of the nucleotide sequence of SEQ ID NO: 2;
(12) an antibody against
    (i) the protein or a salt thereof according to above (1);
    (ii) the protein or a salt thereof according to above (2); or
    (iii) the peptide fragment or a salt thereof according to above (3);
(13) an immunological assay for detecting and/or measuring the protein or a salt thereof according to above (1) or (2), which comprises using, as a reagent, a monoclonal antibody specifically immunoreactive with the protein or a salt thereof according to above (1) or (2);

(14) an immunological assay agent for detecting and/or measuring the protein or a salt thereof according to above (1) or (2), which comprises a monoclonal antibody specifically immunoreactive with the protein or a salt thereof according to above (1) or (2);

(15) a pharmaceutical composition comprising (i) the protein or peptide fragment or a salt thereof according to any of above (1) to (3); (ii) the nucleic acid according to above (4) or (5); or (iii) the antibody according to above (12);

(16) a pharmaceutical composition comprising a compound which enhances or inhibits a biological activity of the protein or peptide fragment or a salt thereof according to any of above (1) to (3), or a salt thereof; and

(17) a screening method or screening kit for a compound which enhances or inhibits the biological activity of the protein or peptide fragment or a salt thereof according to any of above (1) to (3), or a salt thereof.

In another aspect, the present invention provides:

(18) the protein or a salt thereof according to above (1), wherein the protein (1) is native human cathepsin L2 or a salt thereof, or (2) has a cysteine proteinase activity or antigenicity, or primary structural conformation identical with or substantially equivalent to that of native human cathepsin L2, or a segment thereof;

(19) the protein or a salt thereof according to above (1), wherein the protein is at least 80% homologous, preferably 85% or more homologous, or more preferably 90% or more homologous, to an amino acid sequence selected from the group consisting of
  (a) amino acid residues 114 to 334,
  (b) amino acid residues 18 to 334, and
  (c) amino acid residues 1 to 334, of SEQ ID NO: 1 in the Sequence Listing, or a segment thereof;

(20) the protein or a salt thereof according to above (1), wherein the protein is
  (i) a human cathepsin L2 protein having an amino acid sequence selected from the group consisting of
    (a) amino acid residues 114 to 334,
    (b) amino acid residues 18 to 334, and
    (c) amino acid residues 1 to 334, of SEQ ID NO: 1 in the Sequence Listing, or
  (ii) a member selected from the group consisting of
    (d) deletion analogues wherein one or more amino acid residues (for example, 1 to 73 residues, preferably 1 to 60 residues, more preferably 1 to 40 residues, further more preferably 1 to 20 residues, particularly 1 to 10 residues, etc.) characteristic of human cathepsin L2 are deleted,
    (e) substitution analogues wherein one or more amino acid residues (for example, 1 to 73 residues, preferably 1 to 60 residues, more preferably 1 to 40 residues, further more preferably 1 to 20 residues, particularly 1 to 10 residues, etc.) characteristic of human cathepsin L2 are replaced with other amino acid residues, and
    (f) addition analogues wherein one or more amino acid residues (for example, 1 to 80 residues, preferably 1 to 60 residues, more preferably 1 to 40 residues, further more preferably 1 to 20 residues, particularly 1 to 10 residues, etc.) are inserted, or a segment thereof;

(21) a nucleic acid comprising a nucleotide sequence coding for the protein according to any of above (18) to (20);

(22) a nucleic acid comprising a region selected from the group consisting of
  (a) sequences having at least 79% homology to human cDNA of GENBANK™/EMBL accession number: Y14734,
  (b) sequences having at least 80% homology to human cDNA of GENBANK™/EMBL accession number: Y14734,
  (c) sequences having at least 85% homology to human cDNA of GENBANK™/EMBL accession number: Y14734,
  (d) sequences having at least 90% homology to human cDNA of GENBANK™/EMBL accession number: Y14734,
  (e) sequences having at least 95% homology to human cDNA of GENBANK™/EMBL accession number: Y14734,
  (f) sequences having at least 97% homology to human cDNA of GENBANK™/EMBL accession number: Y14734,
  (g) sequences having at least 98% homology to human cDNA of GENBANK™/EMBL accession number: Y14734, and
  (h) sequences having at least 99% homology to human cDNA of GENBANK™/EMBL accession number: Y14734;

(23) a nucleic acid comprising a region selected from the group consisting of
  (a) sequences having at least 79% homology to human cDNA of microorganism deposit NIBH accession No. FERM BP-6640, or human cDNA in recombinant plasmid pGEX-3X CathL2 harbored in microorganism deposit NIBH accession No. FERM BP-6641,
  (b) sequences having at least 80% homology to said human cDNA,
  (c) sequences having at least 85% homology to said human cDNA,
  (d) sequences having at least 90% homology to said human cDNA,
  (e) sequences having at least 95% homology to said human cDNA,
  (f) sequences having at least 97% homology to said human cDNA,
  (g) sequences having at least 98% homology to said human cDNA, and
  (h) sequences having at least 99% homology to said human cDNA;

(24) a nucleic acid comprising a region selected from the group consisting of
  (a) sequences having at least 79% homology to the nucleotide sequence of SEQ ID NO: 2 in the Sequence Listing,
  (b) sequences having at least 80% homology to the nucleotide sequence of SEQ ID NO: 2,
  (c) sequences having at least 85% homology to the nucleotide sequence of SEQ ID NO: 2,
  (d) sequences having at least 90% homology to the nucleotide sequence of SEQ ID NO: 2,
  (e) sequences having at least 95% homology to the nucleotide sequence of SEQ ID NO: 2,
  (f) sequences having at least 97% homology to the nucleotide sequence of SEQ ID NO: 2,
  (g) sequences having at least 98% homology to the nucleotide sequence of SEQ ID NO: 2, and (h) sequences having at least 99% homology to the nucleotide sequence of SEQ ID NO: 2;

(25) a vector comprising the nucleic acid according to any of above (21) to (24);

(26) a transformant or transfectant harboring (i) the nucleic acid according to any of above (21) to (24) or (ii) the vector according to above (25);

(27) the transformant or transfectant according to above (26), wherein a host cell for the nucleic acid or vector is selected from the group consisting of *Escherichia coli*, yeast, CHO cell, and COS cell;

(28) the protein according to any of above (18) to (20), which is a product obtained from the transformant or transfectant according to above (27);

(29) a labeled or non-labeled probe for hybridization, comprising a nucleotide sequence hybridizable with a human cathepsin L2 gene but not hybridizing to a human cathepsin L gene, under high-stringency conditions, wherein the nucleotide sequence has at least part of the nucleotide sequence of SEQ ID NO: 2 in the Sequence Listing;

(30) a method for assaying a nucleic acid encoding human cathepsin L2 in a sample, which comprises the steps of
  (i) hybridizing a probe specific to the human cathepsin L2-coding nucleic acid with the sample under conditions effective for specific hybridization with said nucleic acid to form a hybrid, and
  (ii) assaying the hybridization of said probe with the sample nucleic acid,
wherein said probe comprises a segment with 10 or more base pairs, said segment which is at least 79% homologous to the nucleotide sequence of SEQ ID NO: 2 in the Sequence Listing;

(31) the antibody according to above (12), which is a monoclonal antibody immobilized on a solid phase;

(32) the antibody according to above (12), which is a labeled monoclonal antibody;

(33) the antibody according to above (12), which is labeled with an enzyme;

(34) the antibody according to above (12), which is labeled Fab' derived from a monoclonal antibody;

(35) a method for inhibiting the biological activity (e.g., cysteine proteinase activity, antigenicity, etc.) of the protein according to above (1) or (2); and

(36) the method according to above (35), wherein the inhibitor is selected from the group consisting of peptides, proteins, nonpeptide compounds, synthetic compounds, fermented products, cell extracts, plant extracts, animal tissue extracts, and antibodies such as monoclonal antibodies.

In yet another aspect, the present invention provides:

(37) a screening method for a compound capable of enhancing or inhibiting the biological activity of the protein according to any of above (1) to (3) and (18) to (20), a peptide fragment thereof, or a salt thereof, which comprises using, as a tool, a member selected from the group consisting of the proteins according to any of above (1) to (3) and (18) to (20), peptide fragments thereof, and salts thereof;

(38) a screening method for a compound which enhances or inhibits the biological activity of the protein according to any of above (1) to (3) and (18) to (20), a peptide fragment thereof, or a salt thereof, which comprises comparing (i) a first measurement wherein a substrate is contacted with a member selected from the group consisting of the proteins according to any of above (1) to (3) and (18) to (20), peptide fragments thereof, and salts thereof, with (ii) a second measurement wherein the substrate and a test compound are contacted with said member;

(39) a screening kit for a compound capable of enhancing or inhibiting the biological activity of the protein according to any of above (1) to (3) and (18) to (20), a peptide fragment thereof, or a salt thereof, which comprises a member selected from the group consisting of the proteins according to any of above (1) to (3) and (18) to (20), peptide fragments thereof, and salts thereof;

(40) a compound or a salt thereof, capable of enhancing or inhibiting the biological activity of the protein according to any of above (1) to (3) and (18) to (20), a peptide fragment thereof, or a salt thereof, which is obtained or identified (i) by the screening method according to above (17), (37) or (38) or (ii) via using the screening kit according to above (17) or (39); and

(41) a pharmaceutical composition comprising an effective amount of a compound or a salt thereof which enhances or inhibits the biological activity of the protein according to any of above (1) to (3) and (18) to (20), a peptide fragment thereof, or a salt thereof, said compound being obtained or identified (i) by the screening method according to above (17), (37) or (38) or (ii) via using the screening kit according to above (17) or (39).

In a further aspect, the present invention provides:

(42) an immunological assay for the protein or a salt thereof according to above (1), which comprises using, as an assay agent, a monoclonal antibody which specifically immunoreacts with the protein or a salt thereof according to above (1);

(43) an immunological assay agent for the protein or a salt thereof according to above (1), which comprises a monoclonal antibody which specifically immunoreacts with the protein or a salt thereof according to above (1);

(44) the assay method according to above (13), wherein the antibodies according to above (12) are employed, said antibodies comprising at least 2 members composed of both (i) an antibody immobilized on a solid phase and (ii) a labeled antibody;

(45) the assay method according to above (44), wherein the protein or a salt thereof according to above (1) is quantitatively measured;

(46) the assay method according to above (44) or (45), wherein a sample or specimen to be assayed is selected from the group consisting of blood, serum, plasma, articular fluid, urine, saliva, cerebrospinal fluid, amniotic fluid, tissue extracts, tissue culture extracts, cell culture supernatants;

(47) an assay reagent set for detecting and/or assaying human cathepsin L2, which comprises at least 2 members composed of both (i) a reagent comprising an antibody immobilized on a solid phase and (ii) a reagent comprising a labeled antibody, said antibodies each being selected from the antibodies according to above (12) and said assay reagent set being used in the immunological assay according to any of above (44) to (46);

(48) a hybridoma producing a monoclonal antibody against a member selected from the group consisting of (a) the proteins according to above (1) and salts thereof, and (b) peptide fragments thereof and salts thereof, said hybridoma being generated by cell fusion of (i) a spleen cell obtained from an animal, such as a mouse, immunized with said member with (ii) an immortal cell, such as a myeloma cell, derived from an animal, such as a mouse; and

(49) a process for producing the hybridoma according to above (48), which comprises:

fusing a spleen cell obtained from an animal, such as a mouse, immunized with a member selected from the group consisting of (a) the proteins according to above (1) and salts thereof, and (b) peptide fragments thereof and salts thereof, with an immortal cell, such as a myeloma cell, derived from an animal such as a mouse, and selecting a hybridoma cell capable of producing a monoclonal antibody against said member;

In a still further aspect, the present invention provides:

(50) a nucleic acid containing a nucleotide sequence hybridizing with the nucleotide sequence of SEQ ID NO: 2 under stringent conditions;

(51) a vector containing the nucleic acid according to above (50);

(52) a transformant or transfectant comprising the vector according to above (51);

(53) a protein or a salt thereof, which is a product generated as a consequence of gene expression by the transformant or transfectant according to above (52);

(54) the nucleic acid according to any of above (4), (5), (21) to (24) and (50), wherein the nucleic acid is DNA.

(55) a process for preparation of a product selected from the group consisting of (a) the proteins according to above (1) and salts thereof, and (b) peptide fragments thereof and salts thereof, which comprises:

culturing the transformant or transfectant according to above (7), (8), (26), (27) or (52) to produce and accumulate said product, and collecting or isolating said product;

(56) a compound or a salt thereof enhancing the biological activity of the protein according to any of above (1) to (3), a peptide fragment thereof or a salt thereof, which is a product obtained or identified as a consequence of application of (i) the screening method according to any of above (17), (37) or (38) or (ii) the screening kit according to above (17) or (39);

(57) a compound or a salt thereof inhibiting the biological activity of the protein according to any of above (1) to (3), a peptide fragment thereof or a salt thereof, which is a product obtained or identified as a consequence of application of (i) the screening method according to any of above (17), (37) or (38) or (ii) the screening kit according to above (17) or (39);

(58) the screening method according to above (17), wherein the biological activity of above (17) is of proteinase activity;

(59) the screening kit according to above (17), wherein the biological activity of above (17) is of proteinase activity;

(60) the compound or a salt thereof according to above (40), wherein the biological activity of above (40) is of proteinase activity;

(61) the pharmaceutical composition according to above (16), wherein the biological activity of above (16) is of proteinase activity;

(62) a method for quantitative assay of the protein according to any of above (1) to (3), a peptide fragment thereof or a salt thereof in a sample to be assayed, which comprises:

reacting competitively the antibody according to above (12) with the sample in the presence of a labeled protein according to any of above (1) to (3), a labeled peptide fragment thereof or a salt thereof, and measuring the amount rate of said labeled protein (or said labeled peptide fragment) or a salt thereof, bound to said antibody; and

(63) a method for quantitative assay of the protein according to any of above (1) to (3), a peptide fragment thereof or a salt thereof in a sample to be assayed, which comprises:

reacting an antibody immobilized on a solid phase according to above (12) with the sample in the presence of a labeled protein according to any of above (1) to (3), a labeled peptide fragment thereof or a salt thereof, and measuring either the amount of labels immobilized on said solid phase or the amount of labels not binding to said solid phase.

The above objects and other objects, features, advantages, and aspects of the present invention are readily apparent to those skilled in the art from the following detailed description of preferred embodiments. It should be understood, however, that the description of the specification including the following detailed description of preferred embodiments, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

The term "and/or" used herein means the presence of both (1) a jointly connecting relation and (2) a selectively connecting relation. For example, in the case of "therapeutic and/or prophylactic", it is used in such a sense that said expression covers both (1) "therapeutic and prophylactic" and (2) "therapeutic or prophylactic". In other cases, the term "and/or" is used in the same sense that it covers both (1) a jointly connecting relation and (2) a selectively connecting relation as well.

BRIEF DESCRIPTION OF THE DRAWINGS

FIGS. 1(A) and 1(B) show a nucleotide sequence (SEQ ID NO. 15) and deduced amino acid sequence (SEQ ID NO. 1) of human cathepsin L2 cloned from a brain cDNA library. Arrows indicate the putative cleavage sites between the signal sequence and the propeptide as well as between the propeptide and the mature enzyme.

FIGS. 2(A), 2(B) and 2(C) show a multiple amino acid sequence alignment of cathepsin L2 with other human cysteine proteinases (SEQ ID NOS: 17-25). The amino acid sequences of previously known human cysteine proteinases were extracted from the SwissProt database, and multiple alignment was performed with the PILEUP program from the Genetics Computer Group package. Numbering corresponds to the sequence of cathepsin L2. The NH$_2$-terminal extension characteristic of cathepsin C has not been included in the multiple alignment. *(asterisk) residues that are common to all sequences. Common residues between any human cathepsin and cathepsin L2 are underlined. Gaps are indicated by dots. An arrow indicates the putative cleavage site between the propeptide and the mature enzyme.

DETAILED DESCRIPTION OF THE PREFERRED EMBODIMENTS

Figure 3A:
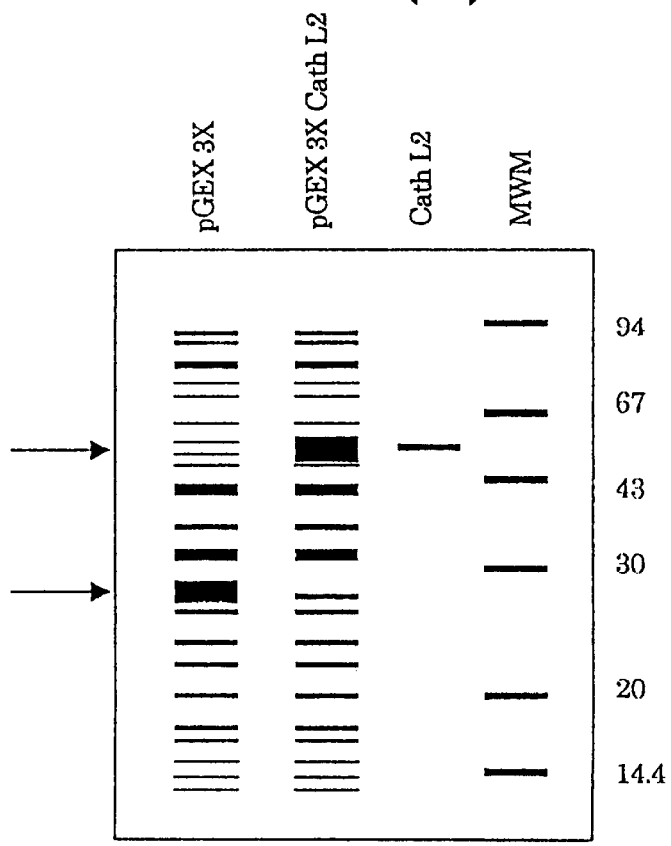
FIGS. 3(A) and 3(B) show purification and enzymatic analysis of recombinant, cathepsin L2 expressed in E. coli.

The present invention provides proteins or a salt thereof which (1) are species of cathepsin L2 protein derived from human being which is a member of the papain family and has a cysteine proteinase activity, or (2) have (a) at least 80% homology to the amino acid sequence of said cathepsin L2 and (b) a cysteine proteinase activity or an antigenicity equivalent thereto; characteristic peptide fragments of said protein or a salt thereof; genes (e.g., DNA and RNA) coding therefor; vectors or plasmids containing said genes in such a manner that they can be operated by genetic recombinant techniques; host cells which are transformed with such vectors, etc.; transgenic animals expressing said genes, such as transgenic mice; knockout animals (e.g., knockout mice, etc.) where said gene is specifically inactivated; methods for the manufacture of said proteins or a salt thereof by culturing said transformed or transfected cells; antibodies (particularly monoclonal antibodies) obtained by the use of (i) said proteins or a salt thereof thus obtained or (ii) the characteristic peptide fragments of said protein or a salt thereof; hybridoma cells which produce said antibodies; and (a) assaying and diagnosing means and (b) reagents or agents, which comprise using said isolated gene such as DNA and RNA as a probe or using said antibody. The present invention further provides utilization of the active components disclosed and mentioned in the present specification, such as pharmaceutical compositions or assay agents containing one or more said active components, therapeutic or prophylactic methods for diseases, disorders or pathological conditions which comprise the application of one or more said active components and screening methods or assays which comprise using one or more said active components.

In an embodiment, the human cathepsin L2 includes all substances comprising an amino acid sequence with amino acid residues 114 to 334 in SEQ ID NO: 1, substances comprising an amino acid sequence with amino acid residues 18 to 334 in SEQ ID NO: 1, substances comprising an amino acid sequence with amino acid residues 1 to 334 in SEQ ID NO: 1, and all substances (i) comprising an amino acid sequence with more than 78% homology, preferably 79% or more homology, still preferably 80% or more homology, further preferably 85% or more homology, more preferably 90% or more homology, still more preferably 95% or more homology, and most preferably 97% or more homology to any of the aforementioned sequences and (ii) having a substantially identical or equivalent biological activity, such as a cysteine proteinase activity or an equivalent antigenicity. The human cathepsin L2 may be any substances as long as they are members of the papain family with a cysteine proteinase activity and have a novel amino acid sequence. Preferably, the present invention provides a human-derived cathepsin L2 protein or a salt thereof selected from the group consisting of substances having an amino acid sequence with amino acid residues 114 to 334 in SEQ ID NO: 1, substances having an amino acid sequence with amino acid residues 18 to 334 in SEQ ID NO: 1, substances having an amino acid sequence with amino acid residues 1 to 334 in SEQ ID NO: 1, and substances having an amino acid sequence substantially equivalent to any of the aforementioned substances. The present human cathepsin L2 may also have part or all of the amino acid sequence set forth in SEQ ID NO: 1. All substances having such sequences may be included in the present invention.

In the present specification, the term "homology" or "homologous" means the quantity (or number), in terms of identity, which can be obtained by determining that corresponding amino acid residues or corresponding bases are matched with each other between two chains in polypeptide sequences (or amino acid sequences) or polynucleotide sequences (or base sequences) when amino acid residues or bases constituting the chain are compared with one another between the two chains and it also means the degree of sequence correlation in terms of similarity between two polypeptide sequences or two polynucleotide sequences. The homology can be easily calculated. Various methods for measuring the homology between two polynucleotide sequences or polypeptide sequences have been known and the term "homology" (sometimes called "identity") has been well known to the persons skilled in the art (for example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991), etc.). General techniques for determining the homology between two strands include those disclosed in Martin, J. Bishop (Ed.), Guide to Huge Computers, Academic Press, San Diego, (1994); Carillo, H. & Lipman, D., SIAM J. Applied Math., 48: 1073 (1988), etc., but are not limited thereto. Preferred methods for measuring the homology include those which are designed so as to obtain the part of the highest fitting relation between the two sequences tested. An example of such methods is a technique which is constructed as a computer program. Preferred computer programming methods include a GCG program package (Devereux, J. et al., Nucleic Acids Research, 12(1): 387 (1984)), BLASTP, BLASTN, FASTA (Atschul, S. F. et al., J. Molec. Biol., 215:

403 (1990)), etc., but are not limited thereto. For such methods, methods known in the art may be employed.

The human cathepsin L2 can be encoded by a gene comprising typically the nucleotide sequence set forth in SEQ ID NO: 2 in the Sequence Listing, a nucleotide sequence comprising a region ranging between ATG from the 70th to 72nd nucleotide residues of SEQ ID NO: 2 in the Sequence Listing and TGA from the 1072nd to 1074th nucleotide residues (termination codon: TGA from the 1072nd to 1074th nucleotide residues may be replaced with TAA or TAC). The human cathepsin L2-encoding genes may also include those comprising a nucleotide sequence ranging from the 409th to 1074th nucleotide residues of SEQ ID NO: 2 in the Sequence Listing, those comprising a nucleotide sequence ranging from the 121st to 1074th nucleotide residues of SEQ ID NO: 2 in the Sequence Listing, those in which an initiation codon, such as a codon coding for Met, is added to the sequence. Further, the cathepsin L2-encoding genes are any substances as long as they contain a nucleotide sequence equivalently effective, for example, in coding for proteins having (i) an amino acid sequence 80% or more homologous to any of proteins encoded by said nucleotide sequences and (ii) a substantially identical or equivalent biological activity, such as a cysteine proteinase activity or an equivalent antigenicity. The human cathepsin L2-encoding genes are nucleic acids including single- and double-stranded DNA, RNA, DNA:RNA hybrids, and synthetic DNA, and may be any of human genome DNA, human genomic DNA libraries, human tissue/cell-derived cDNA, and synthetic DNA. The human cathepsin L2 nucleotide sequences can be modified (by addition, deletion, substitution, etc.), and those thus modified may be included herein. Further, as described herein below, the instant nucleic acids may include those encoding the proteins or a fragment thereof and are preferably DNA. The terms "nucleotide sequence equivalently effective" and "equivalent nucleotide sequence" refer to those which hybridize with the nucleotide sequence of SEQ ID NO: 2 in the Sequence Listing, for example, under stringent conditions, those which encode an amino acid sequence substantially equivalent to human cathepsin L2, etc.

The DNA containing a nucleotide sequence represented by SEQ ID NO: 2 or an equivalent thereof according to the present invention may be cloned and obtained, for example, by the following techniques:

It should be noted that genetic recombination techniques may be conducted, for example, by the methods disclosed in J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vol. 1 to 4, (The Practical Approach Series), IRL Press, Oxford University Press (1995); Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", Tokyo Kagaku Dojin, Japan (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); J. H. Miller ed., "Methods in Enzymology", Vol. 204, Academic Press, New York (1991); R. Wu et al. ed., "Methods in Enzymology", Vol. 218, Academic Press, New York (1993), etc. as well as by techniques disclosed in the references cited therein, the disclosures of which are hereby incorporated by reference, or by the substantially same techniques as they disclose or modified techniques thereof. Such techniques and means may also be those which are individually modified/improved from conventional techniques depending upon the object of the present invention.

Firstly, searching of a gene database is conducted for sequences with homology to amino acid sequences previously determined for the known human cysteine proteinase family (more preferably, the papain family and, particularly preferably, human cathepsins) where their entire sequence or partial sequence is cloned, thereby identifying a sequence which shows a significant similarity thereto. The sequence showing a significant similarity thereto includes preferably cDNA sequences derived from animals and, more preferably, cDNA sequences derived from human. Depending upon the sequence which is identified as such, suitable primers are designed and synthesized. The desired sequence is obtained by a PCR amplification using cDNA libraries, preferably derived from the animal which is an origin of the identified sequence. The resulting DNA fragments are used as probes for screening human genomic DNA libraries constructed from various human tissues or cultured cells, or human cDNA libraries. The clones which hybridize to the probe are selected and inserts in the clones are sequenced to analyze their nucleotide sequences, thereby determining DNA fragments having a novel human cysteine proteinase gene sequence and isolating the same. If necessary, the DNA inserts in said clones may be subjected to subcloning. Sequencing of nucleotide sequences may be carried out by a dideoxy method (such as an M13 dideoxy method), a Maxam-Gilbert method, etc. or may be carried out using a commercially available sequencing kit such as a Taq dyeprimer cycle sequencing kit and a Sequenase v 2.0 kit or an automated nucleotide sequencer such as a fluorescent DNA sequencer. Polymerases used in the dideoxy methods include, for example, Klenow fragment derived from DNA polymerase I, AMV reverse transcriptase, Taq DNA polymerase, T7 DNA polymerase, modified T7 DNA polymerase, etc.

Based on the analyzed DNA sequence in which the novel member of human cysteine proteinase genes is prospected to be contained, genes encoding said human cysteine proteinase are cloned and isolated.

Sense primers and antisense primers are first synthesized, relying on the DNA sequence in which the novel human cysteine proteinase gene member thus analyzed is presumed to be included. The synthesis of primers is conducted by techniques well known in the art, including a phosphodiester method, a phosphotriester method, a phosphoramidite method, etc., with an automated DNA synthesizer. Polymerase chain reaction (PCR) is performed using cDNA libraries in combination with sense primers and antisense primers as aforementioned, for cDNA amplification. The cDNA library used for the cDNA amplification includes those derived from various human tissues and cultured cells (especially, human tissues and cells including human brain, thymus, testis, intestine and kidney; breast carcinomas; breast cancer cell lines such as ZR-75-1, Hs-578T, and MDA-MB435; ovary cancers; colorectal adenocarcinoma SW480; etc.). Acquisition of said gene can be achieved via preparation of specific probes for hybridization from the clone identified as aforementioned, screening of human-derived DNA libraries, and selection of clones hybridizing with the probe. The CDNA library used as a template herein includes those as prepared hereinbelow, or various commercial cDNA libraries derived from tissues, such as cDNA libraries commercially available from Stratagene, Invitrogen, Clontech, etc.

The term "polymerase chain reaction" or "PCR" used herein usually refers to techniques described in U.S. Pat. No. 4,683,195. For example, the PCR is an in vitro method for the enzymatic amplification of desired specific nucleotide sequences. The PCR generally includes repetitive series of cycles wherein a primer elongation synthesis is conducted using two oligonucleotide primers which are able to preferentially hybridize with a template nucleic acid. Typically, the primers used in PCR may include those which are complimentary to the internal nucleotide sequence of interest in the template. For example, primer pairs which are complementary to both ends of said nucleotide sequence to be amplified or flanking regions adjacent to said nucleotide sequence to be amplified may be preferably used. The PCR may be carried out by techniques known in the art or by methods substantially equivalent thereto or modified techniques. The reaction may be conducted by the methods as disclosed, for example, in R. Saiki, et al., Science, 230: 1350, 1985; R. Saiki, et al., Science, 239: 487, 1988; H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995); M. A. Innis et al. ed., "PCR Protocols: a guide to methods and applications", Academic Press, New York (1990)); M. J. McPherson, P. Quirke and G. R. Taylor (Ed.), PCR: a practical approach, IRL Press, Oxford (1991); M. A. Frohman et al., Proc. Natl. Acad. Sci. USA, 85, 8998–9002 (1988); etc., the disclosures of which are hereby incorporated by reference, or by techniques derived by modification or alteration of the methods as described in the above documents. The PCR can also be conducted using a commercially available kit suitable therefor according to protocols as disclosed by a kit manufacturer or distributor.

The term "oligonucleotide(s)" used herein refers to a relatively short single-stranded polynucleotide or double-stranded polynucleotides or, preferably, polydeoxynucleotide(s). They can be chemically synthesized by known methods as disclosed in Angew. Chem. Int. Ed. Engl., Vol. 28, pages 716 to 734 (1989), including a triester method, a phosphite method, a phosphoramidite method and a phosphonate method. It has been known that synthesis can be conveniently carried out usually on a modified solid support. For example, the synthesis may be conducted using an automated synthesizer and such a synthesizer is commercially available. Said oligonucleotide may contain one or more modified base(s) and, for example, it may contain a base which is not common in nature such as inosine or a tritylated base.

The resultant PCR products can be cloned and sequenced. As a result, DNA fragments having a novel human cysteine proteinase gene sequence can be isolated and characterized. Further, various cDNA libraries can be screened by using as a probe this DNA fragment similarly to isolate and identify target DNA. For cloning of the PCR products, commercially available plasmid vectors such as p-DIRECT™ (Clontech), pCR-SCRIPT™ SK(+) (Stratagene), pGEM-T (Promega), and pAMP™ (Gibco-BRL) can be employed.

In order to isolate the novel full-length human cysteine proteinase gene sequence containing an entire open reading frame, as required, cDNA libraries constructed from various human tissues or culture cells as mentioned hereinabove are screened optionally using, as a probe, the above-mentioned DNA fragment of which the novel cysteine proteinase gene is composed (this DNA fragment is isolated via the above-mentioned techniques) and clones hybridizing the probe are selected. cDNA inserts in the selected and isolated clone are then sequenced. As a result, the novel DNA fragment constituting said novel cysteine proteinase gene is isolated, characterized, and identified. It goes without saying that the cDNA insert in the clone can be optionally subcloned as required. Based on the sequenced nucleotides, it is possible to isolate and determine target DNAs. Preferably, human brain-derived cDNA libraries are screened, a detected DNA is sequenced, and the target DNA is isolated and identified. Labeling of probes, etc. with a radioisotope, etc., may be carried out using a commercially available labeling kit such as a random primed DNA labeling kit (Boehringer Mannheim).

In order to construct the CDNA libraries, CDNA is needed. The CDNA can be obtained, for example, by methods as described herein below.

mRNA samples can be isolated from various human tissues and culture cells (e.g., tissues and cells including human brain, thymus, testis, intestine and kidney; breast carcinomas; breast cancer cell lines such as ZR-75-1, Hs-578T, and MDA-MB435; ovary cancer; colorectal adenocarcinoma SW480; etc.) as listed herein above. Although, in an embodiment, mRNA may be isolated with a method known in the art or by the substantially same method as it is or modifications thereof, the isolation and purification of mRNA can be performed by methods disclosed in, for example, J. Sambrook et al.,"Molecular Cloning", 2nd ed., Chapter 7, Cold Spring Harbor Laboratory, Cold Spring Harbor, N.Y. (1989); D. M. Glover et al. ed., "DNA Cloning", 2nd ed., Vol. 1, (The Practical Approach Series), IRL Press, Oxford University Press (1995); L. Grossman et al. ed., "Methods in Enzymology", Vol. 12, Part A & B, Academic Press, New York (1968); S. L. Berger et al. ed., "Methods in Enzymology", Vol. 152, p.33 & p.215, Academic Press, New York (1987); Biochemistry, 18: 5294–5299, 1979; etc., the disclosures of which are hereby incorporated by reference. Examples of such mRNA isolating and purifying techniques are a guanidine-cesium chloride method, a guanidine thiocyanate method, a phenol method, etc. Kits for isolating the mRNA are those commercially available from Pharmacia, Stratagene, Gibco-BRL, etc. As required, the resulting total RNA may be subjected to a purification process using an oligo(dT)-cellulose column, a spin column, oligo(dT)-coupled magnetic beads, etc. to give poly(A)$^+$ mRNA.

cDNAs are prepared by using, as a template, the resulting mRNA and a reverse transcriptase (RNA dependent DNA polymerase), etc. Reverse transcription can be carried out with oligo(dT) primers. The oligo(dT) primer includes preferably those having 12 to 18 T residues. For directional cloning, it is also desirable to use synthetic oligonucleotide primers to which restriction sites are ligated at the 5'-side of 12 to 18 T residues thereof. Examples of such a primer include Xba I oligo(dT) primer-adaptors, etc. Use of random hexamer primers increases the possibility of obtaining a 5'-end side of mRNA. Such random hexamer primers can be employed alone or in a mixed form with oligo(dT) primers. As required, RNase inhibitors such as RNasin (Boehringer Mannheim) may be optionally added in the reverse transcription. The reverse transcriptase synthesis of cDNA using mRNA may be carried out by standard techniques known in the art, by the substantially same techniques or by modified techniques thereof. Detailed techniques are found in, for example, H. Land et al., Nucleic Acids Res., 9: 2251, 1981; U. Gubler et al., Gene, 25: 263–269, 1983; S. L. Berger et al. ed., "Methods in Enzymology", Vol. 152, p.307, Academic Press, New York (1987); etc., the disclosures of which are hereby incorporated by reference.

Then, based upon the cDNA thus prepared, cDNA libraries can be constructed using phage vectors, plasmid vectors, etc. Besides the technique using a phage vector, transformations of host cells including *Escherichia coli* may be conducted according to techniques known in the art, such as a calcium method, a rubidium/calcium method, a calcium/manganese method, a TFB high-efficiency method, a FSB frozen competent cell method, a rapid colony method, an electroporation method or the substantially same methods (D. Hanahan, J. Mol. Biol., Vol. 166, p. 557 (1983), etc.).

It is also possible to obtain genes coding for the human cathepsin L2 of the present invention by PCR using, as a template, the cDNA thus prepared, together with primers designed based upon the determined base sequence for novel DNA fragments constituting said novel human cysteine proteinase gene. In a typical case, degenerate primers are prepared based upon highly-conserved amino acid regions selected from amino acid sequences for known cysteine proteinase enzymes of the papain family where cloning of all or part of their sequence is done, more preferably, an amino acid sequence of human cathepsin L2 where the sequence is determined or presumed) or regions specifically existing in cathepsins. The highly-conserved amino acid regions include sequences of a cleavage site between a precursor (a pro-type form) thereof and an active form or sequences adjacent to the cleavage site, etc. The regions specifically existing in cathepsins include amino acid sequence fragments in the C-terminal region thereof, amino acid sequence fragments in regions located between a propeptide domain thereof and a catalytic domain, amino acid sequence fragments in the active site region of the catalytic domain, etc. PCR is carried out using the primers and the above-prepared cDNA. The PCR may be conducted in such a manner as aforementioned. It is also possible that the resulting PCR products are subjected to cloning and sequencing in the same manner as above, thereby determining nucleotide sequences for the resulting PCR products and identifying DNA fragments having the novel human cathepsin L2 gene sequence. It is further possible that said DNA fragments are used as probes for screening various cDNA libraries in the similar manner in order to isolate desired DNA.

Polymerase chain reaction coupled reverse transcription (hereinafter briefly referred to as "RT-PCR") and rapid amplification of cDNA ends (hereinafter briefly referred to as "RACE") can be adopted in order to isolate the target DNA. RACE can be carried out, for example, according to methods as disclosed in M. A. Innis et al. ed., "PCR Protocols" (M. A. Frohman, "a guide to methods and applications"), pp.28–38, Academic Press, New York (1990), etc. The RT-PCR products may be cloned into plasmid vectors and introduced into highly efficient competent cells.

Further, mRNA samples are first obtained by methods allowing us to isolate and purify mRNA from a micro amount of cells or tissues, including commercially available kits such as REX kit (United States Biochemical) and Glass MAX™ RNA spin cartridge system (Gibco-BRL). The obtained mRNA samples are subjected to reverse transcription using oligo(dT) primers to form 1st strand DNA. Next, after homopolymer tails such as G residues are added to the 3'-end of the 1st strand DNA, or adaptors are added to said DNA, the cDNA can be subjected to PCR amplification using oligo(dT) primer and oligo(dC) primer or adaptor primer. Commercially available kits suitable for this technique include SUPERSCRIPT™ pre-amplification system (Gibco-BRL), cDNA CYCLE™ kit (Invitrogen), etc.

Described herein below is the invention in detail.

The novel human cathepsin L2 gene is identified by screening genomic libraries with probe DNA, and cloned. The resulting cloned DNA inserts carrying the novel putative human cathepsin L2 gene are sequenced, and analyzed, thereby determining their nucleotide sequences.

For the probe DNA as used herein, PCR amplification with primers designed and synthesized based on mouse cDNA (AA013726; registered to WashU-HHMI Mouse EST Project by M. Marra et al.) is performed by using as a template λ gt11-phage DNA of commercially available mouse libraries (fetal and brain, Clontech), thereby producing cDNA containing mouse AA013726 sequence, followed by labeling for the probe. Labeling is performed with a DNA labeling kit. Typically, DNA for probes can be labeled with a random-priming kit (Pharmacia LKB), etc., using [α-$^{32}$P] dCTP (Amersham), etc., to form radioactive probes.

Hybridization is performed with said labeled DNA fragments and gene libraries prepared from human tissues and cells, such as human P1 artificial chromosome genomic libraries (Human Genome Mapping Resource Center), and human brain cDNA libraries (e.g., available from Clontech, Palo Alto, Calif., etc.). The human brain cDNA libraries can be constructed in phages such as λ gt10. For example, host *E. coli* such as *E. coli* C600hfl can be infected with the phage construct to form phage plaques.

The hybridization is achieved by transferring the aforementioned formed plaques onto membranes such as nylon filters, as required, optionally followed by denaturation, fixation, washing, etc., and then reacting the transfers on the membrane, with labeled DNA probe fragments which are optionally denatured, as required, in a hybridization buffer. The hybridization operations can be ordinarily conducted at about 35 to about 80° C., more preferably about 50 to about 65° C., for about 15 min to about 36 hours, more preferably about 1 to about 24 hours, but optimal hybridization conditions may be suitably selected. For example, the hybridization is carried out at about 55° C. for about 18 hours. The hybridization buffers can be selected from those customarily used in the art. Examples of the hybridization buffers are Rapid hybridization buffer (Amersham), etc. The denaturation of membranes with transfers includes techniques using an alkali denaturing solution. It is preferred to treat the membrane with a neutralizing solution and a buffer solution after the denaturation. The membrane fixation is usually achieved by baking at about 40° to about 100° C., more preferably about 70° to about 90° C., for about 15 min to about 24 hours, more preferably about 1 to about 4 hours, but desired fixation conditions may be suitably selected. For example, the fixation is carried out by baking at about 80° C. for about 2 hours. The washing of membranes with transfers can be performed with washing solutions customarily used in the art, such as 50 mM Tris-HCl buffer, pH8.0, containing 1M NaCl, 1 mM EDTA and 0.1% sodium dodecyl sulfate (SDS). The membranes such as nylon filters can be selected from those customarily used in the art. Examples of the membrane are nylon filters (Hybond-N, Amersham), etc.

The alkaline denaturing solution, neutralizing solution and buffer solution can be selected from those conventionally used in the art. The alkaline denaturing solution may include, for example, solutions containing 0.5M NaOH and 1.5M NaCl, etc. The neutralizing solution may include, for example, 0.5M Tris-HCl buffers (pH8.0) containing 1.5M NaCl, etc. The buffer solution may include, for example, 2×SSPE (0.36M NaCl, 20 mM $NaH_2PO_4$ and 2 mM EDTA), etc. As required, prior to hybridization, it is desired to optionally prehybridize membranes containing transferred DNA, etc., to prevent non-specific hybridization. For the prehybridization, the sample is dipped, for example, in a solution for prehybridization (50% formamide, 5×Denhardt's solution (0.2% bovine serum albumin and 0.2% polyvinylpyrrolidone), 5×SSPE, 0.1% SDS, and 100 μg/ml thermally denatured salmon sperm DNA), etc., and reacted at about 35 to 50° C., preferably about 42° C., for about 4 to 24 hours, preferably about 6 to 8 hours. These conditions can be determined by those of skill in the art with suitably repeated experiments and preferred conditions would be selected. Labeled probe DNA fragments used in hybridization can be denatured, for example, under heating conditions at about 70 to 100° C., preferably about 100° C., for about 1 to 60 minutes, preferably about 5 minutes, etc. The hybridization is carried out by well known techniques per se in the art or according to methods analogous thereto. As used herein, the stringent conditions refer to, for example, those equivalent to hybridization in about 15 to 50 mM, preferably about 19 to 40 mM, and more preferably about 19 to 20 mM, with regard to Na ion concentration, at about 35 to 85° C., preferably about 50 to 70° C., and more preferably about 60 to 65° C. with regard to temperature.

After the hybridization is completed, the filters are washed extensively to remove labeled probes other than the labeled probe DNA fragments which specifically hybridize. The washing of filters can be performed by a method suitably selected from techniques used in the art. For example, the washing is carried out in 0.5×SSC solution (×SSC=0.15M NaCl, 15 mM citric acid) containing 0.1% SDS. The hybridized plaques can be detected representatively by autoradiography, but plaque detection may be performed by a method suitably selected from techniques used in the art. The plaques corresponding to the detected signal are suspended in a suitable buffer solution such as SM solution (50 mM Tris-HCl buffer, pH7.5, containing 100 mM NaCl and 10 mM $MgSO_4$). After the phage suspension is diluted to a suitable degree, E. coli is infected with the phages and cultivated. Finally, target recombinant phages are recovered from the E. coli culture. If necessary, screening of genomic libraries or cDNA libraries for the target recombinant phages may optionally repeat by hybridization using the aforementioned probe DNA. The target recombinant phages can be obtained by extraction from cultured E. coli, centrifugation, etc.

The phage particles thus obtained can be isolated and purified by customary techniques used in the art. For instance, purified phages are obtained by glycerol gradient ultracentrifugation (Molecular cloning, a laboratory manual, ed. by T. Maniatis, Cold Spring Harbor Laboratory, 2nd ed., 78, 1989), etc. DNA can be isolated and purified from phage particles by customary techniques used in the art. For instance, the resulting phages are suspended in TM solution (50 mM Tris-HCl buffer, pH7.8, containing 10 mM $MgSO_4$), etc., and treated with DNase I and RNase A, etc. followed by addition of a mixture solution of 20 mM EDTA, 50 μg/ml Proteinase K and 0.5% SDS. The resultant mixture is incubated at about 65° C. for 1 hr. and subjected to phenol extraction and then to diethyl ether extraction, followed by precipitation with ethanol to form DNA precipitates. Next, the resultant DNA is washed with 70% ethanol, dried and dissolved in TE solution (10 mM Tris-HCl buffer, pH8.0, containing 10 mM EDTA). In addition, a large amount of target DNA can be obtained by subcloning, etc. For example, the subcloning can be performed with plasmid vectors, etc. in host E. coli, etc. The DNA thus subcloned can also be isolated and purified by techniques including phenol extraction, ethanol precipitation, etc. in the same manner as aforementioned.

The nucleotide sequence of the DNA thus obtained, for example, the nucleotide sequence of single-strand DNA, can be sequenced in the same manner as aforementioned. The sequences are determined by techniques, for example, using a fluorescent DNA sequencer, Model 373A (Applied Biosystems), a Taq dyeprimer cycle sequencing kit (Applied Biosystems), etc.

Analysis of the determined sequences leads to identification of the gene which is similar to known human cathepsin L sequence but is presumed to be a novel human cathepsin member and to genetic analysis thereof. Based upon the analyzed base sequence of the gene, primers are designed for obtaining cDNA for the gene which is presumed to be said novel human cathepsin. Sense primers can be preferably synthesized by selecting from an exon at the 5'-terminal region of the gene which is presumed to be said analyzed novel human cathepsin, while antisense primers can be preferably synthesized by selecting from an exon at the 3'-terminal region of the gene which is presumed to be said analyzed novel human cathepsin (more preferably, it is possible to select from other exons than the exon utilized for said sense primer synthesis). With regard to cDNA for the gene, although its full-length may be aimed to obtain at once, analyzed exons (plural exons) can be utilized to design and synthesize plural primers and plural PCRs may be designed and conducted, thereby obtaining DNA fragments which are subjected to sequencing. Analysis of the nucleotide sequences thus determined leads to determination of an entire nucleotide sequence of said gene cDNA and to isolation of target cDNA of said gene from the cloned DNA fragments based thereon. Primers include oligonucleotides each having preferably 5 or more contiguous nucleotides, more preferably 18 to 25 contiguous nucleotides. Synthesis of the primers is conducted by techniques using an automated DNA synthesizer, for example, model 381A DNA synthesizer, Applied Biosystems, etc.

First strand cDNA is prepared by reverse transcription using mRNA isolated from human tissues, especially from human brain, etc., and reverse transcriptases. The mRNA is first prepared by treating brain tissues with commercially available mRNA extraction-isolation kits or cDNA synthesis kits (to which reagents or systems for extraction and isolation of mRNA are attached), such as Trizol Reagent (Life Technologies). The 1st strand cDNA synthesis primed with an oligo(dT)$_{12-18}$ primer is performed by using said mRNA as a template and a commercially available cDNA synthesis kit such as SUPERSCRIPT™ kit (Life Technologies). For example, the 1st strand cDNA synthesis can be achieved by incubating a mixture of poly(A)$^+$ RNA, 5×RT buffer solution (250 mM Tris-HCl buffer, pH8.3, containing 50 mM $MgCl_2$, 375 mM KCl and 50 mM DTT), dNTPs (deoxyribonucleoside triphosphates; dATP, dGTP, and dCTP, dTTP mix), oligo(dT)$_{16}$ primers, RNase inhibitors (Boehringer Mannheim), MMLV RT (Gibco-BRL) or SUPERSCRIPT™ RT plus (Life Technologies) and deionized distilled water at about 37° C. for about 1 hour.

The resultant 1st strand DNA and primers synthesized according to designs based on exons of the analyzed genes are mixed with 10×reaction buffer (attached to a Taq DNA polymerase kit), dNTPs (deoxyribonucleoside triphosphates; dATP, dGTP, dCTP, and dTTP mix), Taq DNA polymerase and deionized distilled water. The mixture is subjected to 20 to 60 cycles of amplification using an automated thermal cycler such as GENEAMP™ 2400 PCR system (Perkin-Elmer/Cetus) under general PCR cycle conditions. The number of amplification cycles can be suitably set to an appropriate value depending on purposes. The PCR cycle includes, for example, denaturation at 90 to 95° C. for 5 to 100 sec, annealing at 40 to 60° C. for 5 to 150 sec, and extension at 65 to 75° C. for 30 to 300 sec, and preferably denaturation at 94° C. for 15 sec, annealing at 58° C. for 15 sec, and extension at 72° C. for 45 sec. For the annealing temperature and reaction time, an appropriate value is suitably selected by experimentation. For the denaturation and extension time, an appropriate value suitably varies according to the strand length of expected PCR products. In general, the time of annealing preferably varies according to the Tm value of primer-template DNA hybrids. Although, in general, the time of extension is set with the aim of getting 1 min per 1000 bp in strand length, it may be possible to select a shorter time.

The resultant PCR products are usually subjected to electrophoresis on 1 to 2% agarose gels. Specific bands are excised from the gel and DNA is extracted therefrom with commercially available extraction kits such as gene clean kit (Bio 101). The DNA thus extracted is cut out by suitable restriction enzymes, as required, optionally followed by purification and/or phosphorylation of its 5' end with T4 polynucleotide kinase. Next, the DNA fragments are ligated into suitable plasmid vectors including pUC vectors such as pUC18. Suitable competent cells are then transformed therewith. The cloned PCR products are sequenced and analyzed. As a result of the nucleotide sequence analysis, when it is necessary to obtain a 5' and/or 3' end region(s) of the target, it can be achieved by adaptations of rapid amplification of cDNA ends (RACE).

A 5'-terminal cDNA region of said target gene is obtained by utilizing primers designed relying on the analyzed nucleotide sequence of 5'-terminal exon among exons of said gene and a 3'-terminal cDNA region of said target gene is also obtained by utilizing primers designed relying on the analyzed nucleotide sequence of 3'-terminal exon among exons of said gene. Next, depending on necessity, PCR amplification is optionally performed using (1) these primers and/or primers synthesized according to designs based on information on the analyzed nucleotide sequences of 3'- and 5'-terminal cDNA regions of said gene cDNA and (2) as a template 1st strand cDNA prepared with reverse transcriptase from mRNA isolated from human tissues, especially human brain tissues, etc., thereby giving the cDNA of the target gene.

For the 5'-terminal primers, it is desired to select those containing at least initiation codons or those capable of amplifying sequences including said initiation codons. For the 3'-terminal primers, it is desired to select those containing at least stop codons or those capable of amplifying sequences including said stop codons. For the acquisition of full-length cDNA of said gene, PCR can be performed in the same manner as aforementioned. A preferred PCR cycle includes, for example, denaturation at 92 to 95° C. for 10 to 20 sec, annealing at 55 to 60° C. for 10 to 30 sec, and extension at 65 to 75° C. for 150 to 300 sec, and more preferably denaturation at 94° C. for 15 sec, annealing at 58° C. for 15 sec, and extension at 68° C. for 4 min. The resultant PCR products are cloned, sequenced, and nucleotide sequences thereof are analyzed, and determined.

Primers are designed on the basis of the determined nucleotide sequence of DNA. Similarly, target clones can be isolated and characterized via screening using such primers and various animal cell-derived cDNA libraries (e.g., various human cell-derived cDNA libraries). Target genes, novel genes, fragments thereof, etc. are obtained by PCR amplification using these primers. By these techniques, PCR products of which sequences are homologous to human cathepsin L2 but novel sequences can also be searched.

In accordance with the present invention, clones containing the target DNA (as recombinant phages for example) can be obtained. For example, the nucleotide sequence of the gene isolated from the cloned recombinant phages is 1,342 bp in full-length and has a nucleotide sequence as shown in SEQ ID NO: 2 of the Sequence Listing. When the nucleotide sequence of SEQ ID NO: 2 in the Sequence Listing was searched on the GENBANK™/EMBL DNA Data Base, no identical sequence exists. An open reading frame coding for putative 334 amino acids is present in this isolated and identified DNA sequence of about 1.4 kb, and said putative amino acid sequence is as shown in SEQ ID NO: 1 of the Sequence Listing. Said putative protein shows a high homology (about 78% homology) to human cathepsin L and is concluded to be a novel human cathepsin member, named "human cathepsin L2". It is evident that human cathepsin L2 gene codes for the novel protein belonging to the papain family of cysteine proteinases. All of recombinant plasmids prepared using the human cathepsin L2 gene are novel recombinants and transformants or transfectants obtained by transformation or transfection with said plasmids are novel as well.

Nucleic acids having all or part of the nucleotide sequence of SEQ ID NO:2 in the Sequence Listing may also be obtained by chemical synthesis. In that case, it is also possible that fragments are chemically synthesized and then they are enzymatically ligated. It is further possible that the chemically synthesized fragments are used as primers or probes as mentioned above to isolate target sequences. The primers used in the PCR are not limited to specific ones as long as they are capable of amplifying DNA fragments containing the above-mentioned region. Representatively, for the primers, (a) oligonucleotides having a nucleotide sequence corresponding to any region in the nucleotide sequence of SEQ ID NO: 2 in the Sequence Listing and (b) oligonucleotides having a nucleotide sequence complementary to any region in the nucleotide of SEQ ID NO: 2 in the Sequence Listing may be used. More preferably, (a) an oligonucleotide having a nucleotide sequence corresponding to any 5'-terminal region in the nucleotide sequence of SEQ ID NO: 2 in the Sequence Listing and (b) an oligonucleotide having a nucleotide sequence complementary to any 3'-terminal region in the nucleotide sequence of SEQ ID NO: 2 in the Sequence Listing may be used wherein each oligonucleotide may have 3 to 100 nucleotides, preferably 10 to 50 nucleotides, or more preferably 15 to 35 nucleotides. There is no particular limitation for the conditions for the PCR. The PCR can be performed under conventionally known conditions. For example, the conditions may be selected by referring to the descriptions in the aforementioned documents. The single PCR cycle including thermal denaturation of DNA strands, annealing with primers, and synthesis of complementary strands with polymerase is repetitively performed, for example, 10 to 50 times, preferably 20 to 35 times, more preferably 25 to 30 times.

The DNA fragments obtained in accordance with the present invention can be inserted into a suitable vector as described hereinbelow, such as pEX, pMAMneo, and pKG5, and expressed in a suitable host cell as described hereinbelow, such as *E. coli*, yeast, CHO cell line, and COS cell line. The DNA fragment can be inserted into a suitable vector, without any modification or after addition of a suitable control sequence, followed by introduction into an animal to form a transgenic animal capable of expressing cathepsin L2 genes, for example, a human cathepsin L2-expressing one. The animals are mammals, including mouse, rat, rabbit, guinea pig, bovine, etc. Preferably said DNA fragment can be incorporated into an animal fertilized ovum, for example, from mouse, to generate a transgenic animal.

Human cathepsin L2 gene products are confirmed using suitable animal cells, such as COS-1 cells, transfected with the human cathepsin L2 gene. The foreign gene can be introduced into animal cells, such as mammal animal cells, with known methods in the art or with methods substantially similar thereto, including a calcium phosphate method (for example, F. L. Graham et al., Virology, 52: 456, 1973, etc.), a DEAE-dextran method (for example, D. Warden et al., J. Gen. Virol., 3: 371, 1968, etc.), an electroporation method (for example, E. Neumann et al., EMBO J, 1: 841, 1982, etc.), a microinjection method, a liposome method, a virus infection method, a phage particle method, etc.

Thus, the gene products which are produced by animal cells transfected with the human cathepsin L2 gene can be examined and analyzed. The examination and analysis may be performed by means of immunoprecipitation experiments or western blotting using monoclonal anti-human cathepsin L2 antibodies.

Any plasmid into which the human cathepsin L2 gene is incorporated may be used as long as said DNA can be expressed in host cells conventionally used in genetic engineering techniques (such as procaryotic host cells including *Escherichia coli, Bacillus subtilis*, etc. and eucaryotic host cells including yeasts, CHO cell, COS cell, and insect host cells such as Sf21. In such a sequence of the plasmid, it is possible, for example, to modify codons suitable for expressing the cloned DNA in selected host cells or to construct restriction enzyme sites. It is also possible to contain control sequences, enhancer sequences, etc. for facilitating the expression of the aimed gene; linkers, adaptors, etc. useful for ligating the aimed gene; sequences useful in controlling resistance to antibiotics or in controlling metabolism or in selection; and the like.

Preferably, suitable promoters may be used. For example, such promoters may include tryptophan promoter (trp), lactose promoter (lac), tryptophan-lactose promoter (tac), lipoprotein promoter (lpp), λ phage $P_L$ promoter, etc. in the case of plasmids where *Escherichia coli* is used as a host; SV40 late promoter, MMTV LTR promoter, RSV LTR promoter, CMV promoter, SRα promoter, etc. in the case of plasmids where an animal cell is used as a host; and GAL1, GAL10 promoters, etc. in the case of plasmids where yeast is used as a host.

Examples of the plasmid suitable for host *Escherichia coli* are pBR322, pUC18, pUC19, pUC118, pUC119, pSP64, pSP65, pTZ-18R/-18U, pTZ-19R/-19U, pGEM-3, pGEM-4, pGEM-3Z, PGEM-4Z, pGEM-5Zf(—), pBLUESCRIPT KS™ (Stratagene), etc. Examples of the plasmid vector suitable for expression in *Escherichia coli* are pAS, pKK223 (Pharmacia), pMC1403, pMC931, pKC30, pRSET-B (Invitrogen), etc. The plasmid for host animal cells may include SV40 vector, polyomavirus vector, vaccinia virus vector, retrovirus vector or the like. Examples of the plasmid for host animal cells are pcD, pcD-SRα, CDM8, pCEV4, pME18S, pBC12BI, pSG5 (Stratagene) or the like. Examples of the plasmid for host yeasts are YIp vector, YEp vector, YRp vector, YCp vector, etc., including pGPD-2, etc. *Escherichia coli* host cells may include those derived from *Escherichia coli* K12 strains, such as NM533 XL1-Blue, C600, DH1, DH5, DH11S, DH12S, DH5α, DH10B, HB101, MC1061, JM109, STBL2 and BL21(DE3)pLysS.

In the case where the host cells are animal cells, they may include COS-7 cells, COS-1 cells, and CV-1 cells derived from African green monkey fibroblasts, COP cells, MOP cells, and WOP cells derived from mouse fibroblasts, CHO cells and CHO DHFR[31] cells derived from chinese hamster, human HeLa cells, C127 cells derived from mouse cells, NIH 3T3 cells derived from mouse cells, etc. The insect cells may include *bombyx mori* larva, *bombyx mori* culture cells such as BM-N cells, etc. wherein *bombyx mori* nuclear polyhedrosis virus is employed as a vector. The host cell used herein may include plant cells. A variety of plant host cells as well as vectors compatible therewith are widely known in the art.

In the genetic engineering techniques of the present invention, it is possible to use various restriction enzymes, reverse transcriptases, DNA modifying and degrading enzymes which are used for modifying or converting a DNA fragment to a structure suitable for cloning, DNA polymerases, terminal nucleotidyltransferases, DNA ligases; etc., which are known or common in the art. Examples of the restriction enzyme are those disclosed in R. J. Roberts, Nucleic Acids Res., 13: r165, 1985; S. Linn et al. ed., Nucleases, p. 109, Cold Spring Harbor Lab., Cold Spring Harbor, N.Y., 1982; R. J. Roberts, D. Macelis, Nucleic Acids Res., 19: Suppl. 2077, 1991; etc., the disclosures of which are hereby incorporated by reference. Examples of the reverse transcriptase are those derived from mouse Moloney leukemia virus (MMLV), from avian myeloblastosis virus (AMV), etc. RNase H-deficient reverse transferase or the like is preferably used. Particularly, modified MMLV RT whose RNase H activity is lacked is preferred and more preferably highly thermostable one is used. The suitable reverse transcriptase is MMLV RT (Gibco-BRL), SUPER-SCRIPT™ RI plus (Life Technologies), etc.

Examples of the DNA polymerase are *Escherichia coli* DNA polymerase, Klenow fragment which is a derivative of *E. coli* DNA polymerase, *E. coli* phage T4 DNA polymerase, *E. coli* phage T7 DNA polymerase, thermoduric bacteria DNA polymerase, etc. The terminal nucleotidyltransferase includes TdTase capable of adding a dideoxynucleotide (dNMP) to a 3'-OH terminal, as disclosed in R. Wu et al. ed., "Methods in Enzymology", Vol. 100, p. 96, Academic Press, New York (1983). The modifying and degrading enzyme for DNA includes exonuclease, endonuclease, etc. Examples of such enzymes are snake venom phosphodiesterase, spleen phosphodiesterase, *E. coli* DNA exonuclease I, *E. coli* DNA exonuclease III, *E. coli* DNA exonuclease VII, λ exonuclease, DNase I, nuclease S1, Micrococcus nuclease, etc. Examples of the DNA ligase are *E. coli* DNA ligase, T4 DNA ligase, etc.

The vector (or vehicle) which is suitable for cloning DNA genes and constructing DNA libraries includes plasmid, λ phage, cosmid, P1 phage, F factor, YAC, etc. Preferred examples of such vectors are vectors derived from λ phage, such as Charon 4A, Charon 21A, λ gt10, λ gt11, λ DASHII, λ FIXII, λ EMBL3 and λ ZAPII™ (Stratagene), etc.

The cells transformed with an expression vector comprising nucleic acids encoding the protein can be repeatedly cloned, if necessary, using a suitable selective marker to give cells which stably exhibits a high ability of expressing the protein. For example, when a dhfr gene is used as a selective marker in connection with transformants wherein the host is an animal cell, the resistant cells are selected by a culture with a sequential increase in the methotrexate (MTX) concentration to amplify the introduced protein-encoding DNA in the cells whereby a cell strain exhibiting far higher expression can be obtained.

The transformants or transfectants can be cultured, under conditions wherein nucleic acids encoding the protein are expressible, to produce and accumulate targets. The transformants (transfectants) can be cultured in media conventionally used in the art.

For example, cultivation of the transformant (transfectant) in which the host is a procaryotic cell such as *Escherichia coli* and *Bacillus subtillis*, yeast or the like can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, malt extracts, beancakes, potato extracts, etc. Examples of the minerals may include calcium chloride, sodium dihydrogen phosphate, magnesium chloride, calcium carbonate, etc. It may also be supplemented with yeast extracts, vitamins, casamino acids, growth-promoting factors, etc. Depending on necessity, the medium may be supplemented with drugs such as 3β-indolyl acrylic acid in order to improve efficiency of the promoter. It is desired that the pH for culture medium is from about 5 to about 8.

In the case of the Escherichia host, the cultivation is carried out usually at about 15 to 45° C. for about 3 to 75 hours. As required, aeration and stirring may be applied. In case of the transformant in which the host is an animal cell, the culture medium used may include MEM medium, RPMI 1640 medium, DMEM medium, etc. which are containing, for example, about 5 to 20% of fetal calf serum. It is preferable that the pH is from about 6 to about 8. The cultivation is usually carried out at about 30 to 40° C. for about 15 to 72 hours. As required, aeration and stirring may be optionally applied.

To extract the proteins from the cultured microorganisms or cells, the microorganisms or cells are collected by known methods after the cultivation, suspended in a suitable buffer solution, disrupted by sonication, lysozyme and/or freeze and thawing, etc. and, then, a crude extract is obtained by centrifugation or filtration. Other conventional extraction or isolation methods can be applied. The buffer solution may contain a protein-denaturing agent such as urea or guanidine hydrochloride or a detergent such as Triton X-100 (trade name) or Tween-80 (trade name).

In the case where the target proteins are secreted into culture media, supernatant liquids are separated from the microorganisms or cells after the cultivation is finished and the resulting supernatant liquid is collected by widely known methods. The culture supernatant liquid thus obtained and target products contained in extracts can be purified by suitable combinations of widely known techniques per se for separation, isolation and purification. Such widely known techniques per se are, for example, salting out such as ammonium sulfate precipitation, etc.; gel filtration on SEPHADEX™, etc.; ion exchange chromatography using carriers having, for example, a diethylaminoethyl or carboxymethyl group, etc.; hydrophobic chromatography using carriers having, for example, a hydrophobic group such as butyl, octyl, or phenyl, etc.; pigment (or chromophore) gel chromatography; electrophoresis; dialysis; ultrafiltration; affinity chromatography; high performance liquid chromatography; etc. Preferably, the target products can be isolated, separated and purified by polyacrylamide gel electrophoresis, affinity chromatography in which an antibody capable of specifically reacting with an antigen, such as a monoclonal antibody, is immobilized. Examples of such techniques also include gelatine-agarose affinity chromatography, heparin-agarose chromatography, etc.

Further, by relying on the nucleotide sequence of human cathepsin L2 gene according to the present invention, equivalent proteins or derivatives thereof wherein the amino acid sequence of human cathepsin L2 is altered may be produced with conventional genetic engineering techniques. Such alterations includes substitution, deletion, insertion, transfer or addition of one or more amino acid residues, etc. Such methods for mutation, conversion, and/or modification may also include those described in Nippon Seikagaku Kai (Biochemical Society of Japan) ed., "Zoku-Seikagaku Jikken Kouza 1, Idenshi Kenkyuho II (Lectures on Biochemical Experiments (Second Series; 1), Methods for Gene Study II)", p.105 (Susumu HIROSE), Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinant DNA Technique))", p.233 (Susumu HIROSE), Tokyo Kagaku Dojin, Japan (1992); R. Wu, L. Grossman, ed., "Methods in Enzymology", Vol.154, p.350 & p.367, Academic Press, New York (1987); R. Wu, L. Grossman, ed., "Methods in Enzymology", Vol.100, p.457 & p.468, Academic Press, New York (1983); J. A. Wells et al., Gene, 34: 315, 1985; T. Grundstroem et al., Nucleic Acids Res., 13: 3305, 1985; J. Taylor et al., Nucleic Acids Res., 13: 8765, 1985; R. Wu ed., "Methods in Enzymology", Vol. 155, p. 568, Academic Press, New York(1987); A. R. Oliphant et al., Gene, 44: 177, 1986; etc., the disclosures of which are hereby incorporated by reference. Examples of such techniques include site-directed mutagenesis (or site-specific mutagenesis) using synthetic oligonucleotides, Kunkel method, dNTP[α S] method (Eckstein method), area-directed mutagenesis using sulfite, nitrite, etc. and the like.

Further, the proteins thus obtained can be modified chemically for amino acid residues. The protein can also be modified or partially degraded with enzymes including peptidases such as pepsin, chymotrypsin, papain, bromelain, endopeptidase, exopeptidase or the like to produce a derivative. The proteins has ordinarily a carboxyl group (—COOH) or a carboxylate group (—COO$^-$) at their C-terminal end and may also have an amide group (—CONH$_2$—) or an ester group (—COOR) at their C-end. For the ester group, R includes a $C_{1-6}$ alkyl group such as methyl, ethyl, n-propyl, isopropyl and n-butyl; a $C_{3-8}$ cycloalkyl group such as cyclopentyl and cyclohexyl; a $C_{6-12}$ aryl group such as phenyl and α-naphthyl; a $C_{7-14}$ aralkyl group including a phenyl-$C_{1-2}$ alkyl group such as benzyl and phenethyl and an α-naphthyl-$C_{1-2}$ alkyl group such as α-naphthylmethyl; a pivaloyloxymethyl group, conventionally used as an ester for oral applications; etc. In case the proteins has a carboxyl group (or carboxylate group) at any other site than C-terminal end, they may include those having an aminated or esterified carboxyl group. In this case, such esters are, for example, those types selected from the groups as listed for the aforementioned C-terminal esters.

Further, the proteins may include those in which an amino group on an N-terminal methionine residue of the aforementioned proteins is protected with a protective group (e.g., $C_{1-6}$ acyl including $C_{1-5}$ alkyl-carbonyl such as formyl and acetyl, etc.), those in which a glutamyl moiety produced by in vivo cleavage of an N-terminal side thereof is pyroglutamated, those in which a substituent (e.g., —OH, —COOH, amino, imidazole, indole, guanidino, etc.) on a side chain moiety of intramolecular amino acid residues is protected with a suitable protective group (e.g., $C_{1-6}$ acyl such as formyl and acetyl, etc.), conjugated proteins including those coupled with a saccharide chain (so-called "glycoprotein"), and the like. In addition, the proteins may be expressed as fusion proteins when they are produced using genetic recombinant techniques, which are subjected to in vivo and in vitro conversion into and/or processing to those having a biological activity substantially equivalent to native human cathepsin L2. The fusion protein production conventionally used in genetic engineering can be employed. Further, such fusion proteins can be isolated and/or purified by means of affinity chromatography or the like wherein the technique employs a fusion portion thereof. In a preferred embodiment of the present invention, those fused with marker sequences (e.g., hexa-histidine peptide) effective in suitably carrying out purification, etc., can be used. The structure of proteins can be modified, improved, etc. by techniques as described in Nippon Seikagaku Kai (Biochemical Society of Japan) ed., "Shin-Seikagaku Jikken Kouza 1, Tanpakushitsu VII, Tanpakushitsu Kougaku (New Lectures on Biochemical Experiments 1, Proteins VII, (Protein Engineering))", Tokyo Kagaku Dojin, Japan (1993), the disclosures of which are hereby incorporated by reference, or by techniques as described in references cited therein as well as methods substantially equivalent thereto.

In addition, as described herein below, the biological activity may include those having an immunological activity including an antigenic activity.

Hence, the present invention relates to proteins wherein one or more amino acid residues may differ from native amino acid residues from the viewpoint of homology, and proteins wherein the positions of one or more amino acid residues may differ from those of native residues. The present invention includes deletion analogues wherein one or more amino acid residues (for example, 1 to 73 residues, preferably 1 to 60 residues, more preferably 1 to 40 residues, further more preferably 1 to 20 residues, particularly 1 to 10 residues, etc.) characteristic of human cathepsin L2 are deleted; substitution analogues wherein one or more amino acid residues (for example, 1 to 73 residues, preferably 1 to 60 residues, more preferably 1 to 40 residues, further more preferably 1 to 20 residues, particularly 1 to 10 residues, etc.) characteristic of human cathepsin L2 are replaced with other amino acid residues; and addition analogues wherein one or more amino acid residues (for example, 1 to 73 residues, preferably 1 to 60 residues, more preferably 1 to 40 residues, further more preferably 1 to 20 residues, particularly 1 to 10 residues, etc.) are added. All of the above mentioned variants, mutants or the like are included in the present invention as long as domain structures or enzyme active center structures commonly characteristic of native human cathepsin L2 are maintained. It is thought that human cathepsin L2 of the present invention may include proteins having a primary structural conformation identical with or substantially equivalent to native human cathepsin L2 or a part thereof. It is also thought that human cathepsin L2 may include proteins having a biological activity identical with or substantially equivalent to native human cathepsin L2. It may be one of mutants (variants) naturally produced or occurred.

The human proteins according to the present invention include, for example, those having more than 80% homology, preferably 90% or more homology, to an amino acid sequence selected from the group consisting of amino acid residues 114 to 334, amino acid residues 18 to 334, and amino acid residues 1 to 334, of SEQ ID NO: 1 in the Sequence Listing.

The part of the human protein according to the present invention may include any as long as it is part of the peptide of said human protein (i.e., a peptide fragment of said protein) and has a substantially equivalent activity to the human cathepsin L2. Examples of the peptide fragment of the present protein are peptides having an amino acid sequence with at least 5 contiguous amino acid residues, preferably 20 or more contiguous amino acid residues, still preferably 50 or more contiguous amino acid residues, more preferably 70 or more contiguous amino acid residues, still more preferably 100 or more contiguous amino acid residues, in a certain case, 200 or more contiguous amino acid residues, of the constituent amino acids of the human cathepsin L2. Examples of such peptide fragments are still those having the same homology as mentioned above, with regard to homologies to a region corresponding to the amino acid sequence of SEQ ID NO: 1.

In the present specification, the term "substantially equivalent" proteins mean that proteins are substantially same one another in terms of activity, including catalytic activity, physiological activity and biological activity. In addition, the meaning of said term may cover the case where the proteins have the substantially same quality in terms of activity. For said substantially same quality in terms of activity, the activity includes, for example, proteolytic activity and an activity of degrading synthetic substrates for cysteine proteinases, etc. The substantially same quality in terms of activity means that the activity is in the same property in its nature (for example, the activity is in the same property physiologically, pharmacologically or biologically). For example, it is preferred that the activity including proteolytic activity or the like is similar (for example, about 0.001 to 1,000-fold, preferably about 0.01 to 100-fold, more preferably about 0.1 to 20-fold or, further more preferably, about 0.5 to 2-fold), but degree of the activity as well as the quantitative elements such as molecular weight of the protein may vary. For example, substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs, which do not effect the tertiary structure of the protein. The non-polar (hydrophobic) amino acids include alanine, phenylalanine, leucine, isoleucine, valine, proline, tryptophan and methionine. The polar (neutral) amino acids include glycine, serine, threonine, cysteine, tyrosine, asparagine, and glutamine, The positively charged (basic) amino acids include arginine, lysine and histidine. The negatively charged (acidic) amino acids include aspartic acid and glutamic acid.

The proteins and peptide fragments thereof can be synthesized with well known techniques in the art of peptide synthesis, including chemical peptide synthesis techniques such as liquid phase peptide synthesis and solid phase peptide synthesis. In such techniques, for example, using resin supports for synthesizing proteins or peptides, suitably protected amino acids are coupled step by step to desired amino acid sequences on said resin supports by well known condensation techniques per se. The condensation may be performed, preferably with various well known activating reagents per se. Such reagents are preferably carbodiimides such as dicyclohexylcarbodiimide. In cases where the products have protecting groups, targets can be obtained by suitably removing such protecting groups.

In cases where the protein or peptide fragment thereof thus obtained is in a free form, the free protein (or the peptide fragment) can be converted into a salt thereof by known methods per se or methods analogous thereto. In case where the protein or peptide fragment thereof thus obtained is in a salt form vice versa, the protein salt (or the peptide fragment salt) can be converted into a free form or into any other salt thereof by known methods per se or methods analogous thereto. The salts of said protein and peptide fragment according to the present invention preferably include physiologically or pharmaceutically acceptable salts but are not limited to. Examples of such salts are salts thereof with inorganic acids (e.g. hydrochloric acid, hydrobromic acid, sulfuric acid, nitric acid, phosphoric acid, etc.), salts thereof with organic acids (e.g. acetic acid, formic acid, maleic acid, fumaric acid, succinic acid, citric acid, tartaric acid, malic acid, benzoic acid, methanesulfonic acid, p-toluenesulfonic acid, benzenesulfonic acid, etc.), etc. In addition, examples of such salts are ammonium salts thereof, salts thereof with organic bases such as ethylamine, dimethylamine, trimethylamine and hydroxyethylamine.

The human cathepsin L2 of the present invention, and mutants, modified products, and derivatives thereof, etc. can be subjected to isolation and purification treatments as aforementioned. In the present invention, the terms "fragment", "derivative" and "analogue" refer to polypeptides having the substantially same biological function or activity as (1) a polypeptide of SEQ ID NO: 1, (2) a polypeptide which is encoded by non-spliced or specifically spliced hnRNA or mRNA transcribed from the sequence of SEQ ID NO: 2, or (3) a polypeptide which is encoded by the deposited genomic DNA, when the term "fragment", "derivative" or "analogue" thereof is referred with regard to the aforementioned polypeptide (1), (2) or (3). Accordingly, the analogues of the present human cathepsin L2 protein include pro-proteins which can be activated in a manner as to cleave the proprotein moiety, leading to production of an active mature polypeptide, etc. The polypeptides of the present invention may be recombinant polypeptides, native polypeptides or synthetic polypeptides. In a specific preferred embodiment, those are recombinant polypeptides.

The proteins or a salt thereof according to the present invention which are (1) natural cathepsin, species of enzymes, with cysteine proteinase activity, belonging to the papain family and cathepsin-like activators for enzymes, other than cathepsin L, (particularly, human cathepsin L2) or (2) members having the substantially same activity as said natural cathepsin (especially, human cathepsin L2), or peptide fragments thereof, can be adapted to be employed for studies including development of and research on enzyme inhibitors, studies on development of pharmaceuticals and studies on biological phenomena and reactions in which human cathepsin L2 is thought to be involved. Such proteins and peptide fragments can further be adapted to be used for the preparation of antibodies thereagainst, and for investigation and examination on specific targets to be analyzed or assayed.

Human cathepsin L2 is a novel member of cysteine proteinases and, therefore, useful in studying phenomena and reactions in various normal cellular processes (in which the cysteine proteinases are expected to be involved), including the turnover of intracellular proteins, prohormone activation, and bone remodeling. In addition, human cathepsin L2 is useful or effective in elucidating its functions related to a variety of pathological conditions, diseases and disorders such as Alzheimer's disease, pulmonary emphysema, rheumatoid arthritis, muscular dystrophy, osteoporosis, neurodegenerative disease, and cancer invasion and metastasis, especially related to cancers and tumors and thus expected to be quite useful in and advantageous to (i) elucidation of onset mechanism for such pathological conditions, diseases and disorders and (ii) research on and development in therapy as well as therapeutic agents therefor.

In another aspect, the present invention encompasses DNA sequences coding for the above-mentioned polypeptides, human cathepsin L2 polypeptides having all or part of the characteristics of native substance and DNA sequences coding for analogues or derivatives thereof. The polynucleotides of the present invention may be those which code for (1) mature proteins wherein one or more additional amino acids are added to an $NH_2$-or COOH-end thereof, or (2) amino acids for intrinsic polypeptides of a mature protein (for example, the protein in mature form has one or more polypeptide chains therein). Such sequences may be those which play some roles in processings from a precursor to a protein in mature form. Thus, for example, the sequences may include those which can promote the transfer or transport of proteins, those which can extend or reduce the half-life of proteins, or those which can facilitate the detection or production of proteins by manipuration thereof. In general, the added amino acids, for example, are removed from mature proteins by processing with intracellular enzymes. The precursor proteins having a mature form polypeptide fused with one or more pro-sequences can be polypeptides in inactive form. When the pro-sequences are removed, such inactive precursors are usually activated. Prior to the activation, some or all of the pro-sequences can be removed. Usually, such a precursor is called "proprotein". The polypeptides of the present invention may be (1) mature proteins, (2) mature proteins to which a leader sequence is added (which may be called "preprotein"), (3) precursors, for mature protein, which have one or more pro-sequences which are not leader sequences of preprotein, or (4) pre-proproteins which are precursors for proprotein having a leader sequence together with or one or more pro-sequences. Said pro-sequences can be removed in a step of processing where a polypeptide in active or mature form is usually generated.

The DNA sequences of the present invention provides information concerning the amino acid sequences of the mammal proteins that have not been known so far. Therefore, utilization of the above information is included in the present invention. Such utilization includes design of any of probes for isolating and detecting mammal, in particular human, genomic DNA or cDNA, encoding human cathepsin L2, related (or associated) proteins, etc.

The DNA sequences of the present invention are useful as probes for isolating and detecting mammal, most preferably murine or human, genomic DNA and cDNA, coding for human cathepsin L2 or related proteins thereof. As required, the probe can be optionally labeled with markers as listed herein for antibodies. To isolate genes, PCR techniques or PCR using reverse transcriptase (RT) (RT-PCR) can be used. Human cathepsin L2 cDNA and associated DNA thereof can be used in isolating and detecting human cathepsin L2-related genes, via selecting characteristic sequence regions based on amino acid sequences deduced from the cloned and sequenced human cathepsin L2 cDNA sequence, then designing and chemically synthesizing DNA primers, and carrying out PCR, RT-PCR, or any other techniques with the obtained DNA primers. For example, the expression of human cathepsin L2 mRNA in human tissues can been examined by Northern blotting for various tissue-derived poly $(A)^+$ RNA. When the cDNA according to the present invention is employed as a probe, techniques including Northern blotting, Southern blotting, in situ hybridization or the like enable us to detect and/or assay human cathepsin L2 mRNA expression or human cathepsin L2 genes per se in human tissues, which may contribute greatly to research and development studies on not only roles and functions of cysteine proteinases, involved in many normal cellular processes in human tissues, including the turnover of intracellular proteins, prohormone activation, and bone remodeling, but also a number of diseases, disorders and pathological conditions such as Alzheimer's disease, pulmonary emphysema, rheumatoid arthritis, muscular dystrophy, osteoporosis, neurodegeneration disease and cancer invasion and metastasis.

The probes of the present invention can be adapted to be utilized in gene diagnosis of diseases, disorders and pathological conditions related to human cathepsin L2. Such diagnosis may be those which diagnose abnormality (such as defect, mutation, reduced expression, excessive expression, etc.) of nucleic acid coding for said human cathepsin L2 and related proteins.

In transferring the DNA (for example, the DNA coding for human cathepsin L2) obtainable by the present invention to target animals, it is generally advantageous to use it as a DNA fragment or to use it by ligation to the downstream of promoters capable of expressing said DNA in animal cells. For example, when human cathepsin L2 DNA is introduced into mouse, gene constructs wherein human cathepsin L2 DNA is ligated to the downstream of various compatible animal-derived promoters which are able to express human cathepsin L2 DNA are micro-injected to fertilized ovum of a target animal (such as mouse fertilized ovum), thereby generating gene-introduced (transgenic) mice which produce human cathepsin L2 in a high amount. The mice are not particularly limited to those of a pure line but include C57BL/6, Balb/C, C3H, (C57BL/6×DBA/2)$F_1$(BDF$_1$), etc. The promoters preferably used herein for this purpose include promoters derived from virus, ubiquitous expression promoters such as metallothionein promoters, etc. When said human cathepsin L2 DNA is introduced thereinto, it may be adapted to be used by integration into a recombinant retrovirus. Preferably, mouse fertilized ovum into which the target DNA is introduced can be grown, for example, using foster parent mice such as ICR mice.

Transfer of DNA (e.g., DNA coding for human cathepsin L2) obtained according to the present invention in a fertilized ovum stage is secured so that the DNA can be present in all of germ cells and somatic cells of the target animal. The fact that human cathepsin L2-encoding DNA is present in germ cells of the produced transgenic animal after the transfer of the DNA means that all progeny of the produced transgenic animal has DNA coding for said human cathepsin L2 in all of their germ cells and somatic cells. Descendants of the animal of this type which has inherited the gene have a possibility of being able to express said human cathepsin L2 in all of their germ cells and somatic cells.

After confirming that gene can be maintained via mating in a stable manner, the animal into which human cathepsin L2 DNA is introduced can be subjected to breeding and passage, as a DNA-possessing animal, under conventional breeding environments. In addition, female/male animals having the target DNA are mated, thereby giving homozygote animals having the introduced gene in both homologous chromosomes. Those homozygote female/male animals are mated, thereby enabling us to propagate and breed the animals for passage so that all progeny can have said DNA. In the animals into which said human cathepsin L2 DNA is introduced, said human cathepsin L2 protein is highly expressed. Therefore, the animals are useful for screening of inhibitors to said human cathepsin L2 protein, etc. The animals are also useful for screening of antisense oligonucleotides (such as antisense DNA) which are capable of inhibiting the expression of human cathepsin L2 gene, etc.

These transgenic animals can also be used as cell sources for tissue culture. For example, DNA or RNA in tissues of the transgenic mouse is directly analyzed or the tissue proteins which are expressed by gene are analyzed whereby proteins related to the papain family of cysteine proteinases can be analyzed. Cells in tissues having said cathepsin L2 are cultivated by standard tissue culture techniques and the resulting ones are adapted to be used, thereby now enabling us to study the function of cells derived from tissues (such as thymus, testis, brain, intestine, kidney and other tissues). In addition, when such cells are adapted to be used, it is now possible to assist development of pharmaceuticals, for example, which potentiate the function of various tissues, etc. Further, if the highly expressing cell lines are available, cathepsin L2 can be isolated and purified therefrom. The techniques related to transgenic mice, etc. are conducted, for example, according to those described in documents such as Brinster, R. L., et al.,; Proc. Natl. Acad. Sci. USA, 82: 4438, 1985; Costantini, F. & Jaenisch, R. (eds): Genetic manipulation of the early mammalian embryo, Cold Spring Harbor Laboratory, 1985, etc., the disclosures of which are hereby incorporated by reference, those described in references quoted therein, or modified methods derived therefrom.

It is possible to produce mutant mice (knockout mice) which have mutation in the gene identified according to the present invention (such as DNA coding for mouse cathepsin L2 corresponding to human cathepsin L2) without any expression of mouse cathepsin L2 at all. For example, it is possible to construct a targeting vector having a mutant gene wherein a gene cassette consisting of a neo-resistant gene-poly A addition signal is inserted into an exon locating near the center of genome DNA of about 8 kb, comprising a 4 kb region upstream and downstream translation initiation codons of said gene, said exon also being near the translation initiation codons. The gene cassette to be inserted includes, in addition to the neo-resistant gene cassette, DT-A cassette, tk cassette, lacZ cassette, etc. The targeting vectors are opened to produce linear ones which are introduced into established mouse embryonic stem cells (ES cells) by electroporation, followed by cultivation. Next, ES cells acquiring the neo-resistance are selected. The ES cells can be prepared by selection from mouse lines such as 129, C57BL/6, and F1 (C57BL/6×CBA) mice. The ES cells acquiring the neo-resistance are supposed to have a homologous recombination with the targeting vector wherein the gene cassette is inserted in a mouse cathepsin L2 gene region, leading to destruction of at least one of mouse cathepsin L2 gene alleles whereby mouse cathepsin L2 cannot be normally expressed. In the selection, appropriate methods are used selectively depending on each inserted gene cassette. The introduction of mutation can be confirmed by PCR, Southern hybridization, Northern hybridization, etc.

The mutation-introduced ES cell can be injected into an 8-cell stage embryo taken out from C57BL/6, BALB/c, ICR mice, etc., followed by cultivation for one day. The resultant product generated in a blastocyst can be transplanted to a foster parent such as ICR, thereby growing up to an individual. A littermate which is born thereby is a chimera mouse derived from mutated ES cells and normal host embryo and the content degree of cells derived from ES cells is judged from the hair color of the individual animal. Accordingly, for ES cells and host embryos a combination of lines having different hair color each other is preferable. The resulting chimera mice are of hetero mutation and, when those mice are appropriately mated, mice of homo-mutation can be obtained. Mouse cathepsin L2 is not expressed at all in every germ cells and somatic cells of the homo-mutated mice thus generated, wherein only mouse cathepsin L2 gene is destroyed, and progenies obtained by breeding and passage of the homo-mutated mice are of the same phenotype, too.

The knockout mice are useful in analysis of (1) a role of cathepsin L2 in a life cycle of an individual, such as generation, growth, reproduction, aging, and death, and also of (2) the function of cathepsin L2 in each of organs and tissues as compared with normal mice. In addition, they can be applied to development of pharmaceuticals related to cysteine proteinases. The knockout mice can be adapted to be used not only as such model animals but also as cell sources for tissue culture. The knockout mice can also be adapted to be used in analysis of functions, etc. of cathepsin L2 in a cellular level. The techniques related to knockout mouse, etc. can be conducted according to methods described in documents such as Mansour, S. L., et al.,; Nature, 336: 348–352, 1988; Joyner, A. L., ed.; Gene targeting, IRL Press, 1993; and Shinichi Aizawa: Gene Targeting, Preparation of Mutant Mouse Using ES Cells, Yodosha, Japan, 1995; etc., the disclosures of which are hereby incorporated by reference, those described in references quoted therein, or modified methods derived therefrom.

In accordance with the present invention, antisense oligonucleotides (antisense nucleic acids) capable of inhibiting the expression of human cathepsin L2 gene may be designed and synthesized based on information on the nucleotide sequences of cloned and determined human cathepsin L2 protein-encoding DNAs. Such antisense oligonucleotides (antisense nucleic acids) are capable of hybridizing with human cathepsin L2 mRNA to inhibit the function of said mRNA, or of controlling or modulating the expression of a cathepsin L2 gene via interaction with cathepsin L2-related mRNA, etc. oligonucleotides complementary to, and specifically hybridizable with, selected sequences of cathepsin L2-related genes are useful in controlling or regulating the expression of a cathepsin L2 gene in vitro and in vivo, and in treating or diagnosing disease states. The term "corresponding" means homologous to or complementary to a particular sequence of the nucleotide sequence or nucleic acid including the gene. As between nucleotides (nucleic acids) and peptides (proteins), "corresponding" usually refers to amino acids of a peptide (protein) in an order derived from the sequence of a nucleotides (nucleic acids) or its complement. The gene 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop may be selected as preferred targets though any region may be a target among said genes. The relationship between the target nucleic acids and oligonucleotides complementary to at least a portion of the target, specifically hybridizable with the target, is denoted as "antisense". The antisense oligonucleotides may be polydeoxynucleotides containing 2-deoxy-D-ribose, polyribonucleotides containing D-ribose, any other type of polynucleotide which is an N-glycoside of a purine or pyrimidine base, or other polymers containing nonnucleotide backbones (e.g., protein nucleic acids and synthetic sequence-specific nucleic acid polymers commercially available) or nonstandard linkages, providing that the polymers contain nucleotides in a configuration which allows for base pairing and base stacking such as is found in DNA and RNA. They may include double- and single-stranded DNA, as well as double- and single-stranded RNA and DNA:RNA hybrids, and also include, as well as unmodified forms of the polynucleotide or oligonucleotide, known types of modifications, for example, labels which are known to those skilled in the art, "caps", methylation, substitution of one or more of the naturally occurring nucleotides with analogue, internucleotide modifications such as, for example, those with uncharged linkages (e.g., methyl phosphonates, phosphotriesters, phosphoramidates, carbamates, etc.) and with charged linkages or sulfur-containing linkages (e.g., phosphorothioates, phosphorodithioates, etc.), those containing pendant moieties, such as, for example, proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.). The terms "nucleoside", "nucleotide" and "nucleic acid" will include those moieties which contain not only the known purine and pyrimidine bases, but also other heterocyclic bases which have been modified. Such modifications include methylated purines and pyrimidines, acylated purines and pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like.

The antisense nucleic acid of the present invention is RNA, DNA or a modified nucleic acid. Examples of modified nucleic acid are, but not limited to, degradation-resistant sulfurized and thiophosphate derivatives of nucleic acids, and poly- or oligonucleoside amides. Preferred design modifications of the antisense nucleic acids of the present invention are modifications that are designed to:

(1) increase the intracellular stability of the nucleic acid;

(2) increase the cellular permeability of the nucleic acid;

(3) increase the affinity of the nucleic acid for the target sense strand; or (4) decrease the toxicity (if any) of the nucleic acid.

Many such modifications are known to those skilled in the art, as described in J. Kawakami et al., Pharm Tech Japan, 8: 247, 1992; ibid., 8: 395, 1992; S. T. Crooke et al. ed., Antisense Research and Applications, CRC Press, 1993; etc. The antisense nucleic acids may contain altered or modified sugars, bases or linkages, be delivered in specialized systems such as liposomes, microspheres or by gene therapy, or may have attached moieties. Such attached moieties include polycationic moieties such as polylysine that act as charge neutralizers of the phosphate backbone, or hydrophobic moieties such as lipids (e.g., phospholipids, cholesterols, etc.) that enhance interaction with cell membranes or increase uptake of the nucleic acid. Preferred lipids that may attached are cholesterols or derivatives thereof (e.g., cholesteryl chloroformate, cholic acid, etc.). The moieties may be attached at the 3' or 5' ends of the nucleic acids, and also may be attached through a base, sugar, or internucleoside linkage. Other moieties may be capping groups specifically placed at the 3' or 5' ends of the nucleic acids to prevent degradation by nuclease such as exonuclease, RNase, etc. Such capping groups include, but are not limited to, hydroxyl protecting groups known to those skilled in the art, including glycols such as polyethylene glycols, tetraethylene glycol and the like.

The inhibitory activity of antisense nucleic acids can be examined using the transformant (or transfectant) of the present invention, the in vitro and in vivo gene expression system of the present invention, or the in vitro and in vivo translation system of human cathepsin L2. The nucleic acid can be placed in the cell through any number of ways known per se.

According to inventor's investigation results as described herein above, techniques are provided for transferring human cathepsin L2 genes and recombinant DNA molecules into hosts, expressing human cathepsin L2 therein, and isolating and obtaining target human cathepsin L2. Thus, according to the present invention, transformants or transfectants capable of substantially expressing human cathepsin L2 genes and production processes and use thereof are provided.

In another aspect, the present invention related to nucleic acids, such as DNA or RNA, which enable us to express (i) a protein or a salt thereof, having an activity identical with or substantially equivalent to native human cathepsin L2 which (a) belongs to a member of papain family, and (b) is an enzyme having a cysteine proteinase activity but not human cathepsin L, (ii) more preferably a polypeptide or a salt (a) having a biological property or a primary structural conformation, identical with or substantially equivalent to human cathepsin L2 or a salt thereof, and (b) having at least part or all of the protein, in a prokaryotic cell such as *E. coli* or an eukaryotic cell such as a mammal cell.

In addition, such nucleic acids, particularly DNA, may include (a) sequences coding for an amino acid sequence represented by SEQ ID NO: 1 in Sequence Listing or sequences complementary thereto; (b) sequences capable of hybridizing with the DNA sequences (a) or fragments thereof; and (c) sequences having degenerate codons hybridizable with either of the sequences (a) and (b). The hybridization may be carried out under stringent conditions. The unique features of the present invention also reside in transformed prokaryotic cells, such as *E. coli*, and transformed eukaryotic cells, such as mammal cells, which are transformed with said nucleic acid and can express the polypeptides according to the present invention.

The antibodies, such as antisera and monoclonal antibodies, according to the present invention can be produced by immunizing animals with, as an immunogen, human cathepsin L2 obtained according to the present invention based on techniques known or widely applicable in the art. Examples of such techniques are found in G. Kohler & C. Milstein, Nature, 256: 495 to 497, 1975, etc., the disclosures of which are hereby incorporated by reference. In this technique, the antigen used may include any of naturally-occurring (native) human cathepsin L2, recombinant human cathepsin L2, synthetic peptides (or fragments derived from the human cathepsin L2 protein) having an amino acid sequence selected from the group consisting of low homologous regions (of human cathepsin L2) to other cysteine proteinases which belong to the papain family (e.g., synthetic peptides having an amino acid sequence composed of at least continuous 3 amino acids which are part of human cathepsin L2), etc. Examples of the synthetic peptide are those having an amino acid sequence composed of 4 to 250 amino acid residues, preferably 6 to 45 amino acid residues, and more preferably 10 to 35 amino acid residues. Any peptide can be employed as long as it has a sequence portion characteristic of human cathepsin L2. The portion may include propeptide areas in human cathepsin L2 (e.g., from the 18th to the 31st residues of SEQ ID NO: 1 in Sequence Listing (SEQ ID NO: 9), from the 91st to the 100th residues thereof (SEQ ID NO: 10), and neighboring regions thereof); areas comprising a propeptide cleavage site (e.g., from the 112nd to the 116th residues of SEQ ID NO: 1 in Sequence Listing (SEQ ID NO: 11), and neighboring regions thereof); active (mature) human cathepsin L2 areas (e.g., from the 205th to the 217th residues of SEQ ID NO: 1 in Sequence Listing (SEQ ID NO: 12), from the 226th to the 232th residues thereof (SEQ ID NO: 13), from the 287th to the 295th residues thereof (SEQ ID NO: 14), and neighboring regions thereof); etc.

The human cathepsin L2 can be obtained from in vivo or in vitro cathepsin L2-producing cells including cultured cells, excised tissues, cultured tissues, etc. The cathepsin L2 sources may include cells and tissues from thymus, testis, brain, intestine, kidney, etc.; breast cancers; breast carcinoma cell lines such as ZR-75-1, Hs-578T, and MDA-MB435; ovary cancers; colorectal adenocarcinoma SW480 cells; etc. The human cathepsin L2 can be recombinant. The recombinant human cathepsin L2 can be obtained by molecular cloning techniques using genes isolated and purified from human cathepsin L2-producing cells/tissues including cells and tissues from thymus, testis, and brain. Immunogens as used herein preferably include human cathepsin L2 prepared according to the present invention and derivatives thereof. Such human cathepsin L2 immunogens can be isolated and purified by well known techniques as aforementioned, from various sources including antigen-producing materials such as culture cells, culture tissues and transformed cells. Purified recombinant cathepsin L2 proteins are useful as immunizing antigens for producing monoclonal antibodies. Peptides can be synthesized based on information from the human cathepsin L2 gene obtained according to the present invention and suitably adapted to be employed as immunizing antigens for preparation of antibodies (e.g., monoclonal antibodies). The antibody (including the monoclonal antibody) can be labeled using conventional techniques. The labels (markers) may include enzymes, radioisotopes (radioactive substances), light-emitting substances such as chemiluminescent compounds, fluorescent substances, metal colloids, prosthetic molecules, pigment (chromophore) substances, biotin, etc.

Described herein below is the production of antibodies.

It goes without saying that the monoclonal antibody to be used in the present invention may be a monoclonal antibody obtained by utilizing cell fusion techniques with myeloma cells.

The monoclonal antibody to be used in the present invention can be produced by the following processes:

1. Preparation of immunogenic antigens (immunogens)
2. Immunization of animals with immunogenic antigens
3. Preparation of myeloma cells 4. Cell fusion between antibody-producing cells and myeloma cells
5. Selection and cloning of hybridomas (hybrid cells)
6. Production of monoclonal antibodies 1. Preparation of Immunogenic Antigens The antigen used includes recombinant human cathepsin L2 as prepared according to the present invention and suitable synthetic oligopeptides, chemically synthesized, based on information on sequenced human cathepsin L2. The human cathepsin L2 antigen may include human procathepsin L2 and active human cathepsin L2. Although the antigen may be used after formation of immunogenic conjugates, it can be used to immunize animals after being mixed with a suitable adjuvant without any modifications. For example, the antigen for such an immunogen may be a fragment derived from human cathepsin L2 or a synthetic polypeptide fragment obtained via selecting characteristic sequence areas based on amino acid sequences deduced from the cloned and sequenced cDNA followed by design and chemical synthesis. The fragments may be coupled with various carrier proteins via suitable coupling agents to form immunogenic conjugates such as hapten-proteins. The immunogenic conjugates can be used to design monoclonal antibodies that can react with (or recognize) specific sequences exclusively. A cysteine residue or the like can be added to the polypeptide thus designed so as to prepare an immunogenic conjugate easily. To couple with a carrier protein or the like, the carrier protein is first activated. This activation may include incorporation of an activated binding group thereinto, etc. The activated binding groups include (1) active ester or active carboxyl groups such as a nitrophenyl ester group, a pentafluorophenyl ester group, a 1-benzotriazol ester group, and an N-succinimido ester group; (2) active dithio groups such as a 2-pyridyldithio group, etc. The carrier proteins include keyhole limpet haemocyanin (KLH), bovine serum albumin (BSA), ovalbumin, globulin, polypeptides such as polylysine, bacterial components such as BCG or the like.

2. Immunization of Animals With Immunogenic Antigens

Animals can be immunized according to techniques as described in Shigeru MURAMATSU et al. ed., "Jikken Seibutsu Gaku Kouza 14, Men-eki Seibutsu Gaku (Lectures on Experimental Biology 14, Immunobiology)", Maruzen K. K., 1985; Nippon Seikagaku Kai (Biochemical Society of Japan) ed., "Zoku-Seikagaku Jikken Kouza 5, Men-eki Seikagaku Kenkyuho (Lectures on Biochemical Experiments (Second Series; 5), Methods for Immunological and Biochemical Study)", Tokyo Kagaku Dojin, Japan (1986); Nippon Seikagaku Kai (Biochemical Society of Japan) ed., "Shin-Seikagaku Jikken Kouza 12, Bunshi Men-eki Gaku III (Kougen-Koutai-Hotai) (New Lectures on Biochemical Experiments 12, Molecular Immunology III (Antigen-Antibody-Complement))", Tokyo Kagaku Dojin, Japan (1992); etc., the disclosures of which are hereby incorporated by reference. The adjuvant to be used with the antigen includes Freund's complete adjuvant, Ribi adjuvant, pertussis vaccine, BCG, lipid A, liposome, aluminium hydroxide, silica, etc. Immunization is carried out with animals, including mice such as BALB/c. The antigen dose is, for example, approximately 1 to 400 $\mu$g/animal for mice. Generally, the antigen is injected intraperitoneally or subcutaneously into a host animal, followed by additional immunization by repeated courses wherein intraperitoneal, subcutaneous or intravenous administrations are carried out approximately 2 to 10 times at 1- to 4-week intervals, preferably 1- to 2-week intervals. For immunization, BALB/c mice, as well as F1 mice between BALB/c mice and other mice, etc. can be used. As required, the degree of animal immunization can be assessed by constructing a system for measuring a titre of antibody and measuring the titre of an antibody. The antibody of the present invention may include those obtainable from such immunized animals, for example, anti-serum, polyclonal antibodies, etc.

3. Preparation of Myeloma Cells

Immortal cell strains (tumor cell lines) to be used for cell fusion can be selected from non-immunoglobulin-producing cell lines. The cell strains to be used for cell fusion may include, for example, P3-NS-1-Ag4-1 (NS-1, Eur. J. Immunol., 6: 511 to 519, 1976), SP-2/0-Ag14 (SP-2, Nature, 276: 269 to 270, 1978), mouse myeloma MOPC-21 cell line-derived P3-X63-Ag8-U1 (P3U1, Current topics in Microbiol. Immunol., 81:1-7, 1978), P3-X63-Ag8 (X63, Nature, 256: 495 to 497, 1975), P3-X63-Ag8-653 (653, J. Immunol., 123: 1548 to 1550, 1979), etc. 8-azaguanine resistant mouse myeloma cell lines can be sub-cultured in a medium for cell culture, such as Dulbecco's modified Eagle's medium (DMEM) or RPMI-1640 medium, supplemented with antibiotics such as penicillin, amikacin or the like, fatal calf serum (FCS) or the like and 8-azaguanine (for example, 5 to 45 $\mu$g/ml). The specified number of cell lines can be prepared by passage the normal medium two or five days before cell fusion. The cell lines to be used may be cultured on the normal medium after the frozen and preserved strains have been completely thawed at approximately 37° C. and have been washed on the normal medium such as RPMI-1640 three or more times, and the specified number of cell strains may be prepared.

4. Cell Fusion Between Antibody-producing Cells and Myeloma Cells

After animals such as mice are immunized according to the above step 2, their spleens are removed in two to five days from final immunization, and the spleen cell suspension is obtained. In addition to the spleen cells, lymph node cells at various sites of organisms can be obtained and used for cell fusion. The spleen cell suspension thus obtained and the myeloma cell strains obtained by the above step 3 are placed in a medium such as minimum essential medium (MEM), DMEM or RPMI-1640 medium, and an agent for cell fusion, such as polyethylene glycol, is added. A widely-used agent for cell fusion can be used, including inactivated HVJ: Hemagglutinating virus of Japan (Sendai virus). Preferably, 0.5 to 2 ml of 30 to 60% polyethylene glycol can be added. Polyethylene glycol with 1,000 to 8,000 in molecular weight can be employed, more preferably, polyethylene glycol between 1,000 and 4,000 in molecular weight. The preferred concentration of polyethylene glycol in the fusion medium is between 30 and 60%. As required, a small amount of dimethyl sulfoxide or the like is added to promote fusion. The ratio of spleen cells (lymphocytes) :myeloma cell lines to be used for fusion is preferably 1:1 to 20:1, and preferably falls between 4:1 and 7:1. The fusion reaction is conducted for 1 to 10 minutes, before the addition of a medium such as RPMI-1640 medium. Fusion reaction can be done several times. After fusion reaction, cells are separated by a centrifuge, then transferred to the selection medium.

5. Selection and Cloning of Hybridomas (Hybrid Cells)

The selection media include conventionally known "HAT medium", i.e., FCS-containing MEM, RPMI-1640 medium, etc., supplemented with hypoxanthine, aminopterin, and thymidine. The replacement method for the selection medium is to replenish an amount equivalent to the capacity dispensed to the medium plate on the following day, after which the medium is replaced by half an amount in HAT medium every one to three days. The replacement can be modified depending on situations. Eight to sixteen days after fusion, the medium may be replaced every one to four days with conventionally known "HT medium" wherein aminopterin is excluded from HAT medium. As a feeder cell, for example, mouse thymocyte can be used, which is sometimes effective.

The supernatant of the culture well with highly growing hybridoma is screened by using human cathepsin L2 or a peptide fragment thereof as an antigen or by using a labeled anti-mouse antibody for measuring target antibodies, with a measuring system such as radioimmunoassay (RIA), enzyme-linked immunosorbent assay (ELISA), fluorescence immunoassay (FIA) or by the fluorescence activated cell sorter (FACS), etc. The target antibody-producing hybridoma is cloned. Cloning is carried out by picking up colonies in the agar medium or by the limiting dilution. The limiting dilution is preferred. Cloning should be performed several times.

6. Production of Monoclonal Antibodies

The obtained hybridoma cells are cultured in a suitable growth medium such as FCS-containing MEM, RPMI-1640 medium or the like, and a desired monoclonal antibody can be obtained from the culture supernatant. Large amounts of monoclonal antibodies can be produced by propagating hybridomas as ascites tumors, etc. In this case, each hybridoma is implanted intraperitoneally in a histocompatible animal isogenic to an animal from which the myeloma cell is derived and is propagated. Or each hybridoma can be inoculated, for example, in nude mice, and propagated to produce the monoclonal antibody in the ascites of the animals. The produced monoclonal antibody can be collected from the ascetic fluid and obtained. Prior to implantation of hybridomas, the animal is pretreated intraperitoneally with mineral oils such as pristane (2,6,10,14-tetramethylpentadecane). After the pretreatment, the hybridoma can be propagated therein and the ascitic fluid can be harvested. The ascitic fluid can be used as a monoclonal antibody without purification or after purification by conventionally known methods, including salting out such as precipitation with ammonium sulfate, gel filtration with SEPHADEX™, ion exchange chromatography, electrophoresis, dialysis, ultrafiltration, affinity chromatography, high-performance liquid chromatography, etc. The isolated or purified products can be employed as monoclonal antibodies. Preferably, the monoclonal antibody-containing ascitic fluid is fractionated with ammonium sulfate and separated and purified by treatments with anion exchange gel such as DEAE-Sepharose, an affinity column such as protein A column, etc. More preferably, it is treated with affinity chromatography using immobilized antigens or antigen fragments (for example, synthetic peptides, recombinant antigen proteins or peptides, portions which the antibody can specifically recognize); affinity chromatography with immobilized protein A; etc.

It is possible to produce antibodies by recombinant DNA techniques wherein the antibody thus obtained in a large amount is sequenced and/or a nucleotide sequence coding for the antibody obtained from the hybridoma cell line is employed.

These antibodies may be treated with enzymes such as trypsin, papain, pepsin or the like and occasionally be subjected to reduction to produce antibody fragments including Fab, Fab', and F(ab')$_2$. These antibody fragments may be occasionally used.

The antibody to be labeled with a marker may include IgG fractions, and specific bonding fragments Fab' obtainable by reduction after pepsin digestion. The labels include enzymes (peroxidase, alkaline phosphatase, or β-D-galactosidase or the like), chemical substances, fluorescences, radioisotopes, or the like, as disclosed hereinbelow.

In the present invention, detection and measurement can be carried out by immunostaining including, for example, staining of tissues and cells, immunoassays including, for example, competitive immunoassay and non-competitive immunoassay, radioimmunoassay, ELISA, or the like. The detection and measurement can also be carried with or without B-F separation. Preferably, the detection and measurement is carried out by means of radioimmunoassay, enzyme immunoassay or sandwich assay. In the sandwich-type assay, one of the antibodies against human cathepsin L2 is detectably labeled. The other antibody capable of recognizing the same antigen is immobilized on a solid phase.

Incubation is carried out to sequentially react a sample to be assayed, labeled antibodies, and immobilized antibodies as required. After the non-binding antibodies are separated, the label is detected or measured. The amount of the measured label is proportional to the amount of antigen, i.e., human cathepsin L2. For this assay, simultaneous sandwich assay, forward sandwich assay, or reverse-sandwich assay or the like is called, based on the difference according to the addition sequence of the insolubilized antibody and the labeled antibody. For example, washing, stirring, shaking, filtration, pre-extraction for antigen, etc. is optionally adopted in the measurement process under specific conditions. The other measurement conditions such as specific regents, concentration of buffering solution, temperature or incubation time can vary according to the elements, such as concentration of the antigens in the sample or the nature of samples to be measured. Any person ordinary skilled in the art can suitably select and determine optimal conditions effective for each measurement while using the general experimentation and perform the selected measurement.

Various carriers on which antigens or antibodies can be immobilized are available in the art, and they can be arbitrarily and suitably selected in the present invention. For the immobilization, various carriers which can be used for antigen-antibody interactions are known. It goes without saying that any well-known carrier can be selected and used in the present invention. Preferred examples are inorganic materials including, for example, glass such as activated glass and porous glass, silica gel, silica-alumina, alumina, magnetized iron, magnetized alloy, etc.; organic high molecular substances including, for example, polyethylene, polypropylene, polyvinyl chloride, polyvinylidene fluoride, polyvinyl acetate, polymethacrylate, polystyrene, styrene/butadiene copolymer, polyacrylamide, cross-linked polyacrylamide, styrene/methacrylate copolymer, polyglycidyl methacrylate, acrolein/ethylene glycol dimethacrylate copolymer, etc., cross-linked albumin, collagen, gelatin, dextran, agarose, cross-linked agarose, natural or modified cellulose such as cellulose, microcrystalline cellulose, carboxymethylcellulose, cellulose acetate and the like, cross-linked dextran, polyamide such as nylon, polyurethane, polyepoxy resin and the like; those obtained by emulsifying polymerization thereof; cells, erythrocytes and the like; and those into which a functional group may be introduced, as required, by using a silane coupling agent.

Also included are solid materials such as filtration paper, beads, inner wall of test container such as test tube, titer plates, titer wells, glass cells, cells made of synthetic materials such as plastic resin cells, glass rods, rods made of synthetic materials, rods thickened or thinned at the end, rods whose end is round or flat, thin-plated rods, and surfaces thereof.

Antibodies can be coupled with these carriers, and preferably the monoclonal antibodies according to the present invention which are capable of specifically binding with human cathepsin L2, can be coupled therewith. Coupling between the carrier and those associated with these antigen-antibody interactions can be carried out by techniques including physical method such as adsorption; a chemical method using a coupling agent, etc. or an activated reactant; a method using a chemically interactional coupling.

The label may include enzymes, enzyme substrates, enzyme inhibitors, prosthetic groups, coenzymes, enzyme precursors, apoenzymes, fluorescent substances, pigments, chemical luminescent compounds, light-emitting substances, coloring substances, magnetic substances, metal particles such as gold colloids, radioactive substances and the like.

The enzyme may include dehydrogenases, oxidoreductases such as reductase and oxidase; transferases that catalyze the transfer of an amino, carboxyl, methyl, acyl, phosphate group or the like; hydrolases that hydrolyze an ester, glycoside, ether, peptide bond or the like; lyases; isomerases; ligases; and the like. Plural enzymes can be used in a conjugated form for detection (for example, enzymatic cycling may also be utilizable).

Typical radioactive isotopes for the label include [$^{32}$P], [$^{125}$I], [$^{131}$I], [$^{3}$H], [$^{14}$C], [$^{35}$S], and the like.

Typical enzymes for the label include peroxidases such as horseradish peroxidase; galactosidase such as $E.\ coli$ β-D-galactosidase; maleate dehydrogenase; glucose-6-phosphate dehydrogenase; glucose oxidase; gluocoamylase; acetylcholine esterase; catalase; alkaline phosphatase such as calf intestinal alkaline phosphatase and $E.\ coli$ alkaline phosphatase, and the like.

In the case where alkaline phosphatase is used, fluorescence or emitted light can be measured by using a substrate such as umbelliferone derivatives including 4-methylumbellipheryl phosphate; phenol phosphate derivatives including nitrophenyl phosphate; enzymatic cycling systems utilizing NADP; luciferin derivatives; dioxetane derivatives; and the like. It is also possible to use a luciferin/luciferase system.

When catalase is used, the reaction takes place with hydrogen peroxide to produce oxygen which can be detected with an electrode or the like. The electrode may be a glass electrode, an ionic electrode using an insoluble salt membrane, a liquid-membrane type electrode, a polymer membrane electrode and the like.

It is possible to replace the enzyme label with a biotin label and an enzyme-labeled avidin (streptoavidin).

For the label, a plurality of many different kinds of labels or markers can be used. In this case, it is possible to perform plural measurements continuously or discontinuously and/or simultaneously or separately.

According to the present invention, a signal can be formed by using a combination of 4-hydroxyphenylacetic acid, 1,2-phenylenediamine, tetramethylbenzidine, or the like, with horseradish peroxidase, by using a combination of umbelliferyl galactoside, nitrophenyl galactoside, or the like, with enzyme reagents such as β-D-galactosidase and glucose-6-phosphoric acid dehydrogenase. There can be further used those that are capable of forming a quinol compound such as hydroquinone, hydroxybenzoquinone or hydroxyanthraquinone, a thiol compound such as lipoic acid or glutathione, phenol derivatives or ferrocene derivatives by utilizing the action of enzymes.

The fluorescent substance and chemiluminescent compounds may include fluorescein isothiocyanate, Rhodamine derivatives such as Rhodamine B isothiocyanate, and tetramethyl Rhodamine isothiocyanate, dansyl chloride (5-(dimethylamino)-1-naphtalenesulfonyl chloride), dansyl fluoride, fluorescamine (4-phenylspiro[furan-2(3H),1'-(3'H)-isobenzofuran]-3,3'-dione), phycobiliprotein, acridinium salts, luminol compounds such as lumiferin, luciferase, and aequorin, imidazole, oxalic acid ester, rare earth chelate compounds, cumarin derivatives, etc.

The labelling can be accomplished by utilizing the reaction of a thiol group with a maleimide group, reaction of a pyridyldisulfide group with a thiol group, the reaction of an amino group with an aldehyde group, etc. Additionally, it can be selected from widely known methods, methods that can be easily put into practice by an artisan skilled in the art, or any of methods modified therefrom. The coupling agents used for producing the foregoing immunoconjugate or for coupling with carriers are also applicable and usable.

The coupling agents include, for example, formaldehyde glutaraldehyde, hexamethylene diisocyanate, hexamethylene diisothiocyanate, N,N'-polymethylene bisiodoacetamide, N,N'-ethylene bismaleimide, ethylene glycol bissuccinimidyl succinate, bisdiazobenzidine, 1-ethyl-3-(3-dimethylaminopropyl) carbodiimide, succinimidyl 3-(2-pyridyldithio)propionate (SPDP), N-succinimidyl 4-(N-maleimidometyl)cyclohexane-1-carboxylate (SMCC), N-sulfosuccinimidyl 4-(N-maleimidomethyl)-cyclohexane-1-carboxylate, N-succinimidyl (4-iodoacetyl)aminobenzoate, N-succinimidyl 4-(1-maleimidophenyl)butyrate, N-(ε-maleimidocaproyloxy)succinimide (EMCS), iminothiolane, S-acetylmercaptosuccinic anhydride, methyl-3-(4'-dithiopyridyl)propionimidate, methyl-4-mercaptobutyrylimidate, methyl-3-mercaptopropionimidate, N-succinimidyl-S-acetylmercaptoacetate, etc.

According to the assay of the present invention, substances to be measured can be made to react sequentially with labeled antibody reagents such as monoclonal antibodies labeled with enzymes or the like, and with antibodies coupled on a carrier, or all the members can be reacted with each other simultaneously. The order of adding reagents (members) may vary depending on the type of carrier system selected. In the case where beads such as sensitized plastics are used, the labeled antibody regents such as monoclonal antibodies labeled with enzymes or the like are first put in a suitable test tube, together with a sample including substances to be measured, followed by addition of the plastic beads. Measurement can be then carried out.

For quantitative measurements according to the present invention, the immunological measurement is applied. For the measurement, the solid phase carriers used may include various materials and shapes which can be selected from balls, microplates, sticks, microparticles, test tubes, and the like, made of polystyrene, polycarbonate, polypropylene, polyvinyl and other materials capable of adsorbing proteins such as antibodies.

The measurement can be carried out in a suitable buffer system so as to maintain in optimal pH (for example, between about pH 4 and 9). In particular, the preferred buffers may include acetate buffer, citrate buffer, phosphate buffer, Tris buffer, triethanolamine buffer, borate buffer, glycine buffer, carbonate buffer, Tris-hydrochloride buffer, etc. The buffers can be used optionally in a mixed form at an arbitrary rate. Preferably, the antigen-antibody interaction is carried out at a temperature between about 0 and 6° C.

The antibody (for example, monoclonal antibody, etc.) regents labeled with enzymes, the regents including antibodies coupled to a carrier, and samples to be measured can be incubated until equilibrium is reached. However, the reaction can be stopped after limited incubation by separating the solid phase from the liquid phase at a time well before the antigen-antibody interaction equilibrates, and the degree of the presence of labels such as enzymes in either of the liquid and solid phases can be measured. Measurement operation can be performed by using automated measuring instruments, and data can be measured by permitting a substrate to be converted by the action of enzymes and by detecting produced indication signals with a luminescence detector, a photo detector or the like.

In the antigen-antibody interaction, adequate means can be taken so as to stabilize regents to be used, samples to be measured, and labels such as enzymes, respectively, and/or to stabilize antigen-antibody interactions per se. Further, for eliminating non-specific reaction, reducing inhibitory influences acting thereon, and/or activating measurement reaction, proteins, stabilizers, surfactants, chelating agents or the like can be added to solutions which are incubated. The chelating agent is more preferably ethylenediamine tetraacetate (EDTA). The blocking techniques for preventing non-specific binding reaction, which techniques are generally employed in the art or well-known among the persons skilled in the art, may be employed. The blocking can be achieved by treatments with normal serum proteins, albumin, skim milk or the like from mammals, etc., fermented milk products, collagen, gelatin, or the like. These methods or techniques can be used without any limitation since the purpose is to prevent non-specific binding reaction.

The samples to be measured according to the present invention may include various types of solutions such as colloid solution, non-fluid samples and the like. Preferably, the samples are biological samples including, for example, thymus, testis, intestine, kidney, brain, breast cancer, ovary cancer, colonic/rectal cancer, blood, serum, plasma, articular fluid, cerebrospinal fluid, saliva, amniotic fluid, urine, any other humoral fluids, cell culture medium, tissue culture medium, tissue homogenate, biopsy samples, tissues, cells and the like.

In applying each of those immunometric assay (immunoassays) to the measurement of the present invention, it is not necessary to set up any special condition, operation, etc. therefor. An assay system for native human cathepsin L2 (a factor having a cysteine proteinase activity) of the present invention or human proteins having a substantially equivalent activity thereto may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed), "Radioimmunoassay", Kodansha, Japan, 1974; Hiroshi Irie (ed), "Radioimmunoassay; Second Series", Kodansha, Japan, 1979; Eiji Ishikawa et al. (ed), "Enzyme Immunoassay", Igaku Shoin, Japan, 1978; Eiji Ishikawa et al. (ed), "Enzyme Immunoassay" (Second Edition), Igaku Shoin, Japan, 1982; Eiji Ishikawa et al. (ed), "Enzyme Immunoassay" (Third Edition), Igaku Shoin, Japan, 1987; H. V. Vunakis et al. (ed.), "Methods in Enzymology", Vol. 70 (Immunochemical Techniques, Part A), Academic Press, New York (1980); J. J. Langone et al. (ed.), "Methods in Enzymology", Vol. 73 (Immunochemical Techniques, Part B), Academic Press, New York (1981); J. J. Langone et al. (ed.), "Methods in Enzymology", Vol. 74 (Immunochemical Techniques, Part C), Academic Press, New York (1981); J. J. Langone et al. (ed.), "Methods in Enzymology", Vol. 84 (Immunochemical Techniques, Part D: Selected Immunoassays), Academic Press, New York (1982); J. J. Langone et al. (ed.), "Methods in Enzymology", Vol. 92 (Immunochemical Techniques, Part E: Monoclonal Antibodies and General Immunoassay Methods), Academic Press, New York (1983); J. J. Langone et al. (ed.), "Methods in Enzymology", Vol. 121 (Immunochemical Techniques, Part I: Hybridoma Technology and Monoclonal Antibodies), Academic Press, New York (1986); etc.

Epitope-mapping can be performed by using the anti-cathepsin L2 antibodies (especially monoclonal antibodies) of the present invention. When the antibodies which recognize each epitope are used, detection and/or measurement of proenzymes, active enzymes, etc. can be achieved.

In a typical aspect, the present invention provides advantageous methods for detecting and/or separably or quantitatively measuring (assaying) a free pro-form or active-form of human cathepsin L2, a gene thereof, or a human cathepsin L2-producing cell in a sample or specimen to be tested, which comprise using a member selected from the group consisting of (1) human cathepsin L2 genes, and probes derived therefrom, (2) monoclonal antibodies against human cathepsin L2 and monoclonal anti-human cathepsin L2 antibodies immobilized on solid carriers, and, depending on necessity, inhibitors against human cathepsin L2; and reagent kits therefor. Accordingly, it is understood that each reagent which is included in reagent kits capable of detecting and/or separably or quantitatively assaying such a free pro-form or active-form of human cathepsin L2, gene thereof, or human cathepsin L2-producing cell is within the embodiment of the present invention without exception.

In a further aspect, the present invention provides methods for monitoring the role of cysteine proteinase enzymes involved in various normal cellular processes, including the turnover of intracellular proteins, prohormone activation, and bone remodeling; and a variety of diseases, disorders and pathological conditions such as Alzheimer's disease, pulmonary emphysema, rheumatoid arthritis, muscular dystrophy, osteoporosis, neurodegenerative disease, and cancer invasion and metastasis, which comprise using the aforementioned method for detecting and/or separably or quantitatively assaying a free pro-form or active-form of human cathepsin L2, a gene thereof, or a human cathepsin L2-producing cell; reagents therefor; and diagnosis agents related thereto. Accordingly, it is understood that the embodiment of the present invention encompasses various uses of the aforementioned reagents and/or diagnosis agents in the medical and/or physiological field and applications of the aforementioned reagents and/or diagnosis agents with the aim and end of researches on, analyses and/or assay of animal cells and tissues including human cells and tissues, such as tumors and cancers.

Since the human cathepsin L2 of the present invention or a salt thereof has a proteinase activity, it is presumed that the cathepsin L2 is an essential factor in processes, including the turnover of intracellular proteins, antigen-presentation, bone remodeling, and prohormone activation. Accordingly, it is thought that said proteins are useful in therapeutic treatments of human cathepsin L2-associated malfunction diseases, having pathological conditions including human cathepsin L2 aplasia, cathepsin L2 expression-deficiency, cathepsin L2 gene defects, etc. Thus, when a pharmaceutical preparation comprising a member selected from the group consisting of human cathepsin L2, mutants, modified substances and derivatives thereof is used, it will be possible to make patients bearing diseases caused by insufficient cathepsin L2 activity normal or healthy. Since the protein of the present invention is one of proteinases, it is useful for a pharmaceutical agent or drug such as a therapeutic and/or prophylactic agent or drug against a variety of diseases caused when the expression amount or proteinase activity of said protein decreases. The protein of the present invention is also useful for a pharmaceutical agent or drug such as a therapeutic and/or prophylactic agent or drug against various diseases caused when the proteolytic activity thereof decreases. For instance, when patients are symptomatic of an insufficient biological activity of intracellular human cathepsin L2 or of its abnormal activity due to the in vivo decrease or defect of human cathepsin L2, the patients will be treated by (A) administering the protein of the present invention and the like thereto, (B) administering the nucleic acid (such as DNA) of the present invention thereto to express in vivo the protein of the present invention and the like, or (C) implanting cells wherein the nucleic acid (such as DNA) of the present invention is expressibly incorporated thereinto, etc., thereby supplementing in vivo the protein of the present invention and the like with the aim of mitigating and/or removing the symptoms concerned.

The compounds, of the present invention, which promote (or enhance) human cathepsin L2 functions including biological activities such as proteinase actions, (human cathepsin L2 agonists or promoters) or a salt thereof are useful as pharmaceutical agents or drugs for therapeutic and/or prophylactic treatments of a great number of diseases, disorders and pathological conditions such as human cathepsin L2 malfunction symptoms, pulmonary emphysema, muscular dystrophy, osteoporosis, Alzheimer's disease, neuronal degenerative disease, rheumatoid arthritis, and cancer invasion and metastasis.

The compounds, of the present invention, which inhibit (depress, suppress, or repress) human cathepsin L2 functions including biological activities such as proteinase actions, (human cathepsin L2 antagonists or inhibitors) or a salt thereof are useful as pharmaceutical agents or drugs for therapeutic and/or prophylactic treatments of a great number of diseases, disorders and pathological conditions such as human cathepsin L2 hyperfunction, pulmonary emphysema, muscular dystrophy, osteoporosis, Alzheimer's disease, neuronal degenerative disease, rheumatoid arthritis, and cancer invasion and metastasis. For instance, human cathepsin L2 is active in the degradation of substrates for cysteine proteinases. Its action is inhibited by inhibitors specific to the cysteine proteinases. Accordingly, said inhibitors may be adapted to be employed as pharmaceutical agents or drugs for the treatment of diseases caused by over-degradation with cathepsin L2.

Thus, the proteins of the present invention, including human cathepsin L2, etc. are useful for agents for screening for either (1) promoting or enhancing compounds (agonists), or a salt thereof, which promote or enhance the function of each of the proteins of the present invention, including human cathepsin L2, etc. wherein the function may include biological actions thereof such as proteinase activity, or (2) inhibitory compounds (antagonists), or a salt thereof, which inhibit or suppress the same function.

Further, the present invention provides methods of screening for either (1) a promoting compound (agonist), or a salt thereof, which promotes the function of any of the protein of the present invention (including human cathepsin L2), a peptide fragment thereof, and a salt thereof, etc., wherein the function may include a biological action thereof such as proteinase activity, or (2) an inhibitory compound (antagonist), or a salt thereof, which inhibits the same function, which comprises using a member selected from the group consisting of the proteins of the present invention (including human cathepsin L2), peptide fragments thereof, and salts thereof.

For example, the screening comprises (i) contacting the protein of the present invention, a peptide fragment thereof, a salt thereof or the like (wherein a transformant or transfectant which expresses said protein may be included; it has hereinafter the same meaning) with a substrate, thereby obtaining a first assay;

(ii) contacting the protein of the present invention, a peptide fragment thereof, a salt thereof, or the like, with a substrate in the further presence of a test sample, thereby obtaining a second assay; and (iii) comparing said first assay and said second assay. In an embodiment of the screening, its biological activity (e.g., its proteinase activity, etc.) is measure and compared.

The substrates may be any as long as they are substrates of the proteins, etc. according to the present invention. Examples of the substrate are casein, collagen, synthetic oligopeptides, and a member selected from substances employed in order to measure and/or assay proteinase activity. Preferred examples thereof are fluorescent labeled synthetic peptide substrates for cysteine proteinases. Examples of such peptide substrates are benzyloxycarbonyl-L-phenylalanyl-L-arginine-7-amido-4-methylcoumarin (Z-Phe-Arg-AMC), etc. The substrates can be used without any modifications, or preferably after labeling with fluorochromes such as fluorescein, enzymes or radioactive substances.

The test samples include, for example, peptides, proteins, nonpeptide compounds, synthetic compounds, fermented products, plant extracts, tissue extracts such as animal tissue extracts, cell extracts, etc. Examples of test compounds as used for the test samples may include preferably inhibitors of cysteine proteinases, and compounds (especially synthetic compounds) having an inhibitory activity against the cysteine proteinase family. These compounds can be novel or known to the public. The screening is conducted according to conventional techniques for measuring proteinase activities, for example, by referring to the methods disclosed in Biochemistry, 32, pp.4330–4337 (1993), etc. It can also be performed by using various labels, buffers and suitable other reagents, etc. and according to the operations, etc., as described herein for the assays employing the antibodies according to the present invention. In the screening, it is possible to treat the proteins and the like according to the present invention with activators such as mercuric aminophenylacetate, and to convert their precursors or latent forms (proenzymes) into active forms thereof prior to the assay. The assay can usually be performed in buffer without any adverse effect on the reaction, including Tris-HCl buffer, phosphate buffer, etc., for example, at pH 4 to 10, preferably at pH 6 to 8.

For each of these screenings, by giving technical consideration ordinarily owned by persons skilled in the art to customary conditions and operations for each method, suitable assay systems may be constructed in connection with each of the proteins of the present invention (including human cathepsin L2), and proteins (or peptides) having a substantially equivalent activity thereto.

With details of those conventional techniques, a variety of reviews, reference books, etc. may be referred to. They are, for example, Methods in Enzymology, Vol. 1, 2, 5 & 6 (Preparation and Assay of Enzymes), Academic Press, New York, USA; ibid., Vol. 3 (Preparation and Assay of Substrates), Academic Press, New York, USA; ibid., Vol. 4 (Special Techniques for the Enzymologist), Academic Press, New York, USA; ibid., Vol. 19 (Proteolytic Enzymes), Academic Press, New York, USA; ibid., Vol. 45 (Proteolytic Enzymes, Part B), Academic Press, New York, USA; ibid., Vol. 80 (Proteolytic Enzymes, Part C), Academic Press, New York, USA; etc.

The compounds or salts thereof identified or obtained by the screening method or kit according to the present invention are those selected from the aforementioned test compounds, including peptides, proteins, nonpeptide compounds, synthetic compounds, fermented products, cell extracts, plant extracts, animal tissue extracts, etc. Such compounds are those which enhance or inhibit the function of the proteins according to the present invention. Salts of said compounds are, for example, pharmaceutically acceptable salts thereof, etc. Examples of such salts are those of inorganic bases, of organic bases, of inorganic acids, of organic acids, of basic or acidic amino acids, etc. Preferred examples of the inorganic base salts are alkaline metal salts such as sodium salts, and potassium salts; alkaline earth metal salts such as calcium salts and magnesium salts; aluminum salts, ammonium salts; etc. Preferred examples of the organic base salts are salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine, etc. Preferred examples of the inorganic acid salts are salts with hydrochloric acid, hydrobromic acid, sulfuric acid, phosphoric acid, etc. Preferred examples of the organic acid salts are salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc. Preferred examples of the basic amino acid salts are those of arginine, lysine, ornithine, etc. Preferred examples of the acidic amino acid salts are those of aspartic acid, glutamic acid, etc.

The compounds which promote or inhibit the function of each of the proteins of the present invention and the like, or a salt thereof, are useful as safe, non-toxic therapeutic and/or prophylactic agents against a variety of diseases and disorders, similarly to each of the aforementioned proteins, peptide fragments thereof and salts thereof according to the present invention. The application of the compounds obtained and identified by using the screening methods or screening kits of the present invention, or a salt thereof, to the aforementioned therapeutic and/or prophylactic agents can be carried out according to conventional techniques in a similar manner to that for the aforementioned proteins, peptide fragments thereof and salts thereof according to the present invention.

The active components of the present invention (e.g., (a) the proteins of the present invention, peptide fragments thereof, salts thereof, or the like; (b) the nucleic acids (including DNA, etc.) of the present invention, or the like; (c) the antibodies (including monoclonal antibodies) of the present invention or derivatives thereof wherein the antibodies are against any of the proteins of the present invention and peptide fragments thereof; (d) the antisense oligonucleotides of the present invention against any of the nucleic acids (including DNA, etc.) of the present invention; (e) the compounds which promote or inhibit the biological activity of the protein of the present invention, a peptide fragment thereof, or a salt thereof; etc.) can be employed as pharmaceutical agents usually in the form of a pharmaceutical composition or preparation alone or in admixture with a variety of pharmaceutically acceptable aids. For example, the proteins (including human cathepsin L2 and the like) of the present invention, peptide fragments thereof, salts thereof, etc. can be administered alone or in the form of a pharmaceutical composition or preparation in admixture with any of various pharmaceutically acceptable aids. Preferably, it may be administered in the form of a convenient pharmaceutical composition or formulation suitable for oral, topical, parenteral application, or the like. Any of dosage forms (including those for inhalation and rectal administration) may be selected depending on purpose.

The parenteral administration includes topical, percutaneous, intravenous, intramuscular, subcutaneous, intracutaneous, and intraperitoneal routes. It is also possible to apply the drug directly to affected sites, and, in a certain case, the direct application is suitable. Preferably mammal animals including human can receive the drug orally or parenterally (e.g., intracellularly, intra-tissularly, intravenously, intramuscularly, subcutaneously, intracutaneously, intraperitoneally, intrapleurally, intraspinally, by instillation, enterally, per rectum, by instillation into the ear, eye, or nose by swabbing or application on the teeth, skin or mucosa, etc.). Specific dosage forms of the pharmaceutical preparations and formulations include pharmaceutical solutions, pharmaceutical dispersions, semi-solid preparations, particulate preparations, shaped preparations, extractives, etc. Examples of the dosage forms are tablets, coated tablets, sugar coated tablets, pills, troches, hard capsules, soft capsules, microcapsules, implants, powders, pulvises, granules, fine granules, injections, liquids and solutions, elixirs, emulsions, irrigations, syrups, mixtures, suspensions, liniments, lotions, aerosols, sprays, inhalations, nebula, ointments, plasters, patches, pastes, cataplasms, creams, oleates, suppositories (e.g., rectal suppositories), tinctures, dermatologic waters, ophthalmic solutions, collunariums, auristillae, paints, transfusions, powders for injection solutions, lyophilized preparations, conditioned gels, etc.

The pharmaceutical compositions can be formulated in accordance with conventional techniques. For example, the pharmaceutical composition or formulation may comprise at least one of said compounds (active components) of the present invention or a salt alone or in admixture with physiologically allowable carriers, pharmaceutically acceptable carriers, adjuvants, vehicles, excipients, diluents, etc. The compound (active component) of the present invention or a salt thereof is usually admixed with a single member selected from the group consisting of physiologically allowable carriers, pharmaceutically acceptable carriers, adjuvants, vehicles, excipients, diluents, flavoring agents, perfuming agents, sweetening agents, expanders, antiseptics, stabilizers, binders, pH regulators, buffering agents, detergents (surfactants), bases, solvents, fillers, bulking agents, solution adjuvants, solubilizers, tonicity agents, emulsifiers, suspending agents, dispersers, viscosity-increasing agents, thickening agents, gelling agents, stiffening agents, absorbents, adhesives, elastomers, plasticizers, disintegrants, aerosol propellants, preservatives, antioxidants, opacifying agents, humectants, emollients, charge protectors, soothing agents, etc., or suitably in a combination thereof, depending on necessity, to give a unit dose form which is required for generally approved pharmaceutical practices.

Formulations suitable for parenteral routes include aseptic solutions or suspensions containing at least one active component in admixture with water or other pharmaceutically acceptable media. Examples of such parenteral formulations are injections. Preferred liquid carriers for injection generally include water, saline, dextrose solution, other related saccharide solutions, ethanol, glycols such as propylene glycol and polyethylene glycol, etc. For the preparation of injections, the active component of the present invention is usually admixed with any of carriers such as distilled water, Ringer's solution, physiological saline, suitable dispersing agents, moistening agents, suspending agents, etc. to form injectable formulations including solutions, suspensions, emulsions, etc. by known techniques in the art.

Examples of aqueous liquids for the injection are a physiological saline and isotonic solutions containing glucose and other aids (e.g. D-sorbitol, D-mannitol, sodium chloride, etc.) wherein a suitable pharmaceutically acceptable auxiliary solubilizer such as alcohol (e.g. ethanol, etc.), polyalcohol (e.g. propylene glycol, polyethylene glycol, etc.), nonionic surface-active agent (e.g. POLYSOBATE 80™, HCO-50, etc.), etc. may be jointly used. The injectable oily liquids may include sesame oil, soybean oil, etc. wherein benzyl benzoate, benzyl alcohol, etc. may be jointly used as auxiliary solubilizers. In addition, buffers (e.g. phosphate buffer, sodium acetate buffer, etc.) or agents for osmoregulation, analgesic agents (e.g. benzalkonium chloride, procaine hydrochloride, etc.), stabilizers (e.g. human serum albumin, polyethylene glycol, etc.), preservatives (e.g. benzyl alcohol, phenol, etc.), antioxidants such as ascorbic acid, absorbefacients, etc. may be compounded therewith too. The prepared injection solution is usually filled in suitable ampoules.

For parenteral administration, solution or suspension unit dosage forms are prepared in pharmaceutically acceptable sterile fluids such as water, ethanol, and oils, in admixture with or without detergent and other pharmaceutically acceptable aids. The oily vehicle and solvent used in the parenteral formulation may include natural, synthetic or semi-synthetic mono-, di-, or triglycerides; natural, semi-synthetic or synthetic fats and oils; and fatty acids. Examples of such oily vehicles and solvents are plant oils such as peanut oil, corn oil, soybean oil, and sesame oil. For example, this injection can usually be prepared to form unit doses each containing approximately from 0.1 to 10 parts of the compound of the present invention per 100 parts by weight of the dose composition. The formulation suitable for topical use, such as buccal or rectal application, includes mouthwashes and gargles, dentifrices, sprays for buccal cavity, inhalants, ointments (salves), dental fillers, dental coating agents, dental pastes, suppositories, etc. The mouthwashes and other dental agents are prepared by conventional techniques, using pharmaceutically acceptable carriers. For the sprays for buccal cavity and inhalants, the compound of the present invention can be applied to teeth, etc. after dissolving alone or together with pharmaceutically acceptable inert carriers, in an aerosol or solution for nebulizers, or in the form of powders for inhalation. The ointments (salves) are prepared by conventional techniques, in admixture with conventionally employed pharmaceutical bases such as ointment bases (white petrolatum, paraffin, olive oil, macrogol 400, macrogol ointment, etc.).

The pharmaceutical drugs for topical application (including painting) to teeth and skin can be prepared in the form of a solution or suspension utilizing suitably sterilized water or non-aqueous vehicles. The additives used include buffering agents such as sodium bisulfite and disodium edetate; preservatives including antiseptic, antimicrobial and antifungal agents such as acetic acid, phenylmercuric nitrate, benzalkonium chloride and chlorhexidine; and thickeners such as hypromellose.

The suppositories can be prepared by conventional techniques utilizing carriers well known in the art, preferably suitable non-irritative excipients. Examples of the excipients are those which are solid at room temperature but liquid at rectal temperature wherein such substances melt in the rectum to deliver a drug, such as polyethylene glycols, lanolin, cacao butter, and fatty acid triglycerides. In the suppositories, the compounds of the present invention are applied in the form of compositions containing approximately from 0.1 to 95 percent (weight per volume). The compound, depending on the vehicle and concentration used, can be either suspended or dissolved in the vehicle. Adjuvants such as a local anesthetic, preservative and buffering agent can be dissolved in the vehicle.

The formulations suitable for oral application include solid compositions such as tablets, pills, capsules, powders, granules, and troches; fluid compositions such as solutions, syrups, and suspensions; etc. In preparing oral formulations, pharmaceutical adjuvants known in the art are employed. The tablets and pills can be prepared further by enteric coating. When the unit dosage form is a capsule, fluid carriers such as fats and oils can be contained in addition to the aforementioned materials.

Further, for the therapeutic and/or prophylactic agents containing the nucleic acids (including DNA) of the present invention as aforementioned, said nucleic acid can be applied alone, or by ligation with suitable vectors used in genetic recombination techniques, including virus-derived vectors such as vectors derived from retrovirus.

The nucleic acids (including DNA) of the present invention can be administered by conventional known techniques, in unmodified forms or in forms formulated in admixture with suitable aids or physiologically acceptable carriers, for example, to promote transfer into intracellular compartments. The nucleic acids (including DNA) of the present invention can be presented for administration to humans and animals in pharmaceutical composition or preparations as aforementioned. For administration of the nucleic acids (including DNA) of the present invention, techniques known as gene therapy can also be applied.

Dose levels of said compound or a salt thereof may vary within a wide range. Specific dose levels and administration cycles for any particular patient will be employed depending upon a variety of factors including the activity of specific compounds employed, the sex, age, body weight, general health, diet, time of administration, route of administration, rate of excretion, drug combination, and the severity of the particular disease undergoing therapy.

For the manufacture of pharmaceutical compositions and preparations, the additives, etc., preparation methods and the like can be suitably selected from those disclosed in Nippon Yakkyokuho Kaisetsusho Henshu Iinkai (Ed.), "13th Ed. Nippon Yakkyokuho Kaisetsusho (Commentary on The Pharmacopoeia of Japan, 13th Ed.)", Jul. 10, 1996, Hirokawa Pub. Co., Tokyo, Japan; Hisashi Ichibagade et al. (Ed.), "Pharmaceutical Research and Development (Ikuo Suzuki, chief editor), Volume 12 (Pharmaceutical Necessities 1)", Oct. 15, 1990, Hirokawa Pub. Co., Tokyo, Japan; ibid., Volume 12 (Pharmaceutical Necessities 2), Oct. 28, 1990, Hirokawa Pub. Co., Tokyo, Japan; etc., depending on necessity, and can be adapted by referring to the disclosures therein.

Through utilization of the aforementioned various modes of the present invention, there are provided not only examining and measuring means (including reagents and devices) useful for and effective in studies on diagnosis, etc. with regard to a variety of pathological conditions, diseases, and disorders, such as Alzheimer's disease, pulmonary emphysema, rheumatoid arthritis, muscular dystrophy, osteoporosis, neurodegenerative disease, and cancer invasion and metastasis, but also a variety of technical means adaptable to other medical and physiological applications.

For terms (words) and/or abbreviations used in the specification and in the drawings, they must conform with an "IUPAC-IUB Commission on Biochemical Nomenclature" or are based on the meanings of the terms which are commonly used in the art. Abbreviations as listed below are principally used hereinbelow:

bp: base pair(s);

E-64: trans-epoxysuccinyl-L-leucylamido-(4-guanidino) butane;

EST: expressed sequence tag; GST: glutathione S-transferase;

IPTG: isopropyl-1-thio-β-D-galactopyranoside;

PAGE: polyacrylamide gel electrophoresis;

PCR: polymerase chain reaction; SDS: sodium dodecyl sulfate;

Z-Phe-Arg-AMC: benzyloxycarbonyl-L-phenylalanyl-L-arginine-7-amido-4-methylcoumarin.

The clone 5.1.1 (which has a nucleotide sequence coding for human cathepsin L2), designated Clone 5.1.1, obtained in Example 2 mentioned hereinbelow has been deposited as from May 20, 1998 (original deposit date) with the National Institute of Bioscience and Human Technology (NIBH), Agency of Industrial Science and Technology, Ministry of International Trade and Industry, Japan, located at 1-3, Higashi 1-chome, Tsukuba-shi, IBARAKI (zip Code: 305–8566), JAPAN and has been assigned the Accession Number FERM P-16811. The original deposit of the clone 5.1.1 has been transferred to one under the Budapest Treaty by a request dated February 8, 1999 and is on deposit with the Accession Number FERM BP-6640 under the terms of the Budapest Treaty at NIBH.

The transformant *Escherichia coli* DH5α (wherein plasmid pGEX-3X CathL2 constructed by ligation of human cathepsin L2-coding nucleotide sequence with expression vector pGEX-3X (Pharmacia LKB) is harbored), designated pGEX-3X CathL2, obtained in Example 3 mentioned hereinbelow has been deposited as from May 20, 1998 (original deposit date) with NIBH and has been assigned the Accession Number FERM P-16812. The original deposit of the transformant *E. coli* DH5α (pGEX-3X CathL2) has been transferred to one under the Budapest Treaty by a request dated Feb. 8, 1999 and is on deposit with the Accession Number FERM BP-6641 under the terms of the Budapest Treaty at NIBH.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

All the examples were carried out or can be carried out, unless otherwise disclosed specifically, by standard techniques which are well known and conventional to persons skilled in the art. Specific operations, treatment conditions, etc. in examples as described herein below are conducted or selected, unless otherwise specified, according to techniques disclosed in, for DNA cloning, J. Sambrook, E. F. Fritsch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to 4, (The Practical Approach Series), IRL Press, Oxford University Press (1995); particularly for PCR, H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990). When commercially available reagents and kits are used, protocols, drugs, etc. attached thereto are employed herein.

Example 1

Screening of a Human Brain cDNA Library

After searching the GENBANK™ database of human expressed sequence tags (ESTs) for sequences with homology to human cysteine proteinases, a mouse cDNA sequence (AA013726; deposited by M. Marra et al., WashU-HHMI Mouse EST Project) was identified that, when translated, showed a significant similarity to amino acid sequences previously determined for other cathepsins.

This DNA fragment was obtained by PCR amplification of cDNA from mouse embryo and brain cDNA libraries, as disclosed herein below. Total λ gt11-phage DNA from two commercially available mouse libraries (total embryo and brain, Clontech (Palo Alto, Calif.)) was screened for the presence of the EST, AA013726, using two specific primers, 5'-ATGTGGCTCTTGTTGGGCTT (primer m1; SEQ ID NO: 3), and 5'-GCCTCAGCTTCAAGACCTT (primer m2; SEQ ID NO: 4), derived from the AA013726 sequence. The λ gt11-phage DNA libraries was used as a template for the PCR.

Oligonucleotides for the primers were synthesized by the phosphoramidite method in an Applied Biosystems DNA synthesizer (model 392 A) and used directly after synthesis.

The PCR reaction was carried out in a GENEAMP™ 2400 PCR system from Perkin-Elmer/Cetus for 35 cycles of denaturation (94° C., 15 sec), annealing (56° C., 15 sec), and extension (72° C., 30 sec).

The PCR product of approximately 200 bp was phosphorylated with T4 polynucleotide kinase (Boehringer Mannheim) and cloned into an EcoRV-cut pBS vector (EcoRV, Boehringer Mannheim). The cloned cDNA was sequenced and found to be identical to the AA013726 sequence. This cDNA was then excised from the vector, radiolabeled and used to screen a human brain cDNA library (Clontech) according to standard procedures.

Double-stranded DNA probes were radiolabeled with [α-$^{32}$P]dCTP (3000 Ci/mmol) from Amersham using a commercial random-priming kit purchased from Pharmacia LKB.

Hybridization to the radiolabeled probe was carried out for 18 h in 6×SSC (1×SSC=150 mM NaCl and 15 mM sodium citrate, pH 7.0), 5×Denhardt's solution (1×Denhardt's solution=0.02% bovine serum albumin (BSA), 0.02% polyvinyl pyrrolidone, and 0.02% Ficoll), 0.1% SDS, and 100 μg/mL denatured herring sperm DNA at 55° C. The membranes were washed twice for 1 h at 55° C. in 2×SSC and 0.1% SDS and exposed to XAR-5 film (Kodak) at −70° C. with intensifying screens. Upon screening of approximately 1×10$^6$ plaque-forming units, DNA was isolated from 15 independent clones showing positive hybridization with the probe. After plaque purification, several cloned inserts were excised by EcoRI (Boehringer Mannheim) digestion, and the resulting fragments were subcloned into the EcoRI site of pUC18.

Example 2

Nucleotide Sequence Analysis

The fifteen DNA inserts cloned from the human brain cDNA library in Example 1 were excised for sequencing. DNA fragments selected for nucleotide sequencing were inserted into the polylinker region of phage vector M13mp19 and sequenced by the dideoxy chain termination method using either M13 universal primer or cDNA-specific primers and the Sequenase Version 2.0 kit (U.S. Biochemicals). All nucleotides were identified in both strands. Computer analysis of DNA and protein sequences was performed with the Genetics Computer Group software package of the University of Wisconsin Genetics Computer Group.

An analysis of the resulting sequences revealed that all but one clone corresponded to human cathepsin L, whereas the remaining clone (called "5.1.1") had a sequence similar to but distinct from any of those reported for this cysteine proteinase family (Gal, S., et al., Biochem. J., 253: 303–306, 1988). The present sequence was also different from those derived from genomic clones for three cathepsin L-like genes or pseudogenes identified in chromosome 10 (Bryce, S. D., et al., Genomics, 24: 568–576, 1994). The clone 5.1.1 has been deposited as from May 20, 1998 (original deposit date) with the National Institute of Bioscience and Human Technology (NIBH), Agency of Industrial Science and Technology, Ministry of International Trade and Industry, Japan, located at 1–3, Higashi 1-chome, Tsukuba-shi, IBARAKI (zip Code: 305–8566), JAPAN and has been assigned the Accession Number FERM P-16811. The original deposit of the clone 5.1.1 has been transferred to one under the Budapest Treaty by a request dated Feb. 8, 1999 and is on deposit with the Accession Number FERM BP-6640 under the terms of the Budapest Treaty at NIBH.

The nucleotide sequence of the approximately 1.3 kb insert of the positive clone 5.1.1, together with the amino acid sequence encoded by an open reading frame (ORF) included in said sequenced fragment, is shown in FIGS. 1(A) and 1(B) and in SEQ ID NO: 15 of the Sequence Listing. The putative amino acid sequence derived from said ORF is also shown in SEQ ID NO: 1 of the Sequence Listing. A protein encoded by the fragment is composed of 334 amino acids and has a predicted molecular weight of 37,369 (wherein a molecular weight of saccharide chains to be added is excluded).

Figure 2B:
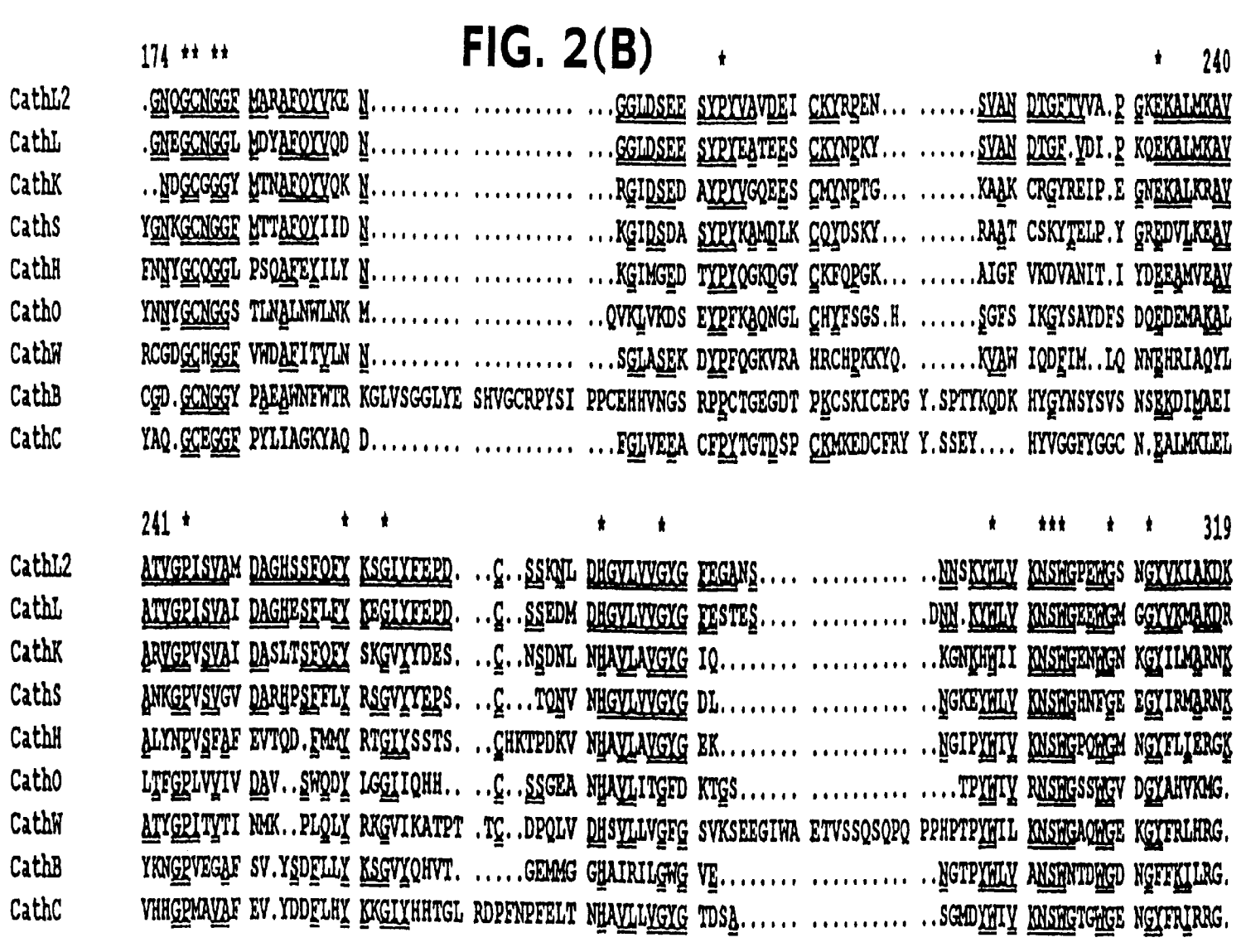

An amino acid sequence comparison between the identified amino acid sequence and those from other human cysteine proteinases showed that the percentage of identity ranged from 78% with procathepsin L to 20% with procathepsin C. On the basis of this high degree of sequence similarity with cathepsin L, this new cysteine proteinase family member is named "cathepsin L2". A multiple amino acid sequence alignment of cathepsin L2 with other human cysteine proteinases (cathepsins L, K, S, H, O, W, B and C) is shown in FIGS. 2(A), 2(B) and 2(C), wherein numbering corresponds to the sequence of cathepsin L2, on the basis of their amino acid sequence homology.

The deduced amino acid sequence for cathepsin L2 exhibits all of the structural characteristics typical of the other cysteine proteinases of the papain family. Thus, the finding of a stretch of hydrophobic amino acids close to the initial methionine suggests the presence of the signal peptide that is also present in the remaining cysteine proteinases of the papain family. The consensus sequence Ala-X-Ala is located at the end of said signal peptide sequence. Upon cleavage at position 17–18 of this signal sequence, after the consensus sequence Ala-X-Ala, the resulting procathepsin L2 protein would be composed of 317 amino acid residues with a predicted molecular weight of 35,693 (wherein a molecular weight of saccharide chains to be added is excluded).

The alignment of cathepsin L2 with the remaining cysteine proteinases also allows us to identify a proregion and a mature proteinase sequence and to define the putative cleavage site between both protein domains. In fact, as can be deduced from FIGS. 2(A), 2(B) and 2(C), the $NH_2$ terminus of most mature cysteine proteinases can be precisely aligned, because the second amino acid is proline in all cases (as indicated by an arrow). By analogy with them, the active processed form of cathepsin L2 would start at the leucine residue located at position 114, with a predicted molecular weight of 24,130 (wherein a molecular weight of saccharide chains to be added is excluded).

The putative cathepsin L2 has the active site Cys residue (at position 138) as well as other residues proposed to be important in the catalytic mechanism of cysteine proteinases, including the His-277 and Asn-301 residues, which would complete the catalytic triad of these enzymes. The amino acid sequences surrounding these three residues are also very well conserved in cathepsin L2 when compared with the remaining cathepsins. Thus, the $NH_2$-terminal region contains the glutamine residue (at position 132) of the putative oxyanion hole as well as the tryptophan residue and the hydrophobic segment immediately adjacent to the cysteine active site characteristic of these proteolytic enzymes.

In addition, the COOH-terminal region contains a series of conserved aromatic residues and the tripeptide Asn-Ser-Trp located in the active site. Human cathepsin L2 contains three potential sites of N-glycosylation located at positions 2, 221 and 292. It is noteworthy that only the glycosylation site at position 221 is conserved in cathepsin L. Because all mammalian cysteine proteinases characterized to date are glycosylated, it is presumed that at least one of these residues has attached the phosphomannosyl moieties required for lysosomal targeting via the mannose 6-phosphate receptor system.

Finally, the amino acid sequence deduced for cathepsin L2 contains six cysteine residues that are highly conserved in members of the cysteine proteinase family and have been found to form three disulfide bonds in papain and cathepsin B. In summary, considering all these structural characteristics together, it can be concluded that cathepsin L2 is a novel human cysteine proteinase of the papain family that exhibits an amino acid sequence markedly similar to that of cathepsin L.

This nucleotide sequence has been registered with GENBANK™/EMBL Data Bank under accession number Y14734.

Example 3

Construction of Expression Vectors and Expression in *E. coli*

A 669-bp DNA fragment containing the coding sequence for mature human cathepsin L2 was obtained by PCR amplification of the isolated full-length cDNA with primers:

5'-ATGCTTCCCAAATCTGTGGATTGG (primer L2-1; SEQ ID NO: 5) and

5'-TCACACATTGGGGTAGCTGG (primer L2-2; SEQ ID NO: 6).

Because of the design of the 5' primer, the amplified fragment contained the coding information for a methionine residue at the $NH_2$-terminal end. The PCR reaction was carried out for 30 cycles of denaturation (95° C., 30 sec), annealing (60° C., 30 sec), and extension (72° C., 1 min) using the Expand™ Long Template PCR System (Boehringer Mannheim) to reduce error frequency.

The PCR product was phosphorylated with T4 polynucleotide kinase (Boehringer Mannheim), repaired with Klenow fragment (Boehringer Mannheim), and ligated to expression vector pGEX-3X (Pharmacia LKB), which was previously treated with SmaI and alkaline phosphatase (Boehringer Mannheim). The resulting plasmid, called "pGEX-3X CathL2", was introduced into E. coli strain BL21 (DE3), and the transformed cells were grown in LB broth containing 100 μg/mL ampicillin at 37° C. for about 16 hrs, then diluted 1:100 with the same medium and grown to an $A_{600}$ of 1.0. Then, isopropyl-1-thio-β-D-galactopyranoside (IPTG) was added to a final concentration of 1 mM, and the incubation was continued for 3 hrs. Cells were collected by centrifugation, washed and resuspended in 0.05 volume of PBS, lysed by a French press, and centrifuged at 20,000×g for 20 min at 4° C. The soluble extract was treated with glutathione-Sepharose 4B and eluted with glutathione elution buffer (50 mM Tris-HCl buffer, pH 8.0 containing 10 mM reduced glutathione).

The E. coli extracts and purified recombinant proteins were analyzed by SDS-PAGE. As seen in FIG. 3(A), the bacteria (E. coli) transformed with the recombinant plasmid (pGEX-3X CathL2) contained a fusion protein of approximately 52 kDa that was not present in the control E. coli extracts wherein the control E. coli was transformed with the control plasmid (pGEX-3X). FIG. 3(A) also shows a band 29 kDa in the control extracts corresponding to the parental glutathione S-transferase (GST). Purified recombinant fusion cathepsin L2 was leading to a single band of the expected size (approximately 52 kDa) as assessed by SDS-PAGE. Similarly, Escherichia coli DH5α was transformed with the recombinant plasmid, pGEX-3X CathL2. The transformed E. coli DH5α with plasmid pGEX-3X CathL2 has been deposited as from May 20, 1998 (original deposit date) with the National Institute of Bioscience and Human Technology (NIBH), Agency of Industrial Science and Technology, Ministry of International Trade and Industry, Japan, located at 1-3, Higashi 1-chome, Tsukuba-shi, IBARAKI (Zip Code: 305-8566), JAPAN and has been assigned the Accession Number FERM P-16812 (Identification Reference to Microorganism: pGEX-3X CathL2). The original deposit of the transformant (pGEX-3X CathL2) has been transferred to one under the Budapest Treaty by a request dated Feb. 8, 1999 and is on deposit with the Accession Number FERM BP-6641 under the terms of the Budapest Treaty at NIBH.

Example 4

Enzyme Assays for Recombinant Cathepsin L2

The enzyme activity of purified cathepsin L2 produced in E. coli was measured by using 20 μM Z-Phe-Arg-AMC or Z-Arg-Arg-AMC (Bachem) as the substrate and following the procedure described by Barrett and Kirschke (Barrett, A. J., et al., Methods Enzymol., 80: 535–561, 1981) with minor modifications. Assays were performed at 30° C. in 100 mM sodium acetate buffer (pH 4.5) containing 10 mM dithiothreitol (DTT) and 2 mM EDTA. Substrate hydrolysis was monitored in a Cytofluor 2350 fluorometer (Millipore) at excitation and emission wavelengths of 360 and 460 nm, respectively. For inhibition assays, the reaction mixture containing recombinant cathepsin L2 was preincubated with 20 μM E-64 (Sigma) at 30° C. for 15 min, and the remaining activity for recombinant cathepsin L2 was determined using the fluorogenic substrate Z-Phe-Arg-AMC as described herein previously. As a positive control of enzyme assays, recombinant cathepsin O produced in E. coli (Velasco, G., et al., J. Biol. Chem., 269: 27136–27142, 1994) was used.

Figure 3B:
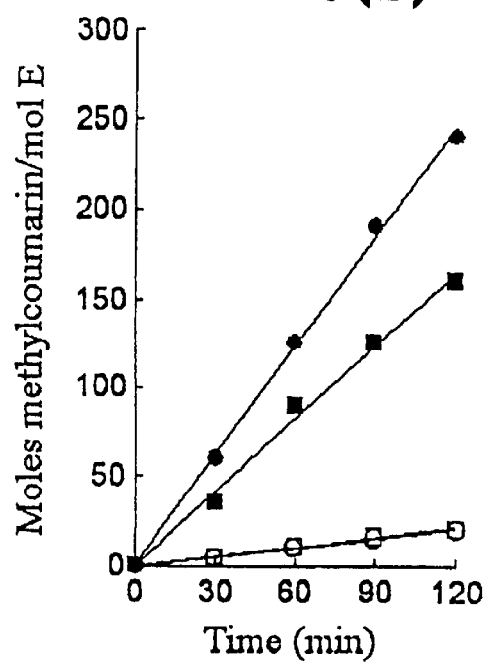

As could be anticipated from the similarity of its sequence to that of cathepsin L, recombinant cathepsin L2 exerted a significant proteolytic activity against the synthetic peptide Z-Phe-Arg-AMC, which is an optimal substrate for cathepsin L (FIG. 3B). The proteolytic activity was also similar to that corresponding to human cathepsin O produced in E. coli (FIG. 3(B)). In contrast, similar to the case of cathepsin L, the activity of recombinant cathepsin L2 against the fluorogenic substrate Z-Arg-Arg-AMC was very low.

In FIG. 3(B), each symbol refers to the following:
○: recombinant cathepsin L2 in the presence of E-64
●: recombinant cathepsin L2 in the absence of E-64
□: cathepsin O in the presence of E-64
■: cathepsin O in the absence of E-64

Furthermore, the proteolytic activity of cathepsin L2 against Z-Phe-Arg-AMC was abolished by E-64, an inhibitor which specifically inhibits cysteine proteinases, but was not abolished by inhibitors of metalloproteinases (EDTA), serine-proteinases (phenylmethylsulfonyl fluoride), and aspartyl-proteinases (pepstatin A)(FIG. 3(B)). These enzymatic analyses clearly indicate that cathepsin L2 is a functional cysteine proteinase with a substrate specificity similar to that of cathepsin L and an inhibitor profile characteristic of the family of cysteine proteinases.

Similarly, compounds which inhibit the enzymatic activity of cathepsin L2 can be screened. Such inhibiting compounds may include peptides, proteins, nonpeptide compounds, synthetic compounds, components included in fermented products, plant/animal-tissue/cell extracts, plant/animal-tissue/cell homogenates, blood, serum, plasma, etc. These compounds may be novel or well known.

Example 5

Analysis of Cathepsin L2 Expression in Normal and Tumor Tissues

Northern blots containing 2 μg of poly(A)[30] RNA from different human tissue specimens and cancer cell lines or 20 μg of total RNA isolated from paired human colorectal carcinomas and adjacent normal tissue were analyzed. The Northern blots were prehybridized at 42° C. for 3 hrs in 50% formamide, 5×SSPE (1×SSPE=150 mM NaCl, 10 mM $NaH_2PO_4$, and 1 mM EDTA, pH 7.4), 10×Denhardt's solution, 2% SDS, and 100 μg/ml denatured herring sperm DNA. After prehybridization, filters were hybridized with a 270-bp radio-labeled probe corresponding to the 3' untranslated region of the cathepsin L2 cDNA obtained from digestion of the full-length cDNA with FokI and EcoRI. The same filters were also hybridized with a 797-bp fragment corresponding to positions 550–1347 of cathepsin L cDNA (Gal, S., et al., Biochem. J., 253: 303–306, 1988). After hybridization, the filters were washed with 0.1×SSC and 0.1% SDS for 2 hrs at 50° C. and exposed to autoradiography.

Probes commonly used for expression analysis of cathepsin L cross-hybridize with cathepsin L2. Accordingly, the probes specific for cathepsin L2, as used herein, are quite useful and effective because they allow us to not only detect cathepsin L2 transcripts but also distinguish such transcripts from cathepsin L transcripts.

Figure 4:
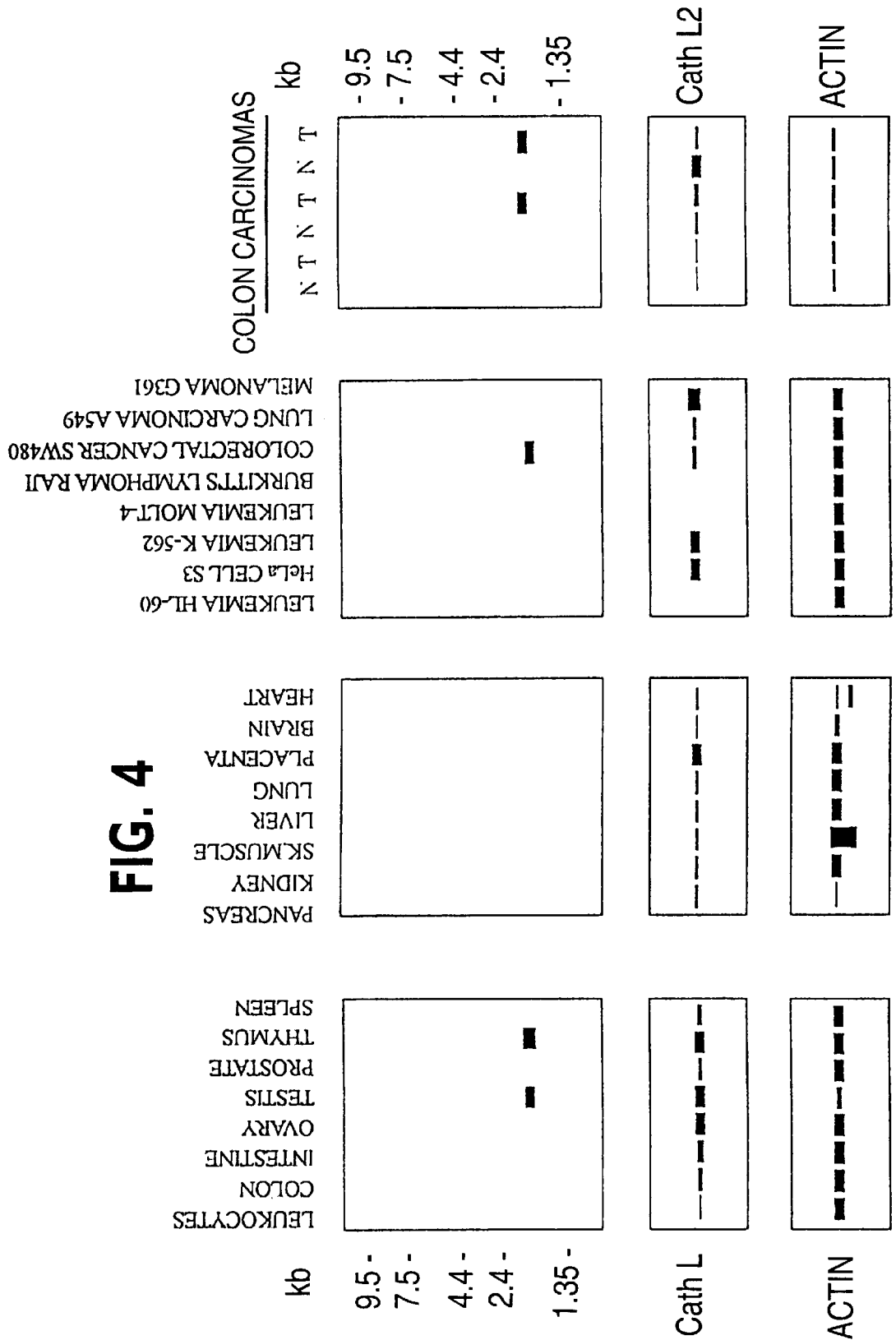
FIG. 4 is northern blot analysis of cathepsin L2 mRNA in human tissues, cancer cell lines, and colorectal carcinomas. Two μg of poly(A)$^+$ RNA prepared from the indicated tissues and cell lines or 20 μg of total RNA from paired colorectal carcinomas (T) and adjacent normal tissue (N) were analyzed by hybridization with a 270-bp probe corresponding to the 3' end untranslated region of the cDNA for human cathepsin L2. The positions of RNA size markers are shown. Filters were subsequently hybridized with a human cathepsin L probe (Cath L) and finally with a human actin probe.

This Northern blot analysis revealed the presence of a single transcript of approximately 1.8 kb (FIG. 4) that was strongly expressed in the thymus and testis. Longer exposure of membranes (against radioactive labels) led to the appearance of very low levels of the same cathepsin L2 transcript in other tissues, including the brain and intestine. By contrast, hybridization of the same membranes with a probe specific for cathepsin L confirmed the widespread distribution of this enzyme (cathepsin L) in human tissues (FIG. 4). The finding of a preferential expression of cathepsin L2 in the thymus and testis is a unique feature of this novel enzyme when compared with all human cysteine proteinases of the papain family described thus far. In fact, most members of this gene family including cathepsins B, L, H, C, and O are widely expressed in human tissues, which is consistent with a role for these enzymes in the intracellular protein degradation that takes place in lysosomes of all cell types.

Interestingly, recent findings have suggested that in addition to their housekeeping role as lysosomal enzymes, some cathepsins may play highly specific roles in those tissues in which they are overexpressed or even exclusively expressed. This is the case with the recently described cathepsins K, S, and W, which are produced by osteoclasts (Inaoka, T., et al., Biochem. Biophys. Res. Commun., 206: 89–96, 1995; Gelb, B. D., et al., Science, 273: 1236–1238, 1996), lymphatic tissues (Shi, G. P., et al., J. Biol. Chem., 267: 7258–7262, 1992), and T-lymphocytes (Linnerves, C., et al., FEBS Lett., 405: 253–259, 1997), respectively and have been proposed to be involved in bone remodeling (cathepsin K), antigen presentation (cathepsin S), and regulation of T-cell cytolytic activity (cathepsin W).

At present, the specific function of cathepsin L2 remains speculative, but its predominant expression in thymus suggests that it has a role related to the immune system, whereas its high level of expression in the testis suggests that it has a putative role in fertilization processes.

Cathepsin L2's close structural similarity to cathepsin L, which is also known as the major excreted protein of malignantly transformed fibroblasts (Gal, S., et al., J. Biol. Chem., 261: 1760–1765, 1986), indicated the possibility that this novel cysteine proteinase could be involved in tumor processes as reported for cathepsin L (Berquin, I. M., et al., Perspect. Drug. Discov. Des., 2: 371–388, 1994; Chauhan, S. S., et al., Cancer Res., 51: 1478–1481, 1991). For examining the relationship between cathepsin L2 and tumor processes, Northern blots containing poly(A)+ RNA extracted from different cancer cell lines (leukemia HL-60, HeLa cell S3, leukemia K-562, leukemia MOLT-4, Burkkit's lymphoma Raji, colorectal adenocarcinoma SW480, lung carcinoma A549, and melanoma G361) were hybridized with a probe specific for cathepsin L2. As seen in FIG. 4, a transcript of the expected size (approximately 1.8 kb) was detected exclusively in colorectal adenocarcinoma SW480 cells. By contrast, it was also shown that cathepsin L is expressed in most of the tumor cell lines that were analyzed (FIG. 4). Northern blot analysis was conducted for total RNA isolated from paired primary colorectal carcinomas and adjacent normal mucosa. The Northern blot analysis revealed that cathepsin L2 transcripts were detected in a significant number of colorectal carcinomas (6 of 10) but not in paired adjacent normal tissue. FIG. 4 shows a representative Northern blot displaying one negative case and two colorectal carcinomas expressing cathepsin L2 in the tumor tissue but not in the paired adjacent normal colonic mucosa. Regarding an analysis of cathepsin L expression in the same samples, it was observed that, in at least one case, cathepsin L expression was higher in normal mucosa than in its paired tumor tissue.

Example 6

Reverse Transcription and PCR Amplification of RNA from Human Carcinomas and Cancer Cell Lines A trial of detecting the expression of human cathepsin L2 of the present invention was conducted by RT-PCR techniques for breast carcinomas, which have been reported to produce significant amounts of cathepsin L (Berquin, I. M., et al., Perspect. Drug. Discov. Des., 2: 371–388, 1994; Lah, T. T., et al., Breast Cancer Res. Treatm., 39: 221–233, 1996).

Total RNA was isolated from a variety of human carcinomas and breast cancer cell lines (T-47D, ZR-75-1, Hs-578T and MDA-MB435) by guanidinium thiocyanate-phenol chloroform extraction and used for cDNA synthesis with the RNA PCR kit from Perkin-Elmer/Cetus.

After reverse transcription using 4 µg of total RNA as a template and random hexamers as primers, the whole mixture was used for PCR with two oligonucleotides specific for human cathepsin L2 (5'-CTTAAGGACAGCATGTCTGGGGAA; primer L2-3, SEQ ID NO: 7 and 5'-AGTCTTTGATATCATAAAGCTGTG; primer L2-4, SEQ ID NO: 8).

The PCR reaction was carried out in a GENEAMP™ 2400 PCR system (Perkin-Elmer) for 40 cycles of denaturation (94° C., 15 sec), annealing (60° C., 15 sec), and extension (72° C., 15 sec) to amplify a 184-bp fragment corresponding to nucleotides 1100 to 1283 of cathepsin L2 cDNA. The PCR products were analyzed in 2.5% agarose gels. Negative controls were also similarly performed in all cases by omitting the template or reverse transcriptase.

Figure 5:
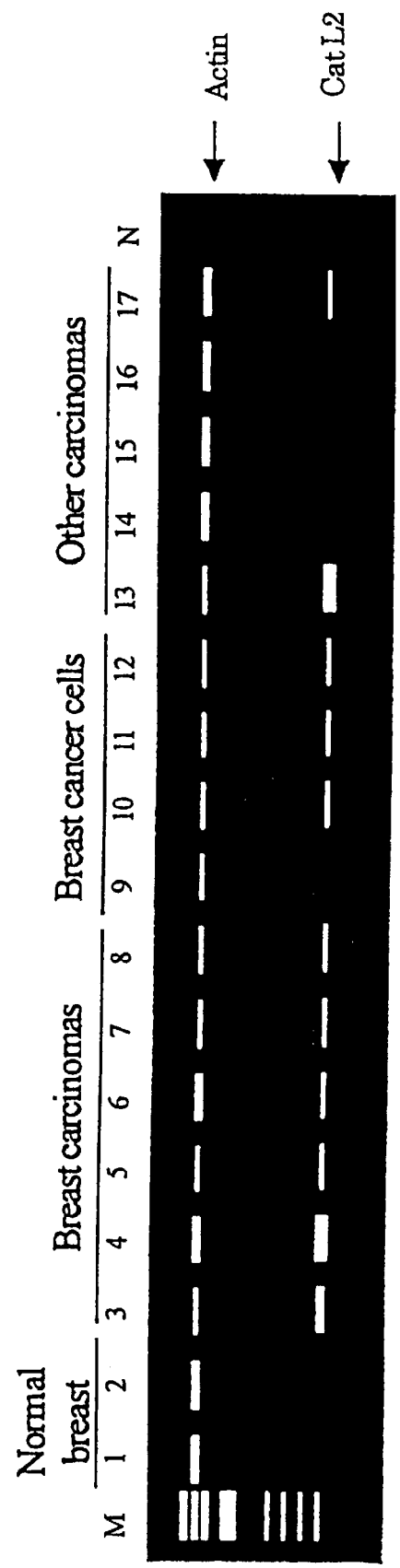
FIG. 5 is RT-PCR analysis of cathepsin L2 in breast carcinomas, breast cancer cell lines, and tumors from other sources. RT-PCR was performed on 4 μg of total RNA from the samples. A 184-bp fragment corresponding to a segment of cathepsin L2 cDNA (Cath L2) was amplified in a volume of 100 μL, and 20 μL of the reaction were separated on a 2.5% agarose gel run in Tris-borate-EDTA. A band of actin was amplified in all cases as a positive control. pBR322 digested with HaeIII was used as a size marker (M). Lanes 1 and 2, normal mammary gland; Lanes 3–8, breast carcinomas; Lanes 9–12, T-47D, ZR-75-1, Hs-578T, and MDA-MB435 breast cancer cells; Lanes 13–17, renal, bladder, prostate, stomach, and ovarian carcinomas, N, negative control.

As seen in FIG. 5, it was verified that a band derived from cathepsin L2 mRNA was amplified from most breast carcinomas and breast cancer cell lines (ZR-75-1, Hs-578T, and MDA-MB435). By contrast, no amplification product was detected in any sample of normal resting mammary gland or in noninvolved breast tissues adjacent to breast carcinomas. Weak cathepsin L2 expression was also observed in some renal and ovarian carcinomas. Taken together, these results strongly suggest that cathepsin L2 can be included in the growing list of proteolytic enzymes potentially in involved in tumor processes.

Example 7

Preparation of Monoclonal Antibodies
(a) Preparation of Antigen Polypeptides

For sequences specific to human cathepsin L2 in which their homology to the other human cathepsin family, especially to human cathepsin L, is low, the following sequences were selected from the amino acid sequence of human cathepsin L2 as described in SEQ ID NO: 1 in the Sequence Listing, and synthesized:

(SEQ ID NO: 9)
Val Pro Lys Phe Asp Gln Asn Leu Asp Thr Lys Trp Tyr Gln (corresponding to Sequence: $Val^{18}$ to $Gln^{31}$ of SEQ ID NO: 1; abbreviated as "CathL2#1")

(SEQ ID NO: 14)
Glu Gly Ala Asn Ser Asn Asn Ser Lys (corresponding to Sequence: $Glu^{287}$ to $Lys^{295}$ of SEQ ID NO: 1; abbreviated as "CathL2#3")

These peptides were synthesized using a peptide synthesizer (peptide synthesizer 9600, MilliGen/Biosearch) with Fmoc-bop methods. Cysteine was introduced at the N-terminus of each polypeptide. The synthetic peptides were purified with high performance liquid chromatography using µBondasphere, C18 column (Waters).

(b) Preparation of Polypeptide-BSA Conjugates

Each peptide was coupled with bovine serum albumin (BSA) via a cysteine residue to form an antigen-conjugate. BSA (25.2 mg) was dissolved in 1 mL of 0.1M phosphate buffer, pH 7.0. Also, 2.86 mg of EMCS (N-(ε-maleimidecaproyloxy)succinmide was dissolved in 42.0 µL of dimethylformamide. A mixture of the BSA solution and the EMCS solution was reacted at 30° C. for 30 min., and then subjected to gel filtration through a SEPHADEX™ G-25 (Pharmacia) column (13 mm φ×120 mm long) equilibrated with a 0.1M phosphate buffer, pH 7.0. The concentration of the resultant maleimido-coupled BSA was 8.81 mg/mL. Each synthetic polypeptide obtained in the above (a) was dissolved in a 0.1M phosphate buffer, pH 7.0, then mixed with the maleimido-coupled BSA thus prepared (molar ratio of polypeptide:maleimido-coupled BSA=50:1). For example, the polypeptide, CathL2#1 (1806 nmol) was mixed with the maleimido-coupled BSA (36.1 nmol); and the polypeptide, CathL2#3 (2353 nmol) was mixed with the maleimido-coupled BSA (47.1 nmol). A total volume of the mixture was adjusted to 1 mL and incubated at 4° C. for 20 hours to form a BSA-polypeptide conjugate. The protein concentration of the resultant BSA-polypeptide conjugate is 5.9 mg/mL and 5.6 mg/mL, respectively. Each BSA-polypeptide conjugate was diluted with a 0.1 M phosphate buffer, pH 7.0, to 200 µg/150 µL, poured to each tube (150 µL per tube) and cryopreserved at −30° C.

(c) Preparation of Antibody-producing Cells (1) A six-week old female Balb/c mouse was primarily immunized by administering intraperitoneally 200 µg of BSA-polypeptide (CathL2#1) conjugate (prepared in the above (b) step) together with complete Freund's adjuvants. 19 days later, 200 µg of the BSA-polypeptide conjugate dissolved in a 0.1M phosphate buffer, pH7.5, was administered intraperitoneally to the primarily immunized mouse for booster. Further 52 days later, 200 µg of the BSA-polypeptide conjugate dissolved in a 0.1 M phosphate buffer, pH7.5, was administered intravenously to the mouse for final immunization. Next four days later, the spleen was taken out, and the spleen cell suspension was prepared. One of two mice immunized with the BSA-polypeptide (CathL2#1) conjugate died after the final immunization.

(2) A six-week old female Balb/c mouse was primarily immunized by administering intraperitoneally 200 µg of BSA-polypeptide (CathL2#3) conjugate (prepared in the above (b) step) together with complete Freund's adjuvants. 29 days later, 200 µg of the BSA-polypeptide conjugate dissolved in a 0.1M phosphate buffer, pH7.5, was administered intraperitoneally to the primarily immunized mouse for booster. Further 51 days later, 200 µg of the BSA-polypeptide conjugate dissolved in a 0.1M phosphate buffer, pH7.5, was administered intravenously to the mouse for final immunization. Next three days later, the spleen was taken out, and the spleen cell suspension was prepared. Two mice were immunized in this experiment.

(d) Cell Fusion (1) The following materials and methods were used:

RPMI-1640 medium:
To RPMI-1640 (Flow Lab.) were added sodium bicarbonate (24 mM), sodium pyruvate (1 mM), penicillin G potassium (50 U/ml), and amikacin sulfate (100 µg/ml), and the mixture was adjusted pH to 7.2 with dry ice, sterilized and filtered through a 0.2 µm Toyo Membrane Filter.

NS-1 medium:
To the above RPMI-1640 medium was added filter sterilized fetal calf serum (FCS, M. A. Bioproducts) until a concentration of FCS reached 15% (v/v).

PEG 4000 solution:
To RPMI-1640 medium was added polyethylene glycol 4000 (PEG-4000, Merck & Co.) until a concentration of PEG 4000 reached 50% (w/w). Thus, the serum-free solution was prepared.

Cell fusion using 8-azaguanine-resistant myeloma SP-2 cells (SP-2/0-Ag14) was carried out by slightly modified methods according to Oi & Herzenberg techniques disclosed in "Selected Method in cellular immunology, p351 to 372 (ed. B. B. Mishell and S. N. Shiigi), W. H. Freeman and Company (1980)".

The respective nucleated spleen cells (viable cell ratio: 100%) prepared in the foregoing (c)-(1) were fused with myeloma cells (viable cell ratio: 100%) in a ratio of 10:1 according to the following procedure:

Each polypeptide-immunized spleen cell suspension and the myeloma cells were washed respectively with a RPMI 1640 medium followed by resuspending in the same medium. For fusion, $4.6 \times 10^8$ nucleated spleen cells and $4.5 \times 10^7$ myeloma cells were mixed together.

Also, the respective nucleated spleen cells (viable cell ratio: 100%) prepared in the foregoing (c)-(2) were fused with myeloma cells (viable cell ratio: 100%) in a ratio of 5:1 according to the following procedure:

Each polypeptide-immunized spleen cell suspension and the myeloma cells were washed respectively with a RPMI 1640 medium followed by resuspending in the same medium. For fusion, $4.6 \times 10^8$ nucleated spleen cells and $9.2 \times 10^7$ myeloma cells were mixed together.

The cell suspension was then precipitated by centrifugation and the supernatant was completely aspirated off. To the cell pellet was added a PEG 4000 solution (RPMI 1640 medium containing 50% (w/v) polyethylene glycol 4000) pre-warmed to 37° C. dropwise for 1 min. (the volume of the PEG 4000 solution to be added was determined to give $3 \times 10^7$ myeloma cells/mL), and stirred for 1 min. to allow the cells to be resuspended and dispersed. Next, after 37° C. pre-warmed RPMI 1640 medium was added dropwise for 2 minutes (RPMI 1640 medium:50% PEG 4000-containing RPMI 1640 medium already added=2:1 in volume), the same medium was added dropwise within 2 to 3 minutes with stirring (RPMI 1640 medium:50% PEG 4000-containing RPMI 1640 medium=7:1 in volume) to allow the cells to be dispersed. This cell dispersion was centrifuged, and the supernatant fluid was completely aspirated off. To the cell pellet was added 37° C. pre-warmed NS-1 medium quickly until a concentration of myeloma cells reached $3 \times 10^6$ cells/mL, and a large cell mass was carefully dispersed by pipetting. Next, the cell suspension was diluted with the same medium, and $6.0 \times 10^5$ cells/well was plated on each well of a polystyrene 96-well microtiter tray. The cell-containing microwell was incubated at 37° C. under a 100% humidified atmosphere containing 7% $CO_2$/93% air.

(e) Selective Growth of Hybridomas in Selection Medium (1) Media to be used were as follows:

HAT medium: To NS-1 medium as described in foregoing (d)-(1) was added further hypoxanthine (100 µM), aminopterin (0.4 µM), and thymidine (16 µM).

HT medium: The medium has the same composition as the foregoing HAT medium except that aminopterin was excluded.

(2) Next day (first day) from culture initiation of the foregoing (d), two drops of HAT medium (approximately 0.1 mL) was added to the cells with a Pasteur pipette. On the 2nd, 3rd, 5th, and 8th days, a half of the medium (approximately 0.1 ml) was replaced with fresh HAT medium, respectively. On the 10th day, a half of the medium was replaced with fresh HT medium. On the 14th day, positive wells were examined by solid phase-antibody binding test (enzyme-linked immunosorbent assay; ELISA) for all wells wherein the growth of hybridomas was visually recognized.

Polystyrene 96-well plates were coated with each polypeptide (100 ng/well) used as an antigen wherein the polypeptide was diluted with a 20 mM carbonate buffer, pH 9.6, and washed with PBS containing 0.05% Tween 20 for washing to remove unadsorbed peptides. To each polypeptide-coated well was added 0.1 ml of supernatant fluid from the hybridoma well in which hybridomas were grown and the polypeptide-coated well was allowed to stand at room temperature for approximately one hour. After washing, horseradish peroxidase (HRP)-labeled goat anti-mouse immunoglobulin (Cappel Lab.) was added as a second antibody to the polypeptide-coated well, and the well was further allowed to stand at room temperature for approximately 1 hour. Next, after washing, to the well was added substrates, hydrogen peroxide and o-phenylenediamine, and OD readings at 492 nm were obtained by a microplate OD reader (MRP-A4, Toso).

(f) Cloning of Hybridomas

Hybridomas in the well positive against each antigen peptide obtained in the foregoing (e) were cloned by limiting dilution to establish monoclones.

That is, a cloning medium containing, as feeder cells, $10^7$ mouse thymocytes per 1 ml of NS-1 medium was prepared. Into a 96-well microtiter tray was plated hybridomas at a cell density of 5, 1, or 0.5 cells per well, respectively, with dilutions wherein the 5, 1, or 0.5 hybridoma cells per well was plated to 36, 36, and 24 wells, respectively. On the 5th and 12th days, about 0.1 ml of NS-1 medium was added to all the wells. Approximately two weeks later from the initiation of cloning, ELISA as described in the above (e) was conducted for groups wherein the sufficient growth of hybridomas was visually recognized and the rate of colony formation-negative wells is 50% or more. In cases where all the examined wells were negative, 4 to 6 wells each containing 1 colony were selected from antibody-positive wells, and recloned. Finally, anti-target polypeptide antibody-producing hybridoma cells were obtained, respectively.

(g) Determination of Class and Sub-class for Monoclonal Antibody

To microtiter plates on which each polypeptide was coated according to ELISA as described herein above, was added each supernatant obtained in the above (f). Next, after PBS washing, iso-type specific rabbit anti-mouse IgG antibodies (Zymed Lab.) were added. After PBS washing, horseradish peroxidase-labeled goat anti-rabbit IgG (H+L) was added, and visualization was carried out with hydrogen peroxide and 2,2'-azino-di(3-ethylbenzothiazolinic acid). As a result, the class and sub-class were determined. Finally, as shown in Table 1, plural monoclonal anti-human cathepsin L2 antibody-producing hybridomas were obtained.

Each clone No. assigned to each hybridoma clone which produces monoclonal antibodies against human cathepsin L2 polypeptides, obtained in above (f), together with its subclass type, is shown in Table 1. Identifier Nos., 212 series, are assigned to members of hybridoma clones generated by immunization with BSA-polypeptide (CathL2#1) conjugates wherein the 212 was tagged on the head of each clone name. Identifier Nos., 219 series, are to members of hybridoma clones generated by immunization with BSA-polypeptide (CathL2#3) conjugates, similarly.

TABLE 1

Anti-Polypeptide CathL2#1

| Clone No. | Subclass/Chain |
| --- | --- |
| 212-1E1 | γ1/κ |
| -2G4 | γ1/κ |
| -3D9 | γ2a/κ |
| -4E4 | γ3/κ |
| -5A3 | μ/κ |
| -6H2 | μ/κ |
| -10F7 | μ/κ |
| -12A1 | γ3/κ |
| -19D11 | μ/κ |
| -22B11 | γ1/κ |
| -24E2 | γ3/κ |

TABLE 2

Anti-Polypeptide CathL2#3

| Clone No. | Subclass/Chain |
| --- | --- |
| 219-11H4 | γ1/κ |
| -13H4 | γ1/κ |

(h) Screening Using Western Blots for Monoclonal Antibodies (1) Preparation of GST-fusion human cathepsin L2

*Escherichia coli* DH5α was transformed with the recombinant plasmid, pGEX-3X CathL2, as disclosed in Example 3. The resultant transformed bacterial cells were cultured on an LB agar medium containing 100 μg/mL ampicillin. A single colony was selected from the cultured plate, inoculated and cultured in 1 mL of LB medium containing 100 μg/mL ampicillin at 37° C. for about 16 hrs. The resulting primary culture was inoculated in 10 mL of LB medium containing 100 μg/mL ampicillin and grown to an $A_{600}$ of 0.6 at 37° C. Then, IPTG was added to a final concentration of 0.5 mM, and the incubation was continued at 37° C. for 4 hrs to induce the expression of recombinant GST-fusion human cathepsin L2 proteins. After the expression induction, transformants were collected by centrifugation, resuspended in 1 mL of buffers for SDS-PAGE samples, sonicated, and boiled (at 95° C. for 5 min) to afford antigens for monoclonal antibody screening by Western blotting.

(2) Preparation of His-Tagged Fusion Human Cathepsin L2 (Proenzyme)

The plasmid contained in clone 5.1.1, as described in Example 2, was cut with BamHI to produce a fragment containing a human cathepsin L2 gene. The resulting fragments were further partially digested with MspA1I (New England BioLabs) and a human cathepsin L2 (proenzyme) gene fragment corresponding to the region from the MspA1I cleavage site at positions 116–121 to the BamHI cleavage site at positions 1183–1189 of SEQ ID NO: 2 was isolated and purified. This human cathepsin L2 (proenzyme) gene fragment was cloned into SmaI and BamHI-cut pUC18. Next, the resultant cloned products were cut with SacI and HindIII to afford human cathepsin L2 (proenzyme) gene fragments. After purification, the fragment was integrated into an SacI and HindIII-cut pTrcHisA vector (Invitrogen) for expression in *E. coli* to form a plasmid, pTrcHisCathL2 (pro).

*Escherichia coli* JM109 was transformed with the recombinant plasmid, pTrcHisCathL2(pro). The resultant transformed bacterial cells were cultured on an LB agar medium containing 100 µg/mL ampicillin. A single colony was selected from the cultured plate, inoculated and cultured in 1 mL of LB medium containing 100 µg/mL ampicillin at 37° C. for 16 hrs. The resulting primary culture was inoculated in 10 mL of LB medium containing 100 µg/mL ampicillin and grown to an $A_{600}$ of 0.6 at 37° C. Then, IPTG was added to a final concentration of 0.5 mM, and the incubation was continued at 37° C. for 4 hrs to induce the expression of recombinant His-tagged fusion human cathepsin L2 (proenzyme) proteins. After the expression induction, transformant cells were collected by centrifugation, resuspended in 1 mL of buffers for SDS-PAGE samples, sonicated, and boiled (at 95° C. for 5 min) to afford antigens for monoclonal antibody screening by Western blotting.

(3) Western Blotting

The recombinant human cathepsin L2 prepared in above (h)-(1) & (2) was subjected to SDS-PAGE and transferred to nitrocellulose membranes. The membranes were blocked in 50 mM phosphate buffer, pH7.5 containing 3% skim milk and 0.1M NaCl at room temperature for 1 hr and cut into strips with 2.8 mm in width.

Each hybridoma cell culture supernatant, prepared in above (f), was added to each strip and reacted at room temperature for 16 hrs. Then, the strips were washed with 50 mM phosphate buffer, pH7.5 containing 0.1M NaCl and reacted at room temperature for 1 hr with HRP-labeled goat anti-mouse immunoglobulins (Cappel) which were diluted 3000-fold with 50 mM phosphate buffer, pH7.5 containing 3% skim milk and 0.1M NaCl. After washing, use of hydrogen peroxide and 3,3'-diaminobenzidine as substrates led to colored products.

The hybridoma clones obtained by immunization with BSA-conjugated polypeptide CathL2#1 (212 series) were assayed using His-tagged fusion human cathepsin L2 (proenzyme) prepared in above (h)(2) as an antigen to check their reactivity therewith. The hybridoma clones obtained by immunization with BSA-conjugated polypeptide CathL2#3 (219 series) were using GST-fusion human cathepsin L2 prepared in above (h)(1) similarly.

(i) Hybridoma Cultivation and Purification of Monoclonal Antibodies

Each hybridoma cell thus obtained was grown in NS-1 medium to afford monoclonal antibodies with a concentration of 10 to 100 µg/ml in the culture supernatant. Alternatively, $10^7$ hybridoma cells thus obtained were administered intraperitoneally to a mouse (inbred Balb/c mouse, ♀, six-week old) primed intraperitoneally with Pristane (2,6,10,14-tetramethyl pentadecane) 1 week prior to hybridoma injection, and 1 to 2 weeks later an ascites containing 4 to 7 mg/ml monoclonal antibody was recollected. The obtained ascites were salted out with 40% ammonium sulfate saturation, IgG class antibodies were adsorbed on protein A affigel (Bio-Rad), followed by elution with 0.1M citrate buffer, pH 5.0 to afford purified forms.

Example 8

Sandwich EIA

Sandwich EIA systems capable of specifically detecting and/or measuring human cathepsin L2 can be composed by a combination of suitable two antibodies selected from monoclonal anti-human cathepsin L2 antibodies as prepared in Example 7, according to techniques as disclosed herein below. The EIA systems may include either of one-step and two-step techniques but labeled antibodies are not limited to Fab'-HRP. Compositions for each reaction buffer, reaction conditions can be adjusted depending on various purposes of assaying. For example, the reaction time can be shortened or extended. Standard human cathepsin L2 samples can be obtained by isolation and purification from tissue culture supernatants, cell culture supernatants, and transformants or transfectants wherein the human cathepsin L2 is expressed by techniques as described in Examples 3 and 5 or other methods. The purification can be conducted by a combination of ion-exchange chromatography, gel filtration, affinity chromatography using monoclonal anti-human cathepsin L2 antibodies, and/or other various affinity chromatography.

(a) Preparation of Labeled Antibodies

Monoclonal anti-human cathepsin L2 antibodies were digested with pepsin (enzyme: antibody ratio, 2% w/w) in 0.1M acetate buffer, pH4.2 containing 0.1M NaCl at 37° C. for 24 hrs. The digestion was stopped with the addition of 3M Tris-HCl buffer, pH7.5. $F(ab')_2$ fractions were collected by gel filtration on an Ultrogel AcA54 column equilibrated with 0.1M phosphate buffer, pH7.0. Cysteamine hydrochloride was added to the $F(ab')_2$ fractions until the final concentration reached to 0.01M. The fragments were reduced at 37° C. for 1.5 hr. Fab' fractions were collected by gel filtration on an Ultrogel AcA54 column equilibrated with 0.1M phosphate buffer, pH6.0 containing 5 mM EDTA.

In another procedure, HRP was dissolved in 0.1M phosphate buffer, pH7.0, followed by addition of EMCS in DMF (EMCS:HRP molar ratio, 25:1). The mixture was incubated at 30° C. for 30 min. and subjected to gel filtration on a NICK-5 column (Pharmacia) equilibrated with 0.1M phosphate buffer, pH6.0 to collect maleimide-conjugated HRP fractions.

The Fab' fraction was mixed with the maleimide-conjugated HRP fraction to form an equimolar mixture. The resultant mixture was incubated at 4° C. for 20 hrs, followed by blocking of unreacted thiol groups with N-ethyl maleimide (N-ethyl maleimide:Fab' molar ratio, 10:1). The mixture was subjected to gel filtration on an Ultrogel AcA54 column equilibrated with 0.1M phosphate buffer, pH6.5 to collect labeled antibodies, Fab'-HRP conjugates. The labeled antibody fraction supplemented with 0.1% BSA and 0.001% chlorhexidine was stored at 4° C.

(b) Preparation of Monoclonal Antibody-coated Carriers

Monoclonal anti-human cathepsin L2 antibodies were dissolved in 0.1M phosphate buffer, pH7.5 to a concentration of 50 µg/mL. The monoclonal antibody solution was added to each well of a 96-well microtiter plate at 100 µL per well and allowed to stand at 4° C. for 18 hrs. After removal of the monoclonal antibody solution, each well was rinsed once with a physiological saline and three times with Tris-HCl buffer, pH8.0 containing 0.05% Tween 20, 0.1M NaCl and 5 mM $CaCl_2$ and blocked by the addition of Tris-HCl buffer, pH8.0 containing 1% BSA, 0.1M NaCl and 5 mM $CaCl_2$.

(c) A One-step Sandwich EIA

A standard curve was prepared using purified human cathepsin L2 fractions as standard antigens for quantitative assay of human cathepsin L2.

The standard human cathepsin L2 samples diluted serially with Tris-HCl buffer, pH8.0 containing 1% BSA, 0.05% Brij35, 0.05% Tween 20, 0.1M NaCl and 5 mM $CaCl_2$ were poured into each well at 60 µL per well, followed by addition of the labeled antibody, Fab'-HRP (60 µL per well), which was resuspended in Tris-HCl buffer, pH8.0 containing 1% BSA, 0.05% Brij35, 0.05% Tween 20, 0.1M NaCl and 5 mM $CaCl_2$ to a concentration of 100 ng/50 µL. The samples were well mixed. The antibody-bound microtiter plates prepared herein above were rinsed three times with Tris-HCl buffer, pH8.0 containing 0.05% Tween 20, 0.1M NaCl and 5 mM CaCl$_2$. To each well was added the standard antigen-labeled antibody mixture at 100 μL/well. After incubation at room temperature for 1 hr, each well was rinsed three times with Tris-HCl buffer, pH8.0 containing 0.05% Tween 20, 0.1M NaCl and 5 mM CaCl$_2$. Next, to each well was added 1.2 mg/mL o-phenylenediamine (100 μL per well) dissolved in 0.1M citrate-phosphate buffer, pH4.9 containing 0.02% hydrogen peroxide and incubated at room temperature for 20 min. The reaction was stopped with the addition of 100 μL of 2N sulfuric acid. The reaction mixtures were read at 492 nm in a microtiter plate reader to prepare a standard curve.

The samples to be assayed may be prepared from human body fluids including human blood, serum, plasma, articular fluid, urine, saliva, cerebrospinal fluid, amniotic fluid, etc., various human tissue extracts, various cultured cell extracts and culture supernatants derived from human origins or recombinants, etc. Each sample to be assayed may be subjected to one-step sandwich EIA as disclosed herein above in place of the standard human cathepsin L2 sample. The reaction for the sample to be assayed is conducted simultaneously with that for the standard human cathepsin L2 sample. The results are analyzed by reference to standard binding curve to estimate an amount of human cathepsin L2 contained in tested samples.

The success in (i) cloning, from human brain cDNA libraries, a full-length gene encoding human cathepsin L2, which is novel and a member of the papain family composed of cysteine proteinases though it has a homology to human cathepsin L gene sequence, and (ii) analyzing its nucleotide sequence leads those skilled in the art to the application of human cathepsin L2 gene to researches on not only various normal cellular processes, including the turnover of intracellular proteins, prohormone activation, and bone remodeling, but also a variety of pathological conditions, diseases, and disorders, such as Alzheimer's disease, pulmonary emphysema, rheumatoid arthritis, muscular dystrophy, osteoporosis, neurodegenerative disease, and cancer invasion and metastasis. Further, it enables us to disclose enzymatic characteristics thereof via using recombinant proteins obtainable by the expression of the gene in E. coli or other hosts, and to study substances inhibiting its activity. It also enables us to determine the chromosomal locus of human cathepsin L2 gene and to examine the gene expression in human tissues. The probes for genes are useful as techniques for detecting human cathepsin L2 gene, cells expressed the gene, etc, and reagents or tools therefor. The production of antibodies, particularly monoclonal antibodies, specifically reactive to human cathepsin L2 leads to techniques for detecting human cathepsin L2, including immunostaining for tissues and reagents or tools therefor. The present invention provides techniques for detecting or assaying human cathepsin L2, such as EIA systems. The agents are useful in or applicable to not only detection and diagnosis of cancers but also elucidation and disclosure of the mechanism leading to onset related to said pathological conditions, diseases, and disorders, and development in therapeutic techniques or agents therefor.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

What is claimed is:

1. An isolated protein or a salt thereof, said isolated protein comprising the amino acid sequence selected from the group consisting of (a) SEQ ID No: 1, (b) amino acid residues 114 to 334 of SEQ ID NO: 1, and (c) amino acid residues 18 to 334 of SEQ ID NO: 1, said protein possessing a cysteine proteinase activity.

2. An isolated protein having cysteine proteinase activity, which is obtained from a culture comprising a host cell transformed or transfected with a vector, said vector comprising a polynucleotide encoding the isolated protein of claim 1.

3. A composition comprising the protein or the salt thereof according to claim 1.

4. A method for screening a compound which enhances or inhibits the enzymatic activity of the protein or salt thereof of claim 1, comprising contacting the protein or salt thereof with a substrate to determine the enzymatic activity of the protein or salt thereof, contacting the protein or salt thereof with a substrate in the presence of the compound to determine the enzymatic activity of the protein or salt thereof with the compound, and comparing the two enzymatic activities to determine whether the compound enhances or inhibits the enzymatic activity of the protein or salt thereof.

5. A screening kit for a compound which enhances or inhibits the enzymatic activity of the protein or salt thereof of claim 1, comprising the protein or salt thereof and a substrate.

* * * * *

SEQUENCE LISTING

<160> NUMBER OF SEQ ID NOS: 25

<210> SEQ ID NO 1
<211> LENGTH: 334
<212> TYPE: PRT
<213> ORGANISM: Human

<400> SEQUENCE: 1

```
Met Asn Leu Ser Leu Val Leu Ala Ala Phe Cys Leu Gly Ile Ala Ser
 1               5                  10                  15

Ala Val Pro Lys Phe Asp Gln Asn Leu Asp Thr Lys Trp Tyr Gln Trp
            20                  25                  30

Lys Ala Thr His Arg Arg Leu Tyr Gly Ala Asn Glu Glu Gly Trp Arg
        35                  40                  45

Arg Ala Val Trp Glu Lys Asn Met Lys Met Ile Glu Leu His Asn Gly
    50                  55                  60

Glu Tyr Ser Gln Gly Lys His Gly Phe Thr Met Ala Met Asn Ala Phe
65                  70                  75                  80

Gly Asp Met Thr Asn Glu Glu Phe Arg Gln Met Met Gly Cys Phe Arg
                85                  90                  95

Asn Gln Lys Phe Arg Lys Gly Lys Val Phe Arg Glu Pro Leu Phe Leu
            100                 105                 110

Asp Leu Pro Lys Ser Val Asp Trp Arg Lys Lys Gly Tyr Val Thr Pro
        115                 120                 125

Val Lys Asn Gln Lys Gln Cys Gly Ser Cys Trp Ala Phe Ser Ala Thr
```

-continued

```
                130               135               140
Gly Ala Leu Glu Gly Gln Met Phe Arg Lys Thr Gly Lys Leu Val Ser
145                 150                 155                 160

Leu Ser Glu Gln Asn Leu Val Asp Cys Ser Arg Pro Gln Gly Asn Gln
                165                 170                 175

Gly Cys Asn Gly Gly Phe Met Ala Arg Ala Phe Gln Tyr Val Lys Glu
                180                 185                 190

Asn Gly Gly Leu Asp Ser Glu Glu Ser Tyr Pro Tyr Val Ala Val Asp
                195                 200                 205

Glu Ile Cys Lys Tyr Arg Pro Glu Asn Ser Val Ala Asn Asp Thr Gly
210                 215                 220

Phe Thr Val Val Ala Pro Gly Lys Glu Lys Ala Leu Met Lys Ala Val
225                 230                 235                 240

Ala Thr Val Gly Pro Ile Ser Val Ala Met Asp Ala Gly His Ser Ser
                245                 250                 255

Phe Gln Phe Tyr Lys Ser Gly Ile Tyr Phe Glu Pro Asp Cys Ser Ser
                260                 265                 270

Lys Asn Leu Asp His Gly Val Leu Val Val Gly Tyr Gly Phe Glu Gly
                275                 280                 285

Ala Asn Ser Asn Asn Ser Lys Tyr Trp Leu Val Lys Asn Ser Trp Gly
290                 295                 300

Pro Glu Trp Gly Ser Asn Gly Tyr Val Lys Ile Ala Lys Asp Lys Asn
305                 310                 315                 320

Asn His Cys Gly Ile Ala Thr Ala Ala Ser Tyr Pro Asn Val
                325                 330

<210> SEQ ID NO 2
<211> LENGTH: 1342
<212> TYPE: DNA
<213> ORGANISM: Human

<400> SEQUENCE: 2
cggctgtaat ctcagaggct tgtttgctga gggtgcctgc gcacgtgcga cggctgctgg       60
ttttgaaaca tgaatctttc gctcgtcctg gctgcctttt gcttgggaat agcctccgct      120
gttccaaaat ttgaccaaaa tttggataca agtggtacca gtggaaggca acacacaga      180 agattatatg gcgcgaatga agaaggatgg aggagagcag tgtgggaaaa gaatatgaaa      240
atgattgaac tgcacaatgg ggaatacagc caagggaaac atggcttcac aatggccatg      300
aatgcttttg gtgacatgac caatgaagaa ttcaggcaga tgatgggttg ctttcgaaac      360
cagaaattca ggaagggaaa agtgttccgt gagcctctgt tcttgatctt cccaaatct      420 gtggattgga gaaagaaagg ctacgtgacg ccagtgaaga tcagaaaca gtgtggttct      480 tgttgggctt ttagtgcgac tggtgctctt gaaggacaga tgttccggaa actgggaaa      540 cttgtctcac tgagcgagca gaatctggtg gactgttcgc gtcctcaagg caatcagggc      600
tgcaatggtg gcttcatggc tagggccttc agtatgtca aggagaacgg aggcctggac      660
tctgaggaat cctatccata tgtagcagtg gatgaaatct gtaagtacag acctgagaat      720
tctgttgcta atgacactgg cttcacagtg gtcgcacctg gaaaggagaa ggccctgatg      780 aaaagcagtcg caactgtggg gcccatctcc gttgctatgg atgcaggcca ttcgtccttc      840
cagttctaca aatcaggcat ttattttgaa ccagactgca gcagcaaaaa cctggatcat      900
ggtgttctgg tggttggcta cggctttgaa ggagcaaatt cgaataacag caagtattgg      960
ctcgtcaaaa acagctgggg tccagaatgg ggctcgaatg gctatgtaaa aatagccaaa     1020
```

```
gacaagaaca accactgtgg aatcgccaca gcagccagct accccaatgt gtgagctgat    1080
ggatggtgag gaggaaggac ttaaggacag catgtctggg gaaattttat cttgaaactg    1140
accaaacgct tattgtgtaa gataaaccag ttgaatcatt gaggatccaa gttgagattt    1200
taattctgtg acatttttac aagggtaaaa tgttaccact actttaatta ttgttataca    1260
cagctttatg atatcaaaga ctcattgctt aattctaaga cttttgaatt ttcattttt     1320 aaaaagatgt acaaaacagt tt                                             1342

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 3
atgtggctct tgttgggctt                                                  20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 4
gcctcagctt caagacctt                                                   19

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 5
atgcttccca aatctgtgga ttgg                                             24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 6
tcacacattg gggtagctgg                                                  20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 7
cttaaggaca gcatgtctgg ggaa                                             24
```

```
<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide to act as a primer for PCR

<400> SEQUENCE: 8
agtctttgat atcataaagc tgtg                                    24

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 9

Val Pro Lys Phe Asp Gln Asn Leu Asp Thr Lys Trp Tyr Gln
  1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 10

Met Met Gly Cys Phe Arg Asn Gln Lys Phe
  1               5                  10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 11

Leu Asp Leu Pro Lys
  1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 12

Val Ala Val Asp Glu Ile Cys Lys Tyr Arg Pro Glu Asn
  1               5                  10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 13
```

```
Thr Val Val Ala Pro Gly Lys
  1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Designed
      peptide to act as an immunogen

<400> SEQUENCE: 14

Glu Gly Ala Asn Ser Asn Asn Ser Lys
  1               5

<210> SEQ ID NO 15
<211> LENGTH: 1342
<212> TYPE: DNA
<213> ORGANISM: Human
<220> FEATURE:
<221> NAME/KEY: CDS
<222> LOCATION: (70)..(1071)
<220> FEATURE:
<221> NAME/KEY: sig_peptide
<222> LOCATION: (70)..(120)
<220> FEATURE:
<221> NAME/KEY: mat_peptide
<222> LOCATION: (121)..(1071)

<400> SEQUENCE: 15
```

```
cggctgtaat ctcagaggct tgtttgctga gggtgcctgc gcacgtgcga cggctgctgg        60 ttttgaaac atg aat ctt tcg ctc gtc ctg gct gcc ttt tgc ttg gga ata       111
         Met Asn Leu Ser Leu Val Leu Ala Ala Phe Cys Leu Gly Ile
             -15                 -10                 -5 gcc tcc gct gtt cca aaa ttt gac caa aat ttg gat aca aag tgg tac         159
Ala Ser Ala Val Pro Lys Phe Asp Gln Asn Leu Asp Thr Lys Trp Tyr
        -1   1               5                  10 cag tgg aag gca aca cac aga aga tta tat ggc gcg aat gaa gaa gga         207
Gln Trp Lys Ala Thr His Arg Arg Leu Tyr Gly Ala Asn Glu Glu Gly
         15                  20                  25 tgg agg aga gca gtg tgg gaa aag aat atg aaa atg att gaa ctg cac         255
Trp Arg Arg Ala Val Trp Glu Lys Asn Met Lys Met Ile Glu Leu His
 30                  35                  40                  45 aat ggg gaa tac agc caa ggg aaa cat ggc ttc aca atg gcc atg aat         303
Asn Gly Glu Tyr Ser Gln Gly Lys His Gly Phe Thr Met Ala Met Asn
                 50                  55                  60 gct ttt ggt gac atg acc aat gaa gaa ttc agg cag atg atg ggt tgc         351
Ala Phe Gly Asp Met Thr Asn Glu Glu Phe Arg Gln Met Met Gly Cys
             65                  70                  75 ttt cga aac cag aaa ttc agg aag ggg aaa gtg ttc cgt gag cct ctg         399
Phe Arg Asn Gln Lys Phe Arg Lys Gly Lys Val Phe Arg Glu Pro Leu
         80                  85                  90 ttt ctt gat ctt ccc aaa tct gtg gat tgg aga aag aaa ggc tac gtg         447
Phe Leu Asp Leu Pro Lys Ser Val Asp Trp Arg Lys Lys Gly Tyr Val
     95                 100                 105 acg cca gtg aag aat cag aaa cag tgt ggt tct tgt tgg gct ttt agt         495
Thr Pro Val Lys Asn Gln Lys Gln Cys Gly Ser Cys Trp Ala Phe Ser
110                 115                 120                 125 gcg act ggt gct ctt gaa gga cag atg ttc cgg aaa act ggg aaa ctt         543
Ala Thr Gly Ala Leu Glu Gly Gln Met Phe Arg Lys Thr Gly Lys Leu
                 130                 135                 140 gtc tca ctg agc gag cag aat ctg gtg gac tgt tcg cgt cct caa ggc         591
Val Ser Leu Ser Glu Gln Asn Leu Val Asp Cys Ser Arg Pro Gln Gly
             145                 150                 155
```

-continued

| | |
|---|---|
| aat cag ggc tgc aat ggt ggc ttc atg gct agg gcc ttc cag tat gtc<br>Asn Gln Gly Cys Asn Gly Gly Phe Met Ala Arg Ala Phe Gln Tyr Val<br>        160                       165                   170 | 639 |
| aag gag aac gga ggc ctg gac tct gag gaa tcc tat cca tat gta gca<br>Lys Glu Asn Gly Gly Leu Asp Ser Glu Glu Ser Tyr Pro Tyr Val Ala<br>175                      180                        185 | 687 |
| gtg gat gaa atc tgt aag tac aga cct gag aat tct gtt gct aat gac<br>Val Asp Glu Ile Cys Lys Tyr Arg Pro Glu Asn Ser Val Ala Asn Asp<br>190                      195                    200                   205 | 735 |
| act ggc ttc aca gtg gtc gca cct gga aag gag aag gcc ctg atg aaa<br>Thr Gly Phe Thr Val Val Ala Pro Gly Lys Glu Lys Ala Leu Met Lys<br>                  210                       215                   220 | 783 |
| gca gtc gca act gtg ggg ccc atc tcc gtt gct atg gat gca ggc cat<br>Ala Val Ala Thr Val Gly Pro Ile Ser Val Ala Met Asp Ala Gly His<br>225                      230                       235 | 831 |
| tcg tcc ttc cag ttc tac aaa tca ggc att tat ttt gaa cca gac tgc<br>Ser Ser Phe Gln Phe Tyr Lys Ser Gly Ile Tyr Phe Glu Pro Asp Cys<br>                  240                       245                   250 | 879 |
| agc agc aaa aac ctg gat cat ggt gtt ctg gtg gtt ggc tac ggc ttt<br>Ser Ser Lys Asn Leu Asp His Gly Val Leu Val Val Gly Tyr Gly Phe<br>255                      260                        265 | 927 |
| gaa gga gca aat tcg aat aac agc aag tat tgg ctc gtc aaa aac agc<br>Glu Gly Ala Asn Ser Asn Asn Ser Lys Tyr Trp Leu Val Lys Asn Ser<br>270                      275                    280                   285 | 975 |
| tgg ggt cca gaa tgg ggc tcg aat ggc tat gta aaa ata gcc aaa gac<br>Trp Gly Pro Glu Trp Gly Ser Asn Gly Tyr Val Lys Ile Ala Lys Asp<br>                  290                       295                   300 | 1023 |
| aag aac aac cac tgt gga atc gcc aca gca gcc agc tac ccc aat gtg<br>Lys Asn Asn His Cys Gly Ile Ala Thr Ala Ala Ser Tyr Pro Asn Val<br>305                      310                       315 | 1071 |
| tgagctgatg gatggtgagg aggaaggact taaggacagc atgtctgggg aaattttatc | 1131 |
| ttgaaactga ccaaacgctt attgtgtaag ataaaccagt tgaatcattg aggatccaag | 1191 |
| ttgagatttt aattctgtga cattttttaca agggtaaaat gttaccacta ctttaattat | 1251 |
| tgttatacac agctttatga tatcaaagac tcattgctta attctaagac ttttgaattt | 1311 |
| tcattttttta aaaagatgta caaaacagtt t | 1342 |

<210> SEQ ID NO 16
<211> LENGTH: 334
<212> TYPE: PRT
<213> ORGANISM: Human

<400> SEQUENCE: 16

Met Asn Leu Ser Leu Val Leu Ala Ala Phe Cys Leu Gly Ile Ala Ser
        -15                  -10                       -5

Ala Val Pro Lys Phe Asp Gln Asn Leu Asp Thr Lys Trp Tyr Gln Trp
 -1  1            5                   10                     15

Lys Ala Thr His Arg Arg Leu Tyr Gly Ala Asn Glu Glu Gly Trp Arg
               20                       25                     30

Arg Ala Val Trp Glu Lys Asn Met Lys Met Ile Glu Leu His Asn Gly
                  35                     40                     45

Glu Tyr Ser Gln Gly Lys His Gly Phe Thr Met Ala Met Asn Ala Phe
         50                       55                     60

Gly Asp Met Thr Asn Glu Glu Phe Arg Gln Met Met Gly Cys Phe Arg
 65                   70                     75                   80

Asn Gln Lys Phe Arg Lys Gly Lys Val Phe Arg Glu Pro Leu Phe Leu
                80                     85                     90                   95

-continued

```
Asp Leu Pro Lys Ser Val Asp Trp Arg Lys Lys Gly Tyr Val Thr Pro
            100                 105                 110

Val Lys Asn Gln Lys Gln Cys Gly Ser Cys Trp Ala Phe Ser Ala Thr
        115                 120                 125

Gly Ala Leu Glu Gly Gln Met Phe Arg Lys Thr Gly Lys Leu Val Ser
    130                 135                 140

Leu Ser Glu Gln Asn Leu Val Asp Cys Ser Arg Pro Gln Gly Asn Gln
145                 150                 155                 160

Gly Cys Asn Gly Gly Phe Met Ala Arg Ala Phe Gln Tyr Val Lys Glu
                165                 170                 175

Asn Gly Gly Leu Asp Ser Glu Glu Ser Tyr Pro Tyr Val Ala Val Asp
            180                 185                 190

Glu Ile Cys Lys Tyr Arg Pro Glu Asn Ser Val Ala Asn Asp Thr Gly
        195                 200                 205

Phe Thr Val Val Ala Pro Gly Lys Glu Lys Ala Leu Met Lys Ala Val
    210                 215                 220

Ala Thr Val Gly Pro Ile Ser Val Ala Met Asp Ala Gly His Ser Ser
225                 230                 235                 240

Phe Gln Phe Tyr Lys Ser Gly Ile Tyr Phe Glu Pro Asp Cys Ser Ser
                245                 250                 255

Lys Asn Leu Asp His Gly Val Leu Val Val Gly Tyr Gly Phe Glu Gly
            260                 265                 270

Ala Asn Ser Asn Asn Ser Lys Tyr Trp Leu Val Lys Asn Ser Trp Gly
        275                 280                 285

Pro Glu Trp Gly Ser Asn Gly Tyr Val Lys Ile Ala Lys Asp Lys Asn
    290                 295                 300

Asn His Cys Gly Ile Ala Thr Ala Ala Ser Tyr Pro Asn Val
305                 310                 315
```

<210> SEQ ID NO 17
<211> LENGTH: 334
<212> TYPE: PRT
<213> ORGANISM: Human

<400> SEQUENCE: 17

```
Met Asn Leu Ser Leu Val Leu Ala Ala Phe Cys Leu Gly Ile Ala Ser
  1               5                  10                  15

Ala Val Pro Lys Phe Asp Gln Asn Leu Asp Thr Lys Trp Tyr Gln Trp
            20                  25                  30

Lys Ala Thr His Arg Arg Leu Tyr Gly Ala Asn Glu Glu Gly Trp Arg
        35                  40                  45

Arg Ala Val Trp Glu Lys Asn Met Lys Met Ile Glu Leu His Asn Gly
    50                  55                  60

Glu Tyr Ser Gln Gly Lys His Gly Phe Thr Met Ala Met Asn Ala Phe
65                  70                  75                  80

Gly Asp Met Thr Asn Glu Glu Phe Arg Gln Met Met Gly Cys Phe Arg
                85                  90                  95

Asn Gln Lys Phe Arg Lys Gly Lys Val Phe Arg Glu Pro Leu Phe Leu
            100                 105                 110

Asp Leu Pro Lys Ser Val Asp Trp Arg Lys Lys Gly Tyr Val Thr Pro
        115                 120                 125

Val Lys Asn Gln Lys Gln Cys Gly Ser Cys Trp Ala Phe Ser Ala Thr
    130                 135                 140

Gly Ala Leu Glu Gly Gln Met Phe Arg Lys Thr Gly Lys Leu Val Ser
```

-continued

```
            145                 150                 155                 160
Leu Ser Glu Gln Asn Leu Val Asp Cys Ser Arg Pro Gln Gly Asn Gln
                165                 170                 175
Gly Cys Asn Gly Gly Phe Met Ala Arg Ala Phe Gln Tyr Val Lys Glu
            180                 185                 190
Asn Gly Gly Leu Asp Ser Glu Glu Ser Tyr Pro Tyr Val Ala Val Asp
        195                 200                 205
Glu Ile Cys Lys Tyr Arg Pro Glu Asn Ser Val Ala Asn Asp Thr Gly
    210                 215                 220
Phe Thr Val Val Ala Pro Gly Lys Glu Lys Ala Leu Met Lys Ala Val
225                 230                 235                 240
Ala Thr Val Gly Pro Ile Ser Val Ala Met Asp Ala Gly His Ser Ser
                245                 250                 255
Phe Gln Phe Tyr Lys Ser Gly Ile Tyr Phe Glu Pro Asp Cys Ser Ser
            260                 265                 270
Lys Asn Leu Asp His Gly Val Leu Val Val Gly Tyr Gly Phe Glu Gly
        275                 280                 285
Ala Asn Ser Asn Asn Ser Lys Tyr Trp Leu Val Lys Asn Ser Trp Gly
    290                 295                 300
Pro Glu Trp Gly Ser Asn Gly Tyr Val Lys Ile Ala Lys Asp Lys Asn
305                 310                 315                 320
Asn His Cys Gly Ile Ala Thr Ala Ala Ser Tyr Pro Asn Val
                325                 330

<210> SEQ ID NO 18
<211> LENGTH: 333
<212> TYPE: PRT
<213> ORGANISM: Human

<400> SEQUENCE: 18

Met Asn Pro Thr Leu Ile Leu Ala Ala Phe Cys Leu Gly Ile Ala Ser
1               5                   10                  15
Ala Thr Leu Thr Phe Asp His Ser Leu Glu Ala Gln Trp Thr Lys Trp
            20                  25                  30
Lys Ala Met His Asn Arg Leu Tyr Gly Met Asn Glu Glu Gly Trp Arg
        35                  40                  45
Arg Ala Val Trp Glu Lys Asn Met Lys Met Ile Glu Leu His Asn Gln
    50                  55                  60
Glu Tyr Arg Glu Gly Lys His Ser Phe Thr Met Ala Met Asn Ala Phe
65                  70                  75                  80
Gly Asp Met Thr Ser Glu Glu Phe Arg Gln Val Met Asn Gly Phe Gln
                85                  90                  95
Asn Arg Lys Pro Arg Lys Gly Lys Val Phe Gln Glu Pro Leu Phe Tyr
            100                 105                 110
Glu Ala Pro Arg Ser Val Asp Trp Arg Glu Lys Gly Tyr Val Thr Pro
        115                 120                 125
Val Lys Asn Gln Gly Gln Cys Gly Ser Cys Trp Ala Phe Ser Ala Thr
    130                 135                 140
Gly Ala Leu Glu Gly Gln Met Phe Arg Lys Thr Gly Arg Leu Ile Ser
145                 150                 155                 160
Leu Ser Glu Gln Asn Leu Val Asp Cys Ser Gly Pro Gln Gly Asn Glu
                165                 170                 175
Gly Cys Asn Gly Gly Leu Met Asp Tyr Ala Phe Gln Tyr Val Gln Asp
            180                 185                 190
```

```
Asn Gly Gly Leu Asp Ser Glu Glu Ser Tyr Pro Tyr Glu Ala Thr Glu
            195                 200                 205

Glu Ser Cys Lys Tyr Asn Pro Lys Tyr Ser Val Ala Asn Asp Thr Gly
    210                 215                 220

Phe Val Asp Ile Pro Lys Gln Glu Lys Ala Leu Met Lys Ala Val Ala
225                 230                 235                 240

Thr Val Gly Pro Ile Ser Val Ala Ile Asp Ala Gly His Glu Ser Phe
                245                 250                 255

Leu Phe Tyr Lys Glu Gly Ile Tyr Phe Glu Pro Asp Cys Ser Ser Glu
            260                 265                 270

Asp Met Asp His Gly Val Leu Val Gly Tyr Gly Phe Glu Ser Thr
    275                 280                 285

Glu Ser Asp Asn Asn Lys Tyr Trp Leu Val Lys Asn Ser Trp Gly Glu
    290                 295                 300

Glu Trp Gly Met Gly Gly Tyr Val Lys Met Ala Lys Asp Arg Arg Asn
305                 310                 315                 320

His Cys Gly Ile Ala Ser Ala Ala Ser Tyr Pro Thr Val
                325                 330

<210> SEQ ID NO 19
<211> LENGTH: 329
<212> TYPE: PRT
<213> ORGANISM: Human

<400> SEQUENCE: 19

Met Trp Gly Leu Lys Val Leu Leu Leu Pro Val Val Ser Phe Ala Leu
 1               5                  10                  15

Tyr Pro Glu Glu Ile Leu Asp Thr His Trp Glu Leu Trp Lys Lys Thr
                20                  25                  30

His Arg Lys Gln Tyr Asn Asn Lys Val Asp Glu Ile Ser Arg Arg Leu
            35                  40                  45

Ile Trp Glu Lys Asn Leu Lys Tyr Ile Ser Ile His Asn Leu Glu Ala
    50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
            100                 105                 110

Gly Arg Ala Pro Asp Ser Val Asp Tyr Arg Lys Lys Gly Tyr Val Thr
        115                 120                 125

Pro Val Lys Asn Gln Gly Gln Cys Gly Ser Cys Trp Ala Phe Ser Ser
    130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
            180                 185                 190

Arg Gly Ile Asp Ser Glu Asp Ala Tyr Pro Tyr Val Gly Gln Glu Glu
        195                 200                 205

Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240
```

-continued

Arg Val Gly Pro Val Ser Val Ala Ile Asp Ala Ser Leu Thr Ser Phe
            245                 250                 255

Gln Phe Tyr Ser Lys Gly Val Tyr Tyr Asp Glu Ser Cys Asn Ser Asp
        260                 265                 270

Asn Leu Asn His Ala Val Leu Ala Val Gly Tyr Gly Ile Gln Lys Gly
    275                 280                 285

Asn Lys His Trp Ile Ile Lys Asn Ser Trp Gly Glu Asn Trp Gly Asn
290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

<210> SEQ ID NO 20
<211> LENGTH: 331
<212> TYPE: PRT
<213> ORGANISM: Human

<400> SEQUENCE: 20

Met Lys Arg Leu Val Cys Val Leu Leu Val Cys Ser Ser Ala Val Ala
1               5                   10                  15

Gln Leu His Lys Asp Pro Thr Leu Asp His Trp His Leu Trp Lys
            20                  25                  30      Lys

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Leu Lys Cys Gln Tyr Asp Ser Lys Tyr Arg Ala Ala Thr Cys
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu

```
            275                 280                 285
Asn Gly Lys Glu Tyr Trp Leu Val Lys Asn Ser Trp Gly His Asn Phe
    290                 295                 300
Gly Glu Glu Gly Tyr Ile Arg Met Ala Arg Asn Lys Gly Asn His Cys
305                 310                 315                 320
Gly Ile Ala Ser Phe Pro Ser Tyr Pro Glu Ile
                325                 330

<210> SEQ ID NO 21
<211> LENGTH: 335
<212> TYPE: PRT
<213> ORGANISM: Human

<400> SEQUENCE: 21

Met Trp Ala Thr Leu Pro Leu Leu Cys Ala Gly Ala Trp Leu Leu Gly
  1               5                  10                  15
Val Pro Val Cys Gly Ala Ala Glu Leu Ser Val Asn Ser Leu Glu Lys
                 20                  25                  30
Phe His Phe Lys Ser Trp Met Ser Lys His Arg Lys Thr Tyr Ser Thr
             35                  40                  45
Glu Glu Tyr His His Arg Leu Gln Thr Phe Ala Ser Asn Trp Arg Lys
     50                  55                  60
Ile Asn Ala His Asn Asn Gly Asn His Thr Phe Lys Met Ala Leu Asn
 65                  70                  75                  80
Gln Phe Ser Asp Met Ser Phe Ala Glu Ile Lys His Lys Tyr Leu Trp
                 85                  90                  95
Ser Glu Pro Gln Asn Cys Ser Ala Thr Lys Ser Asn Tyr Leu Arg Gly
                100                 105                 110
Thr Gly Pro Tyr Pro Pro Ser Val Asp Trp Arg Lys Lys Gly Asn Phe
            115                 120                 125
Val Ser Pro Val Lys Asn Gln Gly Ala Cys Gly Ser Cys Trp Thr Phe
        130                 135                 140
Ser Thr Thr Gly Ala Leu Glu Ser Ala Ile Ala Ile Ala Thr Gly Lys
145                 150                 155                 160
Met Leu Ser Leu Ala Glu Gln Gln Leu Val Asp Cys Ala Gln Asp Phe
                165                 170                 175
Asn Asn Tyr Gly Cys Gln Gly Gly Leu Pro Ser Gln Ala Phe Glu Tyr
            180                 185                 190
Ile Leu Tyr Asn Lys Gly Ile Met Gly Glu Asp Thr Tyr Pro Tyr Gln
        195                 200                 205
Gly Lys Asp Gly Tyr Cys Lys Phe Gln Pro Gly Lys Ala Ile Gly Phe
    210                 215                 220
Val Lys Asp Val Ala Asn Ile Thr Ile Tyr Asp Glu Glu Ala Met Val
225                 230                 235                 240
Glu Ala Val Ala Leu Tyr Asn Pro Val Ser Phe Ala Phe Glu Val Thr
                245                 250                 255
Gln Asp Phe Met Met Tyr Arg Thr Gly Ile Tyr Ser Ser Thr Ser Cys
            260                 265                 270
His Lys Thr Pro Asp Lys Val Asn His Ala Val Leu Ala Val Gly Tyr
        275                 280                 285
Gly Glu Lys Asn Gly Ile Pro Tyr Trp Ile Val Lys Asn Ser Trp Gly
    290                 295                 300
Pro Gln Trp Gly Met Asn Gly Tyr Phe Leu Ile Glu Arg Gly Lys Asn
305                 310                 315                 320
```

Met Cys Gly Leu Ala Ala Cys Ala Ser Tyr Pro Ile Pro Leu Val
            325                 330                 335

<210> SEQ ID NO 22
<211> LENGTH: 321
<212> TYPE: PRT
<213> ORGANISM: Human

<400> SEQUENCE: 22

Met Asp Val Arg Ala Leu Pro Trp Leu Pro Trp Leu Leu Trp Leu Leu
 1               5                  10                  15

Cys Arg Gly Gly Gly Asp Ala Asp Ser Arg Ala Pro Phe Thr Pro Thr
            20                  25                  30

Trp Pro Arg Ser Arg Glu Arg Glu Ala Ala Phe Arg Glu Ser Leu
        35                  40                  45

Asn Arg His Arg Tyr Leu Asn Ser Leu Phe Pro Ser Glu Asn Ser Thr
    50                  55                  60

Ala Phe Tyr Gly Ile Asn Gln Phe Ser Tyr Leu Phe Pro Glu Glu Phe
65                  70                  75                  80

Lys Ala Ile Tyr Leu Arg Ser Lys Pro Ser Lys Phe Pro Arg Tyr Ser
                85                  90                  95

Ala Glu Val His Met Ser Ile Pro Asn Val Ser Leu Pro Leu Arg Phe
            100                 105                 110

Asp Trp Arg Asp Lys Gln Val Val Thr Gln Val Arg Asn Gln Gln Met
        115                 120                 125

Cys Gly Gly Cys Trp Ala Phe Ser Val Val Gly Ala Val Glu Ser Ala
130                 135                 140

Tyr Ala Ile Lys Gly Lys Pro Leu Glu Asp Leu Ser Val Gln Gln Val
145                 150                 155                 160

Ile Asp Cys Ser Tyr Asn Asn Tyr Gly Cys Asn Gly Gly Ser Thr Leu
                165                 170                 175

Asn Ala Leu Asn Trp Leu Asn Lys Met Gln Val Lys Leu Val Lys Asp
            180                 185                 190

Ser Glu Tyr Pro Phe Lys Ala Gln Asn Gly Leu Cys His Tyr Phe Ser
        195                 200                 205

Gly Ser His Ser Gly Phe Ser Ile Lys Gly Tyr Ser Ala Tyr Asp Phe
    210                 215                 220

Ser Asp Gln Glu Asp Glu Met Ala Lys Ala Leu Leu Thr Phe Gly Pro
225                 230                 235                 240

Leu Val Val Ile Val Asp Ala Val Ser Trp Gln Asp Tyr Leu Gly Gly
                245                 250                 255

Ile Ile Gln His His Cys Ser Ser Gly Glu Ala Asn His Ala Val Leu
            260                 265                 270

Ile Thr Gly Phe Asp Lys Thr Gly Ser Thr Pro Tyr Trp Ile Val Arg
        275                 280                 285

Asn Ser Trp Gly Ser Ser Trp Gly Val Asp Gly Tyr Ala His Val Lys
    290                 295                 300

Met Gly Ser Asn Val Cys Gly Ile Ala Asp Ser Val Ser Ser Ile Phe
305                 310                 315                 320

Val

<210> SEQ ID NO 23
<211> LENGTH: 376
<212> TYPE: PRT
<213> ORGANISM: Human

<400> SEQUENCE: 23

```
Met Ala Leu Thr Ala His Pro Ser Cys Leu Leu Ala Leu Leu Val Ala
 1               5                  10                  15
Gly Leu Ala Gln Gly Ile Arg Gly Pro Leu Arg Ala Gln Asp Leu Gly
            20                  25                  30
Pro Gln Pro Leu Glu Leu Lys Glu Ala Phe Lys Leu Phe Gln Ile Gln
        35                  40                  45
Phe Asn Arg Ser Tyr Leu Ser Pro Glu Glu His Ala His Arg Leu Asp
    50                  55                  60
Ile Phe Ala His Asn Leu Ala Gln Ala Gln Arg Leu Gln Glu Glu Asp
65                  70                  75                  80
Leu Gly Thr Ala Glu Phe Gly Val Thr Pro Phe Ser Asp Leu Thr Glu
                85                  90                  95
Glu Glu Phe Gly Gln Leu Tyr Gly Tyr Arg Arg Ala Ala Gly Gly Val
            100                 105                 110
Pro Ser Met Gly Arg Glu Ile Arg Ser Glu Pro Glu Glu Ser Val
            115                 120                 125
Pro Phe Ser Cys Asp Trp Arg Lys Val Ala Gly Ala Ile Ser Pro Ile
        130                 135                 140
Lys Asp Gln Lys Asn Cys Asn Cys Cys Trp Ala Met Ala Ala Ala Gly
145                 150                 155                 160
Asn Ile Lys Thr Leu Trp Arg Ile Ser Phe Trp Asp Phe Val Asp Val
                165                 170                 175
Ser Val Gln Glu Leu Leu Asp Cys Gly Arg Cys Gly Asp Gly Cys His
            180                 185                 190
Gly Gly Phe Val Trp Asp Ala Phe Ile Thr Val Leu Asn Asn Ser Gly
            195                 200                 205
Leu Ala Ser Glu Lys Asp Tyr Pro Phe Gln Gly Lys Val Arg Ala His
        210                 215                 220
Arg Cys His Pro Lys Lys Tyr Gln Lys Val Ala Trp Ile Gln Asp Phe
225                 230                 235                 240
Ile Met Leu Gln Asn Asn Glu His Arg Ile Ala Gln Tyr Leu Ala Thr
                245                 250                 255
Tyr Gly Pro Ile Thr Val Thr Ile Asn Met Lys Pro Leu Gln Leu Tyr
            260                 265                 270
Arg Lys Gly Val Ile Lys Ala Thr Pro Thr Thr Cys Asp Pro Gln Leu
        275                 280                 285
Val Asp His Ser Val Leu Leu Val Gly Phe Gly Ser Val Lys Ser Glu
290                 295                 300
Glu Gly Ile Trp Ala Glu Thr Val Ser Ser Gln Ser Gln Pro Gln Pro
305                 310                 315                 320
Pro His Pro Thr Pro Tyr Trp Ile Leu Lys Asn Ser Trp Gly Ala Gln
                325                 330                 335
Trp Gly Glu Lys Gly Tyr Phe Arg Leu His Arg Gly Ser Asn Thr Cys
                340                 345                 350
Gly Ile Thr Lys Phe Pro Leu Thr Ala Arg Val Gln Lys Pro Asp Met
            355                 360                 365
Lys Pro Arg Val Ser Cys Pro Pro
    370                 375
```

<210> SEQ ID NO 24
<211> LENGTH: 339
<212> TYPE: PRT
<213> ORGANISM: Human

<400> SEQUENCE: 24

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr
        35                  40                  45

Asn Val Asp Met Ser Tyr Leu Lys Arg Leu Cys Gly Thr Phe Leu Gly
    50                  55                  60

Gly Pro Lys Pro Pro Gln Arg Val Met Phe Thr Glu Asp Leu Lys Leu
65                  70                  75                  80

Pro Ala Ser Phe Asp Ala Arg Glu Gln Trp Pro Gln Cys Pro Thr Ile
                85                  90                  95

Lys Glu Ile Arg Asp Gln Gly Ser Cys Gly Ser Cys Trp Ala Phe Gly
            100                 105                 110

Ala Val Glu Ala Ile Ser Asp Arg Ile Cys Ile His Thr Asn Ala His
        115                 120                 125

Val Ser Val Glu Val Ser Ala Glu Asp Leu Leu Thr Cys Cys Gly Ser
    130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Gly Leu Tyr Glu Ser His
                165                 170                 175

Val Gly Cys Arg Pro Tyr Ser Ile Pro Pro Cys Glu His His Val Asn
            180                 185                 190

Gly Ser Arg Pro Pro Cys Thr Gly Glu Gly Asp Thr Pro Lys Cys Ser
        195                 200                 205

Lys Ile Cys Glu Pro Gly Tyr Ser Pro Thr Tyr Lys Gln Asp Lys His
    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                245                 250                 255

Ser Asp Phe Leu Leu Tyr Lys Ser Gly Val Tyr Gln His Val Thr Gly
            260                 265                 270

Glu Met Met Gly Gly His Ala Ile Arg Ile Leu Gly Trp Gly Val Glu
        275                 280                 285

Asn Gly Thr Pro Tyr Trp Leu Val Ala Asn Ser Trp Asn Thr Asp Trp
    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                325                 330                 335

Glu Lys Ile

<210> SEQ ID NO 25
<211> LENGTH: 365
<212> TYPE: PRT
<213> ORGANISM: Human

<400> SEQUENCE: 25

Asp Tyr Lys Trp Phe Ala Phe Phe Lys Tyr Lys Glu Glu Gly Ser Lys
1               5                   10                  15

-continued

| | | | | | | | | | | | | |
|---|---|---|---|---|---|---|---|---|---|---|---|---|
|Val|Thr|Thr|Tyr|Cys|Asn|Glu|Thr|Met|Thr|Gly|Trp|Val|His|Asp|Val|
| | | | 20 | | | | 25 | | | | 30 | |
|Leu|Gly|Arg|Asn|Trp|Ala|Cys|Phe|Thr|Gly|Lys|Lys|Val|Gly|Thr|Ala|
| | | 35 | | | | 40 | | | | 45 | | |
|Ser|Glu|Asn|Val|Tyr|Val|Asn|Thr|Ala|His|Leu|Lys|Asn|Ser|Gln|Glu|
| | 50 | | | | 55 | | | | 60 | | | |
|Lys|Tyr|Ser|Asn|Arg|Leu|Tyr|Lys|Tyr|Asp|His|Asn|Phe|Val|Lys|Ala|
| 65 | | | | 70 | | | | 75 | | | | 80 |
|Ile|Asn|Ala|Ile|Gln|Lys|Ser|Trp|Thr|Ala|Thr|Thr|Tyr|Met|Glu|Tyr|
| | | | 85 | | | | 90 | | | | 95 | |
|Glu|Thr|Leu|Thr|Leu|Gly|Asp|Met|Arg|Arg|Ser|Gly|Gly|His|Ser|Arg|
| | | 100 | | | | 105 | | | | 110 | | |
|Lys|Ile|Pro|Arg|Pro|Lys|Pro|Ala|Pro|Leu|Thr|Ala|Glu|Ile|Gln|Gln|
| | 115 | | | | 120 | | | | 125 | | | |
|Lys|Ile|Leu|His|Leu|Pro|Thr|Ser|Trp|Asp|Trp|Arg|Asn|Val|His|Gly|
| 130 | | | | 135 | | | | 140 | | | | |
|Ile|Asn|Phe|Val|Ser|Pro|Val|Arg|Asn|Gln|Ala|Ser|Cys|Gly|Ser|Cys|
| 145 | | | | 150 | | | | 155 | | | | 160 |
|Tyr|Ser|Phe|Ala|Ser|Met|Gly|Met|Leu|Glu|Ala|Arg|Ile|Arg|Ile|Leu|
| | | | 165 | | | | 170 | | | | 175 | |
|Thr|Asn|Asn|Ser|Gln|Thr|Pro|Ile|Leu|Ser|Pro|Gln|Glu|Val|Val|Ser|
| | | 180 | | | | 185 | | | | 190 | | |
|Cys|Ser|Gln|Tyr|Ala|Gln|Gly|Cys|Glu|Gly|Gly|Phe|Pro|Tyr|Leu|Ile|
| | 195 | | | | 200 | | | | 205 | | | |
|Ala|Gly|Lys|Tyr|Ala|Gln|Asp|Phe|Gly|Leu|Val|Glu|Glu|Ala|Cys|Phe|
| 210 | | | | 215 | | | | 220 | | | | |
|Pro|Tyr|Thr|Gly|Thr|Asp|Ser|Pro|Cys|Lys|Met|Lys|Glu|Asp|Cys|Phe|
| 225 | | | | 230 | | | | 235 | | | | 240 |
|Arg|Tyr|Tyr|Ser|Ser|Glu|Tyr|His|Tyr|Val|Gly|Gly|Phe|Tyr|Gly|Gly|
| | | | 245 | | | | 250 | | | | 255 | |
|Cys|Asn|Glu|Ala|Leu|Met|Lys|Leu|Glu|Leu|Val|His|His|Gly|Pro|Met|
| | | 260 | | | | 265 | | | | 270 | | |
|Ala|Val|Ala|Phe|Glu|Val|Tyr|Asp|Asp|Phe|Leu|His|Tyr|Lys|Lys|Gly|
| | 275 | | | | 280 | | | | 285 | | | |
|Ile|Tyr|His|His|Thr|Gly|Leu|Arg|Asp|Pro|Phe|Asn|Pro|Phe|Glu|Leu|
| | 290 | | | | 295 | | | | 300 | | | |
|Thr|Asn|His|Ala|Val|Leu|Leu|Val|Gly|Tyr|Gly|Thr|Asp|Ser|Ala|Ser|
| 305 | | | | 310 | | | | 315 | | | | 320 |
|Gly|Met|Asp|Tyr|Trp|Ile|Val|Lys|Asn|Ser|Trp|Gly|Thr|Gly|Trp|Gly|
| | | | 325 | | | | 330 | | | | 335 | |
|Glu|Asn|Gly|Tyr|Phe|Arg|Ile|Arg|Arg|Gly|Thr|Asp|Glu|Cys|Ala|Ile|
| | | 340 | | | | 345 | | | | 350 | | |
|Glu|Ser|Ile|Ala|Val|Ala|Ala|Thr|Pro|Ile|Pro|Lys|Leu|
| | | 355 | | | | 360 | | | | 365 | |